US009993552B2

(12) United States Patent
Fernandez et al.

(10) Patent No.: US 9,993,552 B2
(45) Date of Patent: Jun. 12, 2018

(54) FORMULATIONS OF SINGLE DOMAIN ANTIGEN BINDING MOLECULES

(71) Applicant: Ablynx N.V., Zwijnaarde (BE)

(72) Inventors: Jason E. Fernandez, Brookline, MA (US); Daniel A. Dixon, Arlington, MA (US); Andrea Paulson, Somerville, MA (US)

(73) Assignee: Ablynx N.V., Ghent-Zwijnaarde (BE)

( * ) Notice: Subject to any disclaimer, the term of this patent is extended or adjusted under 35 U.S.C. 154(b) by 0 days. days.

(21) Appl. No.: 15/041,690

(22) Filed: Feb. 11, 2016

(65) Prior Publication Data

US 2016/0263220 A1 Sep. 15, 2016

Related U.S. Application Data

(63) Continuation of application No. 12/608,553, filed on Oct. 29, 2009, now Pat. No. 9,393,304.

(60) Provisional application No. 61/109,474, filed on Oct. 29, 2008.

(51) Int. Cl.
| | |
|---|---|
| *C07K 16/00* | (2006.01) |
| *C07K 1/00* | (2006.01) |
| *C12P 21/08* | (2006.01) |
| *A61K 39/395* | (2006.01) |
| *A61K 9/00* | (2006.01) |
| *A61K 9/19* | (2006.01) |
| *A61K 47/10* | (2017.01) |
| *A61K 47/26* | (2006.01) |
| *G06Q 99/00* | (2006.01) |
| *A61K 9/16* | (2006.01) |
| *C07K 16/18* | (2006.01) |
| *C07K 16/24* | (2006.01) |
| *G01N 33/15* | (2006.01) |
| *A61K 39/00* | (2006.01) |

(52) U.S. Cl.
CPC ...... *A61K 39/39591* (2013.01); *A61K 9/0019* (2013.01); *A61K 9/1617* (2013.01); *A61K 9/1623* (2013.01); *A61K 9/1641* (2013.01); *A61K 9/19* (2013.01); *A61K 47/10* (2013.01); *A61K 47/26* (2013.01); *C07K 16/18* (2013.01); *C07K 16/241* (2013.01); *G01N 33/15* (2013.01); *G06Q 99/00* (2013.01); *A61K 2039/507* (2013.01); *C07K 2317/22* (2013.01); *C07K 2317/24* (2013.01); *C07K 2317/565* (2013.01); *C07K 2317/569* (2013.01)

(58) Field of Classification Search
None
See application file for complete search history.

(56) References Cited

U.S. PATENT DOCUMENTS

| | | |
|---|---|---|
| 4,474,893 A | 10/1984 | Reading et al. |
| 4,714,681 A | 12/1987 | Reading et al. |
| 4,816,397 A | 3/1989 | Boss et al. |
| 4,816,567 A | 3/1989 | Cabilly et al. |
| 4,925,648 A | 5/1990 | Hansen et al. |
| 5,223,409 A | 6/1993 | Lander et al. |
| 5,225,539 A | 7/1993 | Winter et al. |
| 5,573,920 A | 11/1996 | Randle et al. |
| 5,585,089 A | 12/1996 | Queen et al. |
| 5,601,819 A | 2/1997 | Wong et al. |
| 5,603,959 A | 2/1997 | Horrobin et al. |
| 5,693,761 A | 12/1997 | Queen et al. |
| 5,693,762 A | 12/1997 | Queen et al. |
| 5,731,168 A | 3/1998 | Carter et al. |
| 5,807,706 A | 9/1998 | Carter et al. |
| 5,821,333 A | 10/1998 | Carter et al. |
| 5,843,440 A | 12/1998 | Pouletty et al. |
| 5,859,205 A | 1/1999 | Adair et al. |
| 5,891,996 A | 4/1999 | Mateo de Acosta del Rio et al. |
| 5,895,205 A | 4/1999 | Werner et al. |
| 5,976,532 A | 11/1999 | Coller et al. |
| 6,300,064 B1 | 10/2001 | Knappik et al. |
| 6,407,213 B1 | 6/2002 | Carter et al. |
| 6,419,934 B1 | 7/2002 | Tobinick |
| 6,491,934 B1 | 12/2002 | Bekele |
| 6,670,453 B2 | 12/2003 | Frenken et al. |
| 6,759,518 B1 | 7/2004 | Kontermann et al. |
| 7,084,257 B2 | 8/2006 | Deshpande et al. |
| 7,300,655 B2 | 11/2007 | Hansen et al. |
| 7,368,111 B2 | 5/2008 | Thompson et al. |
| 8,071,394 B2 | 12/2011 | Wu et al. |
| 9,393,304 B2 | 7/2016 | Fernandez et al. |

(Continued)

FOREIGN PATENT DOCUMENTS

| | | |
|---|---|---|
| CN | 101248087 | 8/2008 |
| EP | 0 171 496 A2 | 2/1986 |
| EP | 0 173 494 A2 | 3/1986 |
| EP | 0 239 400 A2 | 9/1987 |

(Continued)

OTHER PUBLICATIONS

Zhang et al., Applications of Modulated Differential Scanning Calorimetry in Polymer Studies. China Acad J. Electronic Publishing House. 2004;341-348.

(Continued)

*Primary Examiner* — Shulamith H Shafer
(74) *Attorney, Agent, or Firm* — Wolf, Greenfield & Sacks, P.C.

(57) ABSTRACT

The invention relates to formulations of single domain antigen binding molecules, e.g., nanobody molecules, in particular formulations of TNF-binding nanobody molecules. The single domain antigen binding molecules can include one or more single binding domains that interact with, e.g., bind to, one or more target proteins. The formulations are useful, e.g., as pharmaceutical formulations. Method of preparing, and using the formulations described herein, to treat, e.g., TNF-associated disorders, are also disclosed.

9 Claims, 32 Drawing Sheets

(56) References Cited

U.S. PATENT DOCUMENTS

| | | |
|---|---|---|
| 2002/0001587 A1 | 1/2002 | Erickson et al. |
| 2002/0054878 A1 | 5/2002 | Lowe et al. |
| 2002/0058033 A1 | 5/2002 | Raisch et al. |
| 2002/0132275 A1 | 9/2002 | Fidler et al. |
| 2002/0155537 A1 | 10/2002 | Carter et al. |
| 2002/0165387 A1 | 11/2002 | Kerr Anderson et al. |
| 2003/0020734 A1 | 1/2003 | Yin et al. |
| 2003/0070185 A1 | 4/2003 | Jakobovits et al. |
| 2003/0092892 A1 | 5/2003 | Frenken et al. |
| 2004/0219643 A1 | 11/2004 | Winter et al. |
| 2005/0215470 A1 | 9/2005 | Ng et al. |
| 2005/0266000 A1 | 12/2005 | Bond et al. |
| 2005/0271663 A1 | 12/2005 | Ignatovich et al. |
| 2006/0034833 A1 | 2/2006 | Silence et al. |
| 2006/0034845 A1 | 2/2006 | Silence et al. |
| 2006/0073113 A1 | 4/2006 | Nakamoto et al. |
| 2006/0106203 A1 | 5/2006 | Winter et al. |
| 2006/0115470 A1 | 6/2006 | Silence et al. |
| 2006/0153860 A1 | 7/2006 | Cho et al. |
| 2006/0228355 A1 | 10/2006 | Silence et al. |
| 2006/0286066 A1 | 12/2006 | Basran et al. |
| 2007/0077249 A1 | 4/2007 | Silence et al. |
| 2007/0178082 A1 | 8/2007 | Silence et al. |
| 2007/0237769 A1 | 10/2007 | Silence et al. |
| 2008/0107601 A1 | 5/2008 | Lauwereys et al. |
| 2008/0260757 A1 | 10/2008 | Holt et al. |
| 2009/0022721 A1 | 1/2009 | Silence et al. |
| 2009/0238829 A1 | 9/2009 | Silence et al. |
| 2009/0297535 A1 | 12/2009 | Kolkman et al. |
| 2009/0306348 A1 | 12/2009 | Goldstein et al. |
| 2009/0324512 A1 | 12/2009 | Silence et al. |
| 2010/0003248 A1 | 1/2010 | Silence et al. |
| 2010/0003249 A1 | 1/2010 | Silence et al. |
| 2010/0003253 A1 | 1/2010 | Laeremans et al. |
| 2010/0021459 A1 | 1/2010 | Silence et al. |
| 2010/0040613 A1 | 2/2010 | Silence et al. |
| 2010/0077422 A1 | 3/2010 | Bushinsky |
| 2010/0137213 A1 | 6/2010 | Fernandez et al. |
| 2010/0172894 A1 | 7/2010 | Brown et al. |
| 2010/0297111 A1 | 11/2010 | Beirnaert et al. |
| 2011/0097302 A1 | 4/2011 | Yuan et al. |
| 2011/0183861 A1 | 7/2011 | Jonniaux et al. |
| 2012/0014975 A1 | 1/2012 | Hegen et al. |

FOREIGN PATENT DOCUMENTS

| | | |
|---|---|---|
| EP | 0 368 684 B1 | 5/1990 |
| EP | 0 584 421 A1 | 3/1994 |
| EP | 0 589 840 A1 | 3/1994 |
| EP | 0 952 218 A2 | 10/1999 |
| EP | 0 954 978 A1 | 11/1999 |
| EP | 1 002 861 A1 | 5/2000 |
| EP | 1 118 669 A2 | 7/2001 |
| EP | 1 816 198 A1 | 8/2007 |
| GB | 2177096 A | 1/1987 |
| GB | 0 115 841.9 | 6/2001 |
| GB | 0 230 202.4 | 12/2002 |
| JP | H09-503384 | 4/1997 |
| JP | H11-510170 A | 9/1999 |
| JP | 2003-516361 | 5/2003 |
| JP | 2006-249081 | 9/2006 |
| JP | 2006-249083 | 9/2006 |
| JP | 2006-249084 | 9/2006 |
| JP | 2007-532477 T2 | 11/2007 |
| JP | 2008-533473 A | 8/2008 |
| WO | WO 1990/02809 A1 | 3/1990 |
| WO | WO 1990/05144 A1 | 5/1990 |
| WO | WO 1990/10707 A1 | 9/1990 |
| WO | WO 1991/00360 A1 | 1/1991 |
| WO | WO 1991/01743 A1 | 2/1991 |
| WO | WO 1991/02078 A1 | 2/1991 |
| WO | WO 1991/17271 A1 | 11/1991 |
| WO | WO 1992/01047 A1 | 1/1992 |
| WO | WO 1992/01787 A1 | 2/1992 |
| WO | WO 1992/05793 A1 | 4/1992 |
| WO | WO 1992/06193 A1 | 4/1992 |
| WO | WO 1992/08802 A1 | 5/1992 |
| WO | WO 1992/09690 A2 | 6/1992 |
| WO | WO 1992/15679 A1 | 9/1992 |
| WO | WO 1992/16142 A1 | 10/1992 |
| WO | WO 1992/18619 A1 | 10/1992 |
| WO | WO 1992/20791 A1 | 11/1992 |
| WO | WO 1993/01288 A1 | 1/1993 |
| WO | WO 1993/17715 A1 | 9/1993 |
| WO | WO 1994/04678 A1 | 3/1994 |
| WO | WO 1995/10302 A1 | 4/1995 |
| WO | WO 1996/033735 A1 | 10/1996 |
| WO | WO 1996/34096 A1 | 10/1996 |
| WO | WO 1996/34103 A1 | 10/1996 |
| WO | WO 1997/004801 A1 | 2/1997 |
| WO | WO 1997/029131 A1 | 8/1997 |
| WO | WO 1998/52976 A1 | 11/1998 |
| WO | WO 1999/09055 A2 | 2/1999 |
| WO | WO 1999/23221 A2 | 5/1999 |
| WO | WO 1999/64069 A1 | 12/1999 |
| WO | WO 2000/29004 A1 | 5/2000 |
| WO | WO 2000/34317 A2 | 6/2000 |
| WO | WO 2000/044788 A1 | 8/2000 |
| WO | WO 2000/56772 A2 | 9/2000 |
| WO | WO 2001/41800 A2 | 6/2001 |
| WO | WO 2001/45746 A2 | 6/2001 |
| WO | WO 2001/58956 A2 | 8/2001 |
| WO | WO 2002/015537 A2 | 2/2002 |
| WO | WO 2002/096948 A2 | 5/2002 |
| WO | WO 2002/048193 A2 | 6/2002 |
| WO | WO 2002/051351 A2 | 7/2002 |
| WO | WO 2002/057445 A1 | 7/2002 |
| WO | WO 2002/079781 A1 | 10/2002 |
| WO | WO 2003/014161 A2 | 2/2003 |
| WO | WO 2003/020734 A2 | 3/2003 |
| WO | WO 2003/035694 A2 | 5/2003 |
| WO | WO 2003/080672 A1 | 10/2003 |
| WO | WO 2004/003019 A2 | 1/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A1 | 5/2004 |
| WO | WO 2004/060965 A2 | 7/2004 |
| WO | WO 2004/060966 A2 | 7/2004 |
| WO | WO 2004/081026 A2 | 9/2004 |
| WO | WO 2005/044856 A2 | 5/2005 |
| WO | WO 2005/044865 A2 | 5/2005 |
| WO | WO 2006/003388 A2 | 1/2006 |
| WO | WO 2006/059108 A2 | 6/2006 |
| WO | WO 2006/096491 A2 | 9/2006 |
| WO | WO 2006/099308 A2 | 9/2006 |
| WO | WO 2006/122786 A2 | 11/2006 |
| WO | WO 2006/122787 * 11/2006 ............. C07K 16/18 |
| WO | WO 2006/138553 A2 | 12/2006 |
| WO | WO 2006/138737 A2 | 12/2006 |
| WO | WO 2007/014073 A2 | 2/2007 |
| WO | WO 2007/095337 A2 | 8/2007 |
| WO | WO 2007/100535 A2 | 9/2007 |
| WO | WO 2008/071394 A2 | 6/2008 |
| WO | WO 2008/074868 A1 | 6/2008 |
| WO | WO 2008/077945 A2 | 7/2008 |
| WO | WO 2008/086335 A2 | 7/2008 |
| WO | WO 2008/116103 A2 | 9/2008 |
| WO | WO 2009/068627 A2 | 6/2009 |
| WO | WO 2009/133137 A2 | 11/2009 |
| WO | WO 2010/055950 A1 | 5/2010 |
| WO | WO 2010/056550 A1 | 5/2010 |
| WO | WO 2010/060212 A1 | 6/2010 |
| WO | WO 2010/077422 A2 | 7/2010 |
| WO | WO 2011/026948 A1 | 3/2011 |
| WO | WO 2012/155780 A1 | 11/2012 |

OTHER PUBLICATIONS

Zhou, Determining Protein Half-Lives. Methods in Molecular Biology, vol. 284: Signal Transduction Protocols. Edited by: R.C. Dickson. Humana Press Inc., Totowa, NJ. 2004:67-77.

(56) References Cited

OTHER PUBLICATIONS

PCT/IB2011/053007, Feb. 23, 2012, International Search Report and Written Opinion.
PCT/US2007/022256, Jun. 27, 2008, International Search Report.
PCT/US2007/022256, Apr. 22, 2009, International Preliminary Report on Patentability.
Altschul et al., Basic local alignment search tool. J Mol Biol. Oct. 5, 1990;215(3):403-10.
Altschul et al., Gapped BLAST and PSI-BLAST: a new generation of protein database search programs. Nucleic Acids Res. Sep. 1, 1997;25(17):3389-402.
Arakawa et al., Protein—solvent interactions in pharmaceutical formulations. Pharm Res. Mar. 1991;8(3):285-91.
Arbabi Ghahroudi et al., Selection and identification of single domain antibody fragments from camel heavy-chain antibodies. Febs Lett. Sep. 15, 1997;414(3):521-6.
Benhar et al., Mutations of two lysine residues in the CDR loops of a recombinant immunotoxin that reduce its sensitivity to chemical derivatization. Bioconjug Chem. Jul.-Aug. 1994;5(4):321-6.
Birch et al., Monoclonal antibodies. Principles and Applications. 1st ed. 1995:237-247.
Blank et al., Expanded bed adsorption in the purification of monoclonal antibodies: a comparison of process alternatives. Bioseparation. 2001;10(1-3):65-71.
Bollag, Ion-exchange chromatography. Methods Mol Biol. 1994;36:11-22.
Bond et al., A structure-based database of antibody variable domain diversity. J Mol Biol. May 6, 2005;348(3):699-709.
Capelle et al., High throughput screening of protein formulation stability: practical considerations. Eur J Pharm Biopharm. Feb. 2007;65(2):131-48. Epub Sep. 29, 2006.
Carpenter et al., Potential inaccurate quantitation and sizing of protein aggregates by size exclusion chromatography: essential need to use orthogonal methods to assure the quality of therapeutic protein products. J Pharm Sci. May 2010;99(5):2200-8. doi: 10.1002/jps.21989.
Cedergren et al., Mutational analysis of the interaction between staphylococcal protein A and human IgG1. Protein Eng. Jun. 1993;6(4):441-8.
Chapman, PEGylated antibodies and antibody fragments for improved therapy: a review. Adv Drug Deliv Rev. Jun. 17, 2002;54(4):531-45.
Chothia et al., Canonical structures for the hypervariable regions of immunoglobulins. J Mol Biol. Aug. 20, 1987;196(4):901-17.
Chothia et al., Structural repertoire of the human VH segments. J Mol Biol. Oct. 5, 1992;227(3):799-817.
Chuang et al., Pharmaceutical strategies utilizing recombinant human serum albumin. Pharm Res. May 2002;19(5):569-77.
Cleland et al., The development of stable protein formulations: a close look at protein aggregation, deamidation, and oxidation. Crit Rev Ther Drug Carrier Syst. 1993;10(4):307-77.
Colman et al., Effects of amino acid sequence changes on antibody-antigen interactions. Res Immunol. Jan. 1994;145(1):33-6.
Connelly, Fully human domain antibody therapeutics: the best of both worlds. Innovations in Pharmaceutical Technol. 2005;:42-5.
Cook et al., The human immunoglobulin VH repertoire. Immunol Today. May 1995;16(5):237-42.
Cortez-Retamozo et al., Efficient tumor targeting by single-domain antibody fragments of camels. Int J Cancer. Mar. 20, 2002;98(3):456-62.
Daugherty et al., Formulation and delivery issues for monoclonal antibody therapeutics. Adv Drug Deliv Rev. Aug. 7, 2006;58(5-6):686-706. Epub May 22, 2006.
Davies et al., Antibody VH domains as small recognition units. Biotechnology (N Y). May 1995;13(5):475-9.
Decherchi et al., Implicit solvent methods for free energy estimation. Eur J Med Chem. Feb. 16, 2015;91C:27-42. doi: 10.1016/j.ejmech.2014.08.064. Epub Aug. 25, 2014.

Desmyter et al., Antigen specificity and high affinity binding provided by one single loop of a camel single-domain antibody. J Biol Chem. Jul. 13, 2001;276(28):26285-90. Epub May 7, 2001.
D'Haens et al., Endoscopic and histological healing with infliximab anti-tumor necrosis factor antibodies in Crohn's disease: A European multicenter trial. Gastroenterology. May 1999;116(5):1029-34.
Eliasson et al., Differential IgG-binding characteristics of staphylococcal protein A, streptococcal protein G, and a chimeric protein AG. J Immunol. Jan. 15, 1989;142(2):575-81.
Els Conrath et al., Camel single-domain antibodies as modular building units in bispecific and bivalent antibody constructs. J Biol Chem. Mar. 9, 2001;276(10):7346-50. Epub Oct. 25, 2000.
Fahrner et al., Industrial purification of pharmaceutical antibodies: development, operation, and validation of chromatography processes. Biotechnol Genet Eng Rev. 2001;18:301-27.
Frenken et al., Isolation of antigen specific llama VHH antibody fragments and their high level secretion by *Saccharomyces cerevisiae*. J Biotechnol. Feb. 28, 2000;78(1):11-21.
Fuller et al., Purification of monoclonal antibodies. Curr Protoc Mol Biol. May 2001;Chapter 11:Unit11.11. doi: 10.1002/0471142727.mb1111s37.
Ghose et al., Antibody variable region interactions with Protein A: implications for the development of generic purification processes. Biotechnol Bioeng. Dec. 20, 2005;92(6):665-73.
Gil et al., Strategies to stabilize compact folding and minimize aggregation of antibody-based fragments. Adv Biosci Biotechnol. Apr. 2013;4(4a):73-84.
Gokarn et al., Excipients for Protein Drugs. Ashok et al., (Eds.) 2006. Chapter 17:291-331.
Green et al., Antigen-specific human monoclonal antibodies from mice engineered with human Ig heavy and light chain YACs. Nat Genet. May 1994;7(1):13-21.
Gupta et al., Development of a Multidose Formulation for a Humanized Monoclonal Antibody Using Experimental Design Techniques. AAPSPharm Sci. 2003;5:article 8, p. 1-9.
Hagihara et al., Cellular quality control screening to identify amino acid pairs for substituting the disulfide bonds in immunoglobulin fold domains. J Biol Chem. Jul. 1, 2005;280(26):24752-8. Epub May 3, 2005.
Hagihara et al., Stabilization of an immunoglobulin fold domain by an engineered disulfide bond at the buried hydrophobic region. J Biol Chem. Dec. 14, 2007;282(50):36489-95. Epub Oct. 11, 2007.
Hamers-Casterman et al., Naturally occurring antibodies devoid of light chains. Nature. Jun. 3, 1993;363(6428):446-8.
Harinarayan et al., An exclusion mechanism in ion exchange chromatography. Biotechnol Bioeng. Dec. 5, 2006;95(5):775-87.
Harmsen et al., Llama heavy-chain V regions consist of at least four distinct subfamilies revealing novel sequence features. Mol Immunol. Aug. 2000;37(10):579-90.
Harmsen et al., Passive immunization of guinea pigs with llama single-domain antibody fragments against foot-and-mouth disease. Vet Microbiol. Mar. 10, 2007;120(3-4):193-206. Epub Oct. 28, 2006.
Harmsen et al., Passive immunization of pigs with bispecific llama single-domain antibody fragments against foot-and-mouth disease and porcine immunoglobulin. Vet Microbiol. Nov. 25, 2008;132(1-2):56-64. Epub Apr. 30, 2008.
Harris et al., Effect of pegylation on pharmaceuticals. Nat Rev Drug Discov. Mar. 2003;2(3):214-21.
Hasemann et al., Immunoglobulins: Structure and Function, in William E. Paul, ed. Fundamental Immunology, Second Ed. 1989;209:210-18.
Hawe et al., Forced Degradation of Therapeutic Proteins. J. Pharm Sci. Mar. 2012. 101(3):895-913.
Hober et al., Protein A chromatography for antibody purification. J Chromatogr B Analyt Technol Biomed Life Sci. Mar. 15, 2007;848(1):40-7. Epub Oct. 9, 2006.
Holliger et al., Retargeting serum immunoglobulin with bispecific diabodies. Nat Biotechnol. Jul. 1997;15(7):632-6.
Hoogenboom, Mix and match: building manifold binding sites. Nat Biotechnol. Feb. 1997;15(2):125-6.

(56) References Cited

OTHER PUBLICATIONS

Kostelny et al., Formation of a bispecific antibody by the use of leucine zippers. J Immunol. Mar. 1, 1992;148(5):1547-53.

Koumenis et al., Modulating pharmacokinetics of an anti-interleukin-8 F(ab')(2) by amine-specific PEGylation with preserved bioactivity. Int J Pharm. Mar. 30, 2000;198(1):83-95.

Kozbor et al., The production of monoclonal antibodies from human lymphocytes. Immunology Today. 1983;4:72-79.

Krinner et al., A highly stable polyethylene glycol-conjugated human single-chain antibody neutralizing granulocyte-macrophage colony stimulating factor at low nanomolar concentration. Protein Eng Des Sel. Oct. 2006;19(10):461-70. Epub Jul. 25, 2006.

Leong et al., Adapting pharmacokinetic properties of a humanized anti-interleukin-8 antibody for therapeutic applications using site-specific pegylation. Cytokine Nov. 7, 2001;16(3):106-19.

Ljungberg et al., The interaction between different domains of staphylococcal protein A and human polyclonal IgG, IgA, IgM and F(ab')2: separation of affinity from specificity. Mol Immunol. Oct. 1993;30(14):1279-85.

Low et al., Future of antibody purification. J Chromatogr B Analyt Technol Biomed Life Sci. Mar. 15, 2007;848(1):48-63. Epub Nov. 28, 2006.

Lu et al., Effect of PEGylation on the solution conformation of antibody fragments. J Pharm Sci. Jun. 2008;97(6):2062-79.

MacEwan, TNF ligands and receptors—a matter of life and death. Br J Pharmacol. Feb. 2002;135(4):855-75.

Mallender et al., Construction, expression, and activity of a bivalent bispecific single-chain antibody. J Biol Chem. Jan. 7, 1994;269(1):199-206.

Martin, Protein Sequence and Structure Analysis of Antibody Variable Domains. In: Antibody Engineering Lab Manual (Ed.: Duebel, Kontermann, Springer-Verlag, Heidelberg). Chapter 3. 2010. 33-51.

Monfardini et al., A branched monomethoxypoly(ethylene glycol) for protein modification. Bioconjugate Chem. Jan. 1, 1995;6(1):62-69.

Morrison et al., Chimeric human antibody molecules: mouse antigen-binding domains with human constant region domains. Proc Natl Acad Sci U S A. Nov. 1984;81(21):6851-5.

Morrison, Transfectomas provide novel chimeric antibodies. Science. Sep. 20, 1985;229(4719):1202-7.

Muyldermans et al., Single domain camel antibodies: current status. J Biotechnol. Jun. 2001;74(4):277-302.

Muyldermans et al., Unique single-domain antigen binding fragments derived from naturally occurring camel heavy-chain antibodies. J Mol Recognit. Mar.-Apr. 1999;12(2):131-40.

Myers et al., Optimal alignments in linear space. CABIOS. 1989;4:11-7.

Needleman et al., A general method applicable to the search for similarities in the amino acid sequence of two proteins. J Mol Biol. Mar. 1970;48(3):443-53.

Nieba et al., Disrupting the hydrophobic patches at the antibody variable/constant domain interface: improved in vivo folding and physical characterization of an engineered scFv fragment. Protein Eng. Apr. 1997;10(4):435-44.

Nilsson et al., A synthetic IgG-binding domain based on staphylococcal protein A. Protein Eng. Feb.-Mar. 1987;1(2):107-13.

Nilsson et al., Affinity fusion strategies for detection, purification, and immobilization of recombinant proteins. Protein Expr Purif. Oct. 1997;11(1):1-16.

O'Donnell et al., A high capacity strong cation exchange resin for the chromatographic purification of monoclonal antibodies and other proteins. PREP. 2007;:1-13.

Oi et al., Chimeric Antibodies. BioTechniques. 1986;4:214.

Olsson et al., Human—human monoclonal antibody-producing hybridomas: technical aspects. Methods Enzymol. 1983;92:3-16.

Paul, Fundamental Immunology, 3rd Edition, under the heading "Fv Structure and Diversity in Three Dimensions." 1993;:292-5.

Pikal, Freeze drying of proteins part II: formulation selection. Biopharm. 1990;3(9):26-30.

Reen et al., Enzyme-linked immunosorbent assay (ELISA). Methods Mol Biol. 1994;32:461-6.

Riechmann et al., Single domain antibodies: comparison of camel VH and camelised human VH domains. J Immunol Methods. Dec. 10, 1999;231(1-2):25-38.

Ring et al., Anaphylactoid reactions to infusions of plasma protein and human serum albumin. Role of aggregated proteins and of stabilizers added during production. Clin Allergy. Jan. 1979;9(1):89-97. Abstract only.

Roben et al., VH3 family antibodies bind domain D of staphylococcal protein A. J Immunol. Jun. 15, 1995;154(12):6437-45.

Roberts et al., Chemistry for peptide and protein PEGylation. Adv Drug Deliv Rev. Jun. 17, 2002;54(4):459-76.

Roguin et al., Monoclonal antibodies inducing conformational change on the antigen molecule. Scandinavian Journal of Immunology. 2003;58:387-94.

Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.

Rudikoff et al., Single amino acid substitution altering antigen-binding specificity. Proc Natl Acad Sci U S A. Mar. 1982;79(6):1979-83.

Rutkoski et al., Human ribonuclease with a pendant poly(ethylene glycol) inhibits tumor growth in mice. Transl Oncol. Aug. 1, 2013;6(4):392-7. Print Aug. 2013 Erratum in: Transl Oncol. 2013;6:5.

Saelman et al., Platelet adhesion to collagen types I through VIII under conditions of stasis and flow is mediated by GPIa/IIa (alpha 2 beta 1-integrin). Blood. Mar. 1, 1994;83(5):1244-50.

Scheurich et al., Quantification and characterization of high-affinity membrane receptors for tumor necrosis factor on human leukemic cell lines. Int J Cancer. Jul. 15, 1986;38(1):127-33.

Shumway et al., XM-ONE[reg] Part 1: The challenges of flow cytometric crossmatching (fcxm) with endotheliallmonocyte. American Society for Histocompatibility and Immunogenetics. Poster Session.2009. Abstract 60-P.

Sjodahl et al., Structural studies on the four repetitive Fc-binding regions in protein A from *Staphylococcus aureus*. Eur J Biochem. Sep. 1977;78(2):471-90.

Smith et al., Prolonged in vivo residence times of antibody fragments associated with albumin. Bioconjug Chem. Sep.-Oct. 2001;12(5):750-6.

Smith, Filamentous fusion phage: novel expression vectors that display cloned antigens on the virion surface. Science. Jun. 14, 1985;228(4705):1315-7.

Starovasnik et al., Antibody variable region binding by Staphylococcal protein A: thermodynamic analysis and location of the Fv binding site on E-domain. Protein Sci. Jul. 1999;8(7):1423-31.

Steindl et al., A simple method to quantify staphylococcal protein A in the presence of human or animal IgG in various samples. J Immunol Methods. Feb. 21, 2000;235(1-2):61-9.

Stoscheck, Quantitation of protein. Methods Enzymol. 1990;182:50-68.

Streltsov et al., Structure of a shark IgNAR antibody variable domain and modeling of an early-developmental isotype. Protein Sci. Nov. 2005;14(11):2901-9. Epub Sep. 30, 2005.

Takeda et al., Construction of chimaeric processed immunoglobulin genes containing mouse variable and human constant region sequences. Nature. Apr. 4-10, 1985;314(6010):452-4.

Tamura et al., Structural correlates of an anticarcinoma antibody: identification of specificity-determining residues (SDRs) and development of a minimally immunogenic antibody variant by retention of SDRs only. J Immunol. Feb. 1, 2000;164(3):1432-41.

Tanha et al., Selection by phage display of llama conventional V(H) fragments with heavy chain antibody V(H)H properties. J Immunol Methods. May 1, 2002;263(1-2):97-109.

Tarditi et al., Selective high-performance liquid chromatographic purification of bispecific monoclonal antibodies. J Chromatogr. May 22, 1992;599(1-2):13-20.

Teng et al., Construction and testing of mouse—human heteromyelomas for human monoclonal antibody production. Proc Natl Acad Sci U S A. Dec. 1983;80(23):7308-12.

(56) References Cited

OTHER PUBLICATIONS

Tomlinson et al., The repertoire of human germline VH sequences reveals about fifty groups of VH segments with different hypervariable loops. J Mol Biol. Oct. 5, 1992;227(3):776-98.

Tomlinson et al., The structural repertoire of the human V kappa domain. EMBO J. Sep. 15, 1995;14(18):4628-38.

Tutt et al., Trispecific F(ab')3 derivatives that use cooperative signaling via the TCR/CD3 complex and CD2 to activate and redirect resting cytotoxic T cells. J Immunol. Jul. 1, 1991;147(1):60-9.

Uhlén et al., Complete sequence of the staphylococcal gene encoding protein A. A gene evolved through multiple duplications. J Biol Chem. Feb. 10, 1984;259(3):1695-702.

Valle et al., Infliximab. Expert Opin Pharmacother. Jun. 2001;2(6):1015-25.

Veronese et al., Introduction and overview of peptide and protein pegylation. Adv Drug Deliv Rev. Jun. 17, 2002;54(4):453-6.

Wang, Lyophilization and development of solid protein pharmaceuticals. Int J Pharm. Aug. 10, 2000;203(1-2):1-60.

Ward et al., Binding activities of a repertoire of single immunoglobulin variable domains secreted from *Escherichia coli*. Nature. Oct. 12, 1989;341(6242):544-6.

Worledge et al., Oral administration of avian tumor necrosis factor antibodies effectively treats experimental colitis in rats. Digestive Diseases and Sciences. Dec. 2000;45(12):2298-305.

Yamagishi et al., A new set of atomic radii for accurate estimation of solvation free energy by Poisson-Boltzmann solvent model. J Comput Chem. Nov. 5, 2014;35(29):2132-9. doi: 10.1002/jcc.23728. Epub Sep. 15, 2014.

Yang et al., Tailoring structure-function and pharmacokinetic properties of single-chain Fv proteins by site-specific PEGylation. Protein Eng. Oct. 2003;16(10):761-70.

Yang et al., Tumor necrosis factor alpha blocking peptide loaded PEG-PLGA nanoparticles: preparation and in vitro evaluation. Int J Pharm. Feb. 22, 2007;331(1):123-32. Epub Sep. 17, 2006.

Zhou et al., Variational Implicit Solvation with Poisson-Boltzmann Theory. J Chem Theory Comput. Apr. 8, 2014;10(4):1454-1467. Epub Feb. 21, 2014.

* cited by examiner

```
                                      -19 MGWSCIILFLVATATGVHS   -1

1 EVQLVESGGGLVQPGGSLRLSCAASGFTFSDYWMYWVRQAPGKGLEWVSEINTNGLITKY  60

61 PDSVKGRFTISRDNAKNTLYLQMNSLRPEDTAVYYCARSPSGFNRGQGTLVTVSSGGGGS 120

121 GGGSEVQLVESGGGLVQPGNSLRLSCAASGFTFSSFGMSWVRQAPGKGLEWVSSISGSGS 180

181 DTLYADSVKGRFTISRDNAKTTLYLQMNSLRPEDTAVYYCTIGGSLSRSSQGTLVTVSSG 240

241 GGGSGGGSEVQLVESGGGLVQPGGSLRLSCAASGFTFSDYWMYWVRQAPGKGLEWVSEIN 300

301 TNGLITKYPDSVKGRFTISRDNAKNTLYLQMNSLRPEDTAVYYCARSPSGFNRGQGTLVT 360

361 VSS (SEQ ID NO:1)
```

FIGURE 30

SEQUENCE LISTING

<160> NUMBER OF SEQ ID NOS: 10

<210> SEQ ID NO 1
<211> LENGTH: 382
<212> TYPE: PRT
<213> ORGANISM: Artificial Sequence

```
<220> FEATURE:
<223> OTHER INFORMATION: Synthetic polypeptide
<220> FEATURE:
<221> NAME/KEY: signal
<222> LOCATION: (1)..(19)
<220> FEATURE:
<221> NAME/KEY: mat_peptide
<222> LOCATION: (20)..(382)

<400> SEQUENCE: 1
```

Met Gly Trp Ser Cys Ile Ile Leu Phe Leu Val Ala Thr Ala Thr Gly
            -15                 -10                  -5

Val His Ser Glu Val Gln Leu Val Glu Ser Gly Gly Gly Leu Val Gln
         -1   1                5                  10

Pro Gly Gly Ser Leu Arg Leu Ser Cys Ala Ala Ser Gly Phe Thr Phe
     15                  20                  25

Ser Asp Tyr Trp Met Tyr Trp Val Arg Gln Ala Pro Gly Lys Gly Leu
 30                  35                  40                  45

Glu Trp Val Ser Glu Ile Asn Thr Asn Gly Leu Ile Thr Lys Tyr Pro
                 50                  55                  60

Asp Ser Val Lys Gly Arg Phe Thr Ile Ser Arg Asp Asn Ala Lys Asn
                 65                  70                  75

Thr Leu Tyr Leu Gln Met Asn Ser Leu Arg Pro Glu Asp Thr Ala Val
             80                  85                  90

Tyr Tyr Cys Ala Arg Ser Pro Ser Gly Phe Asn Arg Gly Gln Gly Thr
 95                 100                 105

Leu Val Thr Val Ser Ser Gly Gly Gly Ser Gly Gly Gly Ser Glu
110                 115                 120                 125

Val Gln Leu Val Glu Ser Gly Gly Leu Val Gln Pro Gly Asn Ser
                130                 135                 140

Leu Arg Leu Ser Cys Ala Ala Ser Gly Phe Thr Phe Ser Ser Phe Gly
                145                 150                 155

Met Ser Trp Val Arg Gln Ala Pro Gly Lys Gly Leu Glu Trp Val Ser
                160                 165                 170

Ser Ile Ser Gly Ser Gly Ser Asp Thr Leu Tyr Ala Asp Ser Val Lys
             175                 180                 185

Gly Arg Phe Thr Ile Ser Arg Asp Asn Ala Lys Thr Thr Leu Tyr Leu
190                 195                 200                 205

Gln Met Asn Ser Leu Arg Pro Glu Asp Thr Ala Val Tyr Tyr Cys Thr
                210                 215                 220

Ile Gly Gly Ser Leu Ser Arg Ser Ser Gln Gly Thr Leu Val Thr Val
             225                 230                 235

Ser Ser Gly Gly Gly Gly Ser Gly Gly Gly Ser Glu Val Gln Leu Val
         240                 245                 250

Glu Ser Gly Gly Gly Leu Val Gln Pro Gly Gly Ser Leu Arg Leu Ser
     255                 260                 265

Cys Ala Ala Ser Gly Phe Thr Phe Ser Asp Tyr Trp Met Tyr Trp Val
270                 275                 280                 285

Arg Gln Ala Pro Gly Lys Gly Leu Glu Trp Val Ser Glu Ile Asn Thr
                290                 295                 300

Asn Gly Leu Ile Thr Lys Tyr Pro Asp Ser Val Lys Gly Arg Phe Thr
             305                 310                 315

Ile Ser Arg Asp Asn Ala Lys Asn Thr Leu Tyr Leu Gln Met Asn Ser
         320                 325                 330

Leu Arg Pro Glu Asp Thr Ala Val Tyr Tyr Cys Ala Arg Ser Pro Ser
     335                 340                 345

```
Gly Phe Asn Arg Gly Gln Gly Thr Leu Val Thr Val Ser Ser
350                 355                 360

<210> SEQ ID NO 2
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Asp Tyr Trp Met Tyr
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Glu Ile Asn Thr Asn Gly Leu Ile Thr Lys Tyr Pro Asp Ser Val Lys
1               5                   10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ser Pro Ser Gly Phe Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Ser Phe Gly Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Ser Ile Ser Gly Ser Gly Ser Asp Thr Leu Tyr Ala Asp Ser Val Lys
1               5                   10                  15

Gly

<210> SEQ ID NO 7
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 7

Gly Gly Ser Leu Ser Arg
1               5

<210> SEQ ID NO 8
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<223> OTHER INFORMATION: This sequence may encompass one to seven
      "Gly Gly Gly Gly Ser" repeating units

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Gly Gly Gly Gly Ser Gly Gly Gly Ser
1               5

<210> SEQ ID NO 10
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<223> OTHER INFORMATION: This sequence may encompass four, five or six
      "Gly Gly Gly Gly Ser" repeating units

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

FORMULATIONS OF SINGLE DOMAIN ANTIGEN BINDING MOLECULES

CROSS REFERENCE TO RELATED APPLICATIONS

This application is a continuation of U.S. Ser. No. 12/608,553, filed on Oct. 29, 2009, and claims priority to U.S. Ser. No. 61/109,474 filed on Oct. 29, 2008, the entire contents of which are hereby incorporated by reference in their entirety. This application also incorporates by reference International Application No. PCT/US2009/062611.

SEQUENCE LISTING

The instant application contains a Sequence Listing which has been submitted via EFS-Web and is hereby incorporated by reference in its entirety. Said ASCII copy, created on Oct. 27, 2009, is named 982855_1.txt, and is 6,456 bytes in size.

BACKGROUND

Advances in biotechnology have made it possible to produce a variety of proteins for pharmaceutical applications using recombinant DNA techniques. Because proteins tend to be larger and more complex than traditional organic and inorganic drugs, the formulation of such proteins poses special problems. For a protein to remain biologically active, a formulation must preserve the conformational integrity of at least a core sequence of the protein's amino acids, while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from, for example, deamidation, racemization, hydrolysis, oxidation, beta elimination or disulfide exchange. Physical instability can result from, for example, denaturation, aggregation, precipitation or adsorption. Three common protein degradation pathways are protein aggregation, deamidation and oxidation (Cleland et al. *Critical Reviews in Therapeutic Drug Carrier Systems* 10(4): 307-377 (1993)).

Freeze-drying is a commonly employed technique for preserving proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage (Pikal, M. Biopharm. 3(9)26-30 (1990) and Arakawa et al. *Pharm. Res.* 8(3):285-291 (1991)).

Therefore, the need still exists for developing protein formulations, particularly for subcutaneous administration, that are stable for long-term storage and delivery.

SUMMARY

The invention relates to formulations of single domain antigen binding molecules (also referred to herein as "SDAB molecules" (e.g., Nanobody™ molecules, in particular formulations of TNF-binding Nanobody™ molecules). The SDAB molecule can include one or more single antigen binding domains that interact with, e.g., bind to, one or more target proteins. The formulations are useful, e.g., as pharmaceutical formulations, for administration to a subject, e.g., a human. Method of preparing, and using the formulations described herein, to treat or prevent, e.g., TNF-associated disorders, are also disclosed.

[Note: Nanobody™ and Nanobodies™ are registered trademarks of Ablynx N.V.]

Accordingly, in one aspect, the invention features a formulation that includes (a) an SDAB molecule, e.g., a Nanobody™ molecule (e.g., a TNF-binding Nanobody™ molecule); (b) a lyoprotectant; (c) (optionally) a surfactant; (d) (optionally) a bulking agent; (e) (optionally) a tonicity adjusting agent; (f) (optionally) a stabilizer; (g) (optionally) a preservative, and (h) a buffer, such that the pH of the formulation is about 5.0 to 7.5. In some embodiments, the formulation is a liquid formulation, a lyophilized formulation, a reconstituted lyophilized formulation, an aerosol formulation, or a bulk storage formulation (e.g., frozen bulk storage formulation). In certain embodiments, the formulation is administered to a subject by injection (e.g., subcutaneous, intravascular, intramuscular or intraperitoneal) or by inhalation.

In certain embodiments, the SDAB molecule, e.g., the Nanobody™ molecule (e.g., the TNF-binding Nanobody™ molecule), in the formulation is at a concentration of about 0.5 mg/mL to about 350 mg/mL, about 0.5 mg/mL to about 300 mg/mL, about 0.5 mg/mL to about 250 mg/mL, about 0.5 mg/mL to about 150 mg/mL, about 1 mg/ml to about 130 mg/mL, about 10 mg/ml to about 130 mg/mL, about 50 mg/ml to about 120 mg/mL, about 80 mg/ml to about 120 mg/mL, about 88 mg/ml to about 100 mg/mL or about 10 mg/ml, about 25 mg/ml, about 50 mg/ml, about 80 mg/ml, about 100 mg/mL, about 130 mg/ml, about 150 mg/ml, about 200 mg/ml, about 250 mg/ml or about 300 mg/ml.

In other embodiments, the lyoprotectant of the formulation is a sugar, e.g., sucrose, sorbitol, or trehalose. For example, the lyoprotectant can be sucrose, sorbitol, or trehalose at a concentration about 2.5% to about 10%, about 5% to about 10%, about 5% to about 8%, or about 4%, about 4.5%, about 5%, about 5.5%, about 6%, about 6.5%, about 7%, about 7.5%, about 8%, about 8.5%, or about 9% (weight/volume).

In yet other embodiments, the buffer in the formulation is a histidine buffer at a concentration about 5 mM to about 50 mM, about 5 mM to about 40 mM, about 5 mM to about 30 mM, about 10 mM to about 20 mM, or about 10 mM, about 20 mM, or about 30 mM. In other embodiments, the buffer in the formulation is a Tris buffer present at a concentration of less than about 5 mM to about 50 mM, about 5 mM to about 40 mM, about 5 mM to about 30 mM, about 10 mM to about 20 mM, or about 10 mM, about 20 mM, or about 30 mM. The pH of the buffers of the formulation is generally between about 5 and 7. In some specific embodiments, the pH of the buffer of the formulation is about 5 to about 7.5, about 5.5 to about 7.2. For example, the pH of the buffer can be about 5, 5.5, 5.8-6.1, 6, 6.1, 6.5 or 7.

In some embodiments, the formulation (optionally) includes a surfactant at a concentration of about 0.001% to 0.6%, e.g., about 0.01% to 0.6%, about 0.1% to 0.6%, about 0.1% to 0.5%, about 0.1% to 0.4%, about 0.1% to 0.3%, about 0.1% to 0.2%, or about 0.01% to 0.02%. In some cases, the formulation contains greater than 0% and up to about 0.6% (e.g., about 0.1% to 0.2% of polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. In specific embodiments, the formulation contains about 0.001%, 0.002%, 0.003%, 0.004%, 0.005%, 0.006%, 0.007%, 0.008%, 0.009%, 0.01% to 0.02%, 0.01%, 0.02%, 0.03%, 0.04%, 0.05%, 0.06%, 0.07%, 0.08%, 0.09%, 0.1%, 0.1% to 0.2%, 0.11%, 0.12%, 0.13%, 0.14%, 0.15%, 0.16%, 0.17%, 0.1.8%, 0.19% or 0.2% of polysorbate-80. Alternatively, the formulation can include poloxamer-188 at about 0.01% to 0.6%, about 0.1% to 0.6%, about 0.1% to 0.5%, about 0.1% to 0.4%, about 0.1% to 0.3%, or about 0.1% to 0.2%.

In certain embodiments, the formulation (optionally) includes a bulking agent, e.g., glycine, at a concentration from about 10 to about 200 mM, from about 25 to about 175 mM, from about 50 to about 150 mM, from about 75 to about 125 mM, or about 100 mM.

In other embodiments, the formulation (optionally) further includes a tonicity adjusting agent, e.g., a molecule that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride.

In yet other embodiments, the formulation (optionally) additionally includes a stabilizer, e.g., a molecule which, when combined with a protein of interest (e.g., the SDAB molecule) substantially prevents or reduces chemical and/or physical instability of the protein of interest in lyophilized, liquid or storage form. Exemplary stabilizers include sucrose, sorbitol, glycine, inositol, sodium chloride, methionine, arginine, and arginine hydrochloride. In certain embodiments, the formulation includes a stabilizer in one or more of the following ranges: Sucrose from about 1% to about 12% (e.g., about 5%, about 7.5%, about 8% or about 10%); sorbitol from about 1% to about 7% (e.g., about 3%, about 4%, about 5%); inositol from about 1% to about 5%; glycine from about 10 mM to about 125 mM (e.g., about 25 mM to 100 mM, about 80 mM, about 90 mM, or about 100 mM); sodium chloride from about 10 mM to 150 mM (e.g., about 25 mM to 100 mM, about 55 mM); methionine from about 10 mM to about 100 mM (e.g., about 10 mM, about 20 mM, about 100 mM); arginine from about 10 mM to about 125 mM (e.g., about 25 mM to about 120 mM, or about 100 mM); arginine hydrochloride from about 10 mM to about 70 mM (e.g., about 10 mM to about 65 mM, or about 55 mM).

In other embodiments, the formulation may further include methionine, at a concentration from about 10 to about 200 mM, from about 25 to about 175 mM, from about 50 to about 150 mM, from about 75 to about 125 mM, or about 100 mM.

In one embodiment, a component of the formulation can function as one or more of a lyoprotectant, a tonicity adjusting agent and/or a stabilizer. For example, depending on the concentration of a component, e.g., sucrose, it can serve as one or more of a lyoprotectant, a tonicity adjusting agent and/or a stabilizer. In other embodiments where several of the components are required in a formulation, different components are used. For example, where the formulation requires a lyoprotectant, a tonicity adjusting agent and a stabilizer, different components are used (e.g., sucrose, glycine and inositol can be used in combination resulting in a combination of a lyoprotectant, a tonicity adjusting agent and a stabilizer, respectively).

In one embodiment, the formulation includes (a) an SDAB molecule, e.g., a Nanobody™ molecule (e.g., a TNF-binding Nanobody™ molecule) at a concentration of about 0.5 to about 300 mg/mL, e.g., at about 1 mg/mL, about 10 mg/mL, about 25 mg/mL, about 50 mg/mL, about 80 mg/mL, about 88 mg/mL, about 100 mg/mL, about 118 mg/mL, about 130 mg/mL, about 150 mg/mL, or about 250 mg/mL; (b) sucrose at a concentration of about 5% to about 10%, e.g., about 5%, about 6%, about 6.5%, about 7%, about 7.5%, about 8%, about 10%; (c) polysorbate-80 at a concentration of about 0 to about 0.6%, e.g., 0.01%, 0.02%, 0.05%, 0.1%, 0.2%, 0.3%, 0.4%, 0.5%, or 0.6%; (d) (optionally) glycine at a concentration of about 0 to about 100 mM, e.g., 100 mM; (e) (optionally) methionine at a concentration of about 0 to about 100 mM, e.g., 100 mM; and (f) a histidine buffer (at a concentration about 10 mM to about 20 mM) or a Tris buffer (at a concentration about 20 mM), such that the pH of the formulation is about 5.0 to 7.5, e.g., 5, 5.5, 5.8-6.1, 6, 6.1, 6.5, or 7.

In one embodiment, the formulation is a liquid formulation. In one representative embodiment, the liquid formulation includes a) an SDAB molecule, e.g., a Nanobody™ molecule (e.g., a TNF-binding Nanobody™ molecule) at a concentration of about 10 to about 150 mg/mL, e.g., about 25 mg/mL, about 50 mg/mL, about 80 mg/mL, about 88 mg/mL, about 100 mg/mL, about 118 mg/mL, about 130 mg/mL; (b) sucrose at a concentration of about 5% to about 10%, e.g, about 7% to about 8%, e.g., 7.5%; or sorbitol from about 1% to about 7% (e.g., about 3%, about 4%, about 5%) (c) polysorbate-80 at a concentration of about, e.g., about 0.01% to 0.02% (e.g., 0.01%); (d) (optionally) glycine at a concentration of about 0 to about 100 mM, e.g., 100 mM; (e) (optionally) methionine at a concentration of about 0 to about 100 mM, e.g., 100 mM; and (f) a histidine buffer (at a concentration about 10 mM to about 20 mM), or a Tris buffer (at a concentration about 20 mM), such that the pH of the formulation is about 5 to 7.5, e.g., 5, 5.5, 5.8-6.1, 6, 6.1, 6.5, or 7. The liquid formulation can be present in an article of manufacture, such as a device, a syringe or a vial with instructions for use. In certain embodiments, the syringe or a vial is composed of glass, plastic, or a polymeric material, such as cyclic olefin polymer or copolymer. In other embodiments, the formulation can be present in an injectable device (e.g., an injectable syringe, e.g., a prefilled injectable syringe). The syringe may be adapted for individual administration, e.g., as a single vial system including an autoinjector (e.g., a pen-injector device), and/or instructions for use. The formulation can be administered to a subject, e.g., a patient, by in injection, e.g., peripheral administration (e.g., subcutaneous, intravascular, intramuscular or intraperitoneal administration).

In other embodiments, the formulation is a lyophilized formulation. In one representative embodiment, the lyophilized formulation includes a) an SDAB molecule, e.g., a Nanobody™ molecule (e.g., a TNF-binding Nanobody™ molecule) at a concentration of about 110 to about 150 mg/mL, e.g., about 25 mg/mL, about 50 mg/mL, about 80 mg/mL, about 88 mg/mL, about 100 mg/mL, about 118 mg/mL, about 130 mg/mL; (b) sucrose at a concentration of about 5% to about 10%, e.g, about 4% to about 7%, e.g., 5%; (c) polysorbate-80 at a concentration of about, e.g., 0.01% to 0.02% (e.g., 0.01%); (d) (optionally) glycine at a concentration of about 0 to about 100 mM, e.g., 100 mM; (e) (optionally) methionine at a concentration of about 0 to about 100 mM, e.g., 100 mM; and (f) a histidine buffer (at a concentration about 10 mM to about 20 mM, e.g., about 20 mM), or a Tris buffer (at a concentration about 20 mM), such that the pH of the formulation is about 5 to 7.5, e.g., 5, 5.5, 5.8-6.1, 6, 6.1, 6.5 or 7. The lyophilized formulation can be reconstituted by mixing the lyophilate with a suitable aqueous composition.

In yet other embodiments, the formulation is a bulk storage formulation. In one representative embodiment, the bulk storage formulation includes a) an SDAB molecule, e.g., a Nanobody™ molecule (e.g., a TNF-binding Nanobody™ molecule) at a concentration of about 80 mg/mL to 300 mg/ml, e.g., about 150 mg/mL, about 175 mg/mL, about 200 mg/mL, about 250 mg/mL, about 275 mg/mL, or about 300 mg/mL; (b) sucrose at a concentration of about 5% to about 10%, e.g, about 4% to about 8%, e.g., 5%, or 7.5%; (c) polysorbate-80 at a concentration of about, e.g., 0.01% to 0.02%; (d) (optionally) glycine at a concentration of about 0 to about 100 mM, e.g., 100 mM; (e) (optionally) methionine at a concentration of about 0 to about 100 mM, e.g., 100 mM; and (f) a histidine buffer (at a concentration about 10 mM to about 20 mM) or a Tris buffer (at a concentration about 20 mM), such that the pH of the formulation is about 5 to 7.5, e.g., 5, 5.5, 5.8-6.1, 6, 6.1, 6.5 or 7. The bulk storage formulation can be frozen. In certain embodiments, the bulk storage formulation can be prepared in large scale, e.g., greater than 10 liters, 50 liters, 100, 150, 200 or more liters.

In certain embodiments, the SDAB molecule, e.g., the Nanobody™ molecule (e.g., the TNF-binding Nanobody™ molecule) of the formulation includes one or more single binding domains (e.g., one or more Nanobodies™). For example, the Nanobody™ molecule can comprise, or consist of, a polypeptide, e.g., a single chain polypeptide, comprising at least one immunoglobulin variable domain (including one, two or three complementarity determining regions (CDRs)). Examples of SDAB molecules include molecules naturally devoid of light chains (e.g., VHH, Nanobodies™, or camelid derived antibodies). Such SDAB molecules can be derived or obtained from camelids such as camel, llama, dromedary, alpaca and guanaco. In other embodiments, the SDAB molecule may include single domain molecules including, but not limited to, other naturally-occurring single domain molecules, such as shark single domain polypeptides (IgNAR); and single domain scaffolds fibronectin scaffolds). Single domain molecules may be derived from shark.

In one embodiment, the SDAB molecule of the formulation is a single chain polypeptide comprised of one or more single domain molecules. In embodiments, the Nanobody™ molecule is monovalent or multivalent (e.g., bivalent, trivalent, or tetravalent). In other embodiments, the Nanobody™ molecule is monospecific or multispecific (e.g., bispecific, trispecific or tetraspecific). The SDAB molecule may comprise one or more single domain molecules that are recombinant, CDR-grafted, humanized, camelized, de-immunized, and/or in vitro generated (e.g., selected by phage display). For example, the SDAB molecule can be a single chain fusion polypeptide comprising one or more single domain molecules that bind to one or more target antigens. Typically, the target antigen is a mammalian, e.g., a human, protein. In certain embodiments, the SDAB molecule binds to a serum protein, e.g., a human serum proteins chosen from one or more of serum albumin (human serum albumin (HSA)), fibrin, fibrinogen, or transferrin.

In one exemplary embodiment, the SDAB molecule of the formulation is a trivalent, bispecific molecule composed of a single chain polypeptide fusion of two single domain molecules (e.g., two camelid variable regions) that bind to a target antigen, e.g., tumor necrosis factor α (TNF α), and one single domain molecule (e.g., a camelid variable region) that binds to a serum protein, e.g., HSA. The single domain molecules of the SDAB molecule can be arranged in the following order from N- to C-terminus: TNFα-binding single domain molecule—HSA-binding single domain molecule—TNFα-binding single domain molecule. It will be appreciated that any order or combination of single domain molecules against one or more targets can be formulated as described herein.

In one embodiment, the SDAB molecule of the formulation is referred to herein as "ATN-103," comprises, or consists of, the amino acid sequence shown in FIG. 30 (SEQ ID NO:1), or an amino acid sequence substantially identical thereto (e.g., an amino acid sequence at least 85%, 90%, 95% or more identical to, or having up to 20, 15, 10, 5, 4, 3, 2, 1 amino acid changes (e.g., deletions, insertions or substitutions (e.g., conservative substitutions) relative to the amino acid sequence shown in FIG. 30). Examples of additional trivalent, bispecific Nanobody™ molecules that can be formulated as described herein include TNF24, TNF25, TNF26, TNF27, TNF28, TNF60 and TNF62 disclosed in Table 29 of WO 2006/122786.

In certain embodiments, at least one of the single domain molecule of the SDAB molecule of the formulation binds to TNFα includes one, two, or three CDRs having the amino sequence: DYWMY (SEQ ID NO:2) (CDR1), EINTNGLITKYPDSVKG (SEQ ID NO:3) (CDR2) and/or SPSGFN (SEQ ID NO:4) (CDR3), or having a CDR that differs by fewer than 3, 2 or 1 amino acid substitutions (e.g., conservative substitutions) from one of said CDRs. In other embodiments, the single domain molecule comprises a variable region having the amino acid sequence from about amino acids 1 to 115 of FIG. 30, or an amino acid sequence substantially identical thereto (e.g., an amino acid sequence at least 85%, 90%, 95% or more identical to, or having up to 20, 15, 10, 5, 4, 3, 2, 1 amino acid changes (e.g., deletions, insertions or substitutions (e.g., conservative substitutions) relative to the amino acid sequence shown in FIG. 30). In embodiments, the TNFα-binding single domain molecule has one or more biological activities of the TNFα-binding single domain antibody molecule shown in FIG. 30. For example, the TNFα-binding single domain molecule binds to the same or a similar epitope as the epitope recognized by the TNFα-binding single domain molecule shown in FIG. 30 (e.g., binds to TNFα in its trimeric form; binds to the TNFα site contacting the TNF receptor; binds to an epitope in the TNFα trimer comprising Gln at position 88 and Lys at position 90 on the first TNF monomer (monomer A), and Glu at position 146 on the second TNF monomer (monomer B), or an epitope as disclosed in WO 06/122786). In other embodiment, the TNFα-binding single domain molecule has an activity (e.g., binding affinity, dissociation constant, binding specificity, TNF-inhibitory activity) similar to any of the TNFα-binding single domain molecule disclosed in WO 06/122786.

In other embodiments, the TNFα-binding Nanobody™ molecule comprises one or more of the Nanobodies™ disclosed in WO 2006/122786. For example, the TNFα-binding Nanobody™ molecule can be a monovalent, bivalent, trivalent TNFα-binding Nanobody™ molecule disclosed in WO 2006/122786. Exemplary TNFα-binding Nanobodies™ include, but are not limited to, TNF1, TNF2, TNF3, humanized forms thereof (e.g., TNF29, TNF30, TNF31, TNF32, TNF33). Additional examples of monovalent TNFα-binding Nanobodies™ are disclosed in Table 8 of WO 2006/122786. Exemplary bivalent TNFα-binding Nanobody™ molecules include, but are not limited to, TNF55 and TNF56, which comprise two TNF30 Nanobodies™ linked via a peptide linker to form a single fusion polypeptide (disclosed in WO 2006/122786). Additional examples of bivalent TNFα-binding Nanobody™ molecules are disclosed in Table 19 of WO 2006/122786 as TNF4, TNF5, TNF6, TNF7, TNF8).

In other embodiments, at least one of the single domain molecule of the SDAB molecule of the formulation binds to HSA includes one, two, or three CDRs having the amino sequence: SFGMS (SEQ ID NO:5) (CDR1), SISGSGSDT-LYADSVKG (SEQ ID NO:6) (CDR2) and/or GGSLSR (SEQ ID NO:7) (CDR3), or having a CDR that differs by fewer than 3, 2 or 1 amino acid substitutions (e.g., conservative substitutions) from one of said CDRs. In other embodiments, the single domain molecule comprises a variable region having the amino acid sequence from about amino acids 125 to 239 of FIG. 30 (SEQ ID NO:1), or an amino acid sequence substantially identical thereto (e.g., an amino acid sequence at least 85%, 90%, 95% or more identical to, or having up to 20, 15, 10, 5, 4, 3, 2, 1 amino acid changes (e.g., deletions, insertions or substitutions (e.g., conservative substitutions) relative to the amino acid sequence shown in FIG. 30 (SEQ ID NO:1)). In embodiments, the HSA-binding single domain molecule has one or more biological activities of the HSA-binding single domain molecule shown in FIG. 30 (SEQ ID NO:1). For example, the HSA-binding single domain molecule binds to the same or a similar epitope as the epitope recognized by the HSA-binding single domain molecule shown in FIG. 30 (SEQ ID NO:1). In other embodiment, the HSA-binding single domain molecule has an activity (e.g., binding affinity, dissociation constant, binding specificity) similar to any of the HSA-binding single domain molecule disclosed in WO 06/122786.

In other embodiments, the HSA-binding SDAB molecule comprises one or more of the Nanobodies™ disclosed in WO 2006/122786. For example, the HSA-binding SDAB molecule can be a monovalent, bivalent, trivalent HSA-binding Nanobody™ molecule disclosed in WO 2006/122786. In other embodiments, the HSA-binding SDAB molecule can be a monospecific or a multispecific molecule having at least one of the binding specificities bind to HSA. Exemplary TNFα-binding Nanobodies™ include, but are not limited to, ALB1, humanized forms thereof (e.g., ALB6, ALB7ALB8, ALB9, ALB10), disclosed in WO 06/122786.

In other embodiments, two or more of the single domain molecules of the SDAB molecules are fused, with or without a linking group, as a genetic or a polypeptide fusion. The linking group can be any linking group apparent to those of skill in the art. For instance, the linking group can be a biocompatible polymer with a length of 1 to 100 atoms. In one embodiment, the linking group includes or consists of polyglycine, polyserine, polylysine, polyglutamate, polyisoleucine, or polyarginine residues, or a combination thereof. For example, the polyglycine or polyserine linkers can include at least five, seven eight, nine, ten, twelve, fifteen, twenty, thirty, thirty-five and forty glycine and serine residues. Exemplary linkers that can be used include Gly-Ser repeats, for example, (Gly)$_4$-Ser (SEQ ID NO: 8) repeats of at one, two, three, four, five, six, seven or more repeats. In embodiments, the linker has the following sequences: (Gly)$_4$-Ser-(Gly)$_3$-Ser (SEQ ID NO: 9) or ((Gly)$_4$-Ser)n (SEQ ID NO: 10), where n is 4, 5, or 6.

The formulations of the invention can include a SDAB molecule that is modified by associating, e.g., covalently or non-covalently a second moiety. For example, the Nanobody™ molecule can be covalently attached to a suitable pharmacologically acceptable polymer, such as poly(ethyleneglycol) (PEG) or a derivative thereof (such as methoxy-poly(ethyleneglycol) or mPEG). Examples of pegylated Nanobody™ molecules are disclosed as TNF55-PEG40, TNF55-PEG60, TNF56-PEG40 and TNF56-PEG60 in WO 06/122786.

In another embodiment, the formulations of the invention are stable for at least 3, 6, 9, 12 months (e.g., at least 24, 30, 36 months), at a temperature of about 2° C. to about 25° C. (e.g., about 4° C. or 25° C.). In certain embodiments, the integrity of the SDAB molecule is maintained after storage in the formulation for at least at least 3, 6, 9, 12 months (e.g., at least 24, 30, 36 months), at a temperature of about 2° C. to about 25° C. (e.g., about 4° C. or 25° C.). For example, the SDAB molecule in the formulation retains at least 50%, 70%, 75%, 80%, 85%, 90%, 95%, 98% or up to 100% of a biological activity, e.g., binding activity, of the SDAB molecule after storage at a temperature of about 2° C. to about 25° C. (e.g., about 4° C. or 25° C.). In some embodiments, the formulation includes less than 10%, 9%, 5%, 4%, 3%, 2%, 1% or less high molecular weight (HMW) species after storage in the formulation for at least at least 3, 6, 9, 12 months (e.g., at least 24, 30, 36 months), at a temperature of about 2° C. to about 25° C. (e.g., about 4° C. or 25° C.). In other embodiments, the formulation includes less than 10%, 9%, 5%, 4%, 3%, 2%, 1% or less low molecular weight (HMW) species after storage in the formulation for at least at least 3, 6, 9, 12 months (e.g., at least 24, 30, 36 months), at a temperature of about 2° C. to about 25° C. (e.g., about 4° C. or 25° C.). In yet other embodiments, the formulation includes less than 10%, 9%, 8%, 7%, 6%, 5%, 4%, 3%, 2%, 1% or less acidic species after storage in the formulation for at least at least 3, 6, 9, 12 months (e.g., at least 24, 30, 36 months), at a temperature of about 2° C. to about 25° C. (e.g., about 4° C. or 25° C.). In yet other embodiments, the formulation includes less than 10%, 9%, 8%, 7%, 6%, 5%, 4%, 3%, 2%, 1% or less basic species after storage in the formulation for at least at least 3, 6, 9, 12 months (e.g., at least 24, 30, 36 months), at a temperature of about 2° C. to about 25° C. (e.g., about 4° C. or 25° C.). The HMW, LMW, acidic and basic species can be detected in the formulations using standard techniques, such as size exclusion-high performance liquid chromatography (SEC-HPLC) and the like as described herein.

In some embodiments, upon reconstitution of the lyophilized SDAB formulation, the formulation retains at least 80%, 90%, 95% or higher of the SDAB structure compared to the formulation prior to lyophilization. SDAB structure is determined, for example, by binding assay, bioassay, or the ratio of HMW species to LMW species.

The formulations of the invention can also include a second agent, e.g., a second therapeutically or pharmacologically active agent that is useful in treating a TNF-α associated disorder, e.g., inflammatory or autoimmune disorders, including, but not limited to, rheumatoid arthritis (RA) (e.g., moderate to severe rheumatoid arthritis), arthritic conditions (e.g., psoriatic arthritis, polyarticular juvenile idiopathic arthritis (JIA), ankylosing spondylitis (AS), psoriasis, ulcerative colitis, Crohn's disease, inflammatory bowel disease, and/or multiple sclerosis. For example, the second agent may be an anti-TNF antibody or TNF binding fragment thereof, wherein the second TNF antibody binds to a different epitope than the TNF-binding SDAB molecule of the formulation. Other non-limiting examples of agents that can be co-formulated with the TNF-binding SDAB molecule include, but are not limited to, a cytokine inhibitor, a growth factor inhibitor, an immunosuppressant, an anti-inflammatory agent, a metabolic inhibitor, an enzyme inhibitor, a cytotoxic agent, and a cytostatic agent. In one embodiment, the additional agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Arava®), tumor necrosis factor inhibitors, including etanercept (Enbrel®), infliximab (Remicade®) (with or without methotrexate), and adalimumab (Humira®), anti-CD20 antibody (e.g., Rituxan®), soluble interleukin-1 receptor, such as anakinra (Kineret®), gold, minocycline (Minocin®), penicilllamine, and cytotoxic agents, including azathioprine, cyclophosphamide, and cyclosporine. Such combination therapies may advantageously utilize lower dosages of the administered therapeutic agents, thus avoiding possible toxicities or complications associated with the various monotherapies.

Alternative combination of excipients and/or second therapeutic agents can be identified and tested followed the guidance provided herein.

In yet another embodiment, the formulations described herein are suitable for administration to a subject, e.g., a human subject (e.g., a patient having a TNFα associated disorder). The formulation can be administered to the subject by injection (e.g., subcutaneous, intravascular, intramuscular or intraperitoneal) or by inhalation.

In another aspect, the invention features a method or process of preparing the formulations described herein. The method or process includes: expressing the SDAB molecule in a cell culture; purifying the SDAB molecule, e.g., by passing the SDAB molecule through at least one of a chromatography purification step, an ultrafiltration/diafiltration steps; adjusting the concentration of the SDAB molecule, e.g., to about 10 to 250 mg/mL in a formulation containing a lyoprotectant, a surfactant and a buffer as described herein, e.g., sucrose at a concentration of about 5% to about 10%, e.g., about 5%, about 10%; polysorbate-80 at a concentration of about 0 to about 0.02%, e.g., 0.01%, 0.02%; (optionally) glycine at a concentration of about 0 to about 100 mM, e.g., 100 mM; (optionally) methionine at a concentration of about 0 to about 100 mM, e.g., 100 mM; and (f) a Histidine (at a concentration about 10 to about 20 mM) or a Tris buffer (at a concentration about 20 mM), such that the pH of the formulation is about 5 to 7.5, e.g., 5, 5.5, 5.8-6.1, 6, 6.1, 6.5 or 7.

In another aspect, the invention features a method or process for preparing a reconstituted formulation containing an SDAB molecule, e.g., a TNF-binding SDAB molecule as described herein. The method includes: lyophilizing a mixture of an SDAB molecule, lyoprotectant, a surfactant and a buffer, thereby forming a lyophilized mixture; and reconstituting the lyophilized mixture in a diluent, thereby preparing a formulation as described herein. In one embodiment, the formulation includes (a) a SDAB molecule, e.g., a TNF-binding Nanobody™ molecule at a concentration of about 0.5 to about 200 mg/mL, e.g., at about 1 mg/mL, about 50 mg/mL, about 80 mg/mL, about 88 mg/mL, about 100 mg/mL, about 118 mg/mL; (b) sucrose at a concentration of about 5% to about 10%, about 5%, about 10%; c) polysorbate-80 at a concentration of about 0 to about 0.02%, e.g., 0.01%, 0.02%; (d) (optionally) glycine at a concentration of about 0 to about 100 mM, e.g., 100 mM; (e) (optionally) methionine at a concentration of about 0 to about 100 mM, e.g., 100 mM; and (f) a Histidine (at a concentration about 10 to about 20 mM) or a Tris buffer (at a concentration about 20 mM), such that the pH of the formulation is about 5 to 7.5, e.g., 5, 5.5, 5.8-6.1, 6, 6.1, 6.5 or 7.

In another aspect, the invention relates to a method for treating or preventing in a subject (e.g., a human subject) a TNFα associated disorder, e.g., inflammatory or autoimmune disorders, including, but not limited to, rheumatoid arthritis (RA) (e.g., moderate to severe rheumatoid arthritis), arthritic conditions (e.g., psoriatic arthritis, polyarticular juvenile idiopathic arthritis (JIA), ankylosing spondylitis (AS), psoriasis, ulcerative colitis, Crohn's disease, inflammatory bowel disease, and/or multiple sclerosis. The method includes administering to a subject, e.g., a human patient, a pharmaceutical composition includes a TNF-binding SDAB formulation as described herein, e.g., a formulation containing a TNF-binding SDAB molecule, alone or in combination with any of the combination therapies described herein, in an amount such that one or more of the symptoms of the TNFα associated disorder are reduced.

In another aspect, the invention features a kit or an article of manufacture that includes a device, a syringe or a vial containing the formulations described herein. The kit or article may optionally include instructions for use. In certain embodiments, the syringe or a vial is composed of glass, plastic, or a polymeric material, such as cyclic olefin polymer or copolymer. In other embodiments, the formulation can be present in an injectable device (e.g., an injectable syringe, e.g., a prefilled injectable syringe). The syringe may be adapted for individual administration, e.g., as a single vial system including an autoinjector (e.g., a pen-injector device), and/or instructions for use. In one embodiment, the injectable device is a prefilled pen or other suitable autoinjectable device, optionally with instruction for use and administration.

In certain embodiments, the kit or article of manufacture (e.g., the prefilled pen or syringe with a single or multiple dose unit) is provided to a subject, e.g., a patient or a healthcare provider, prepackaged with instructions for administration (e.g., self-administration) by injection (e.g., subcutaneous, intravascular, intramuscular or intraperoneal).

In other embodiments, the invention features, a device for nasal, transdermal, intravenous administration of the formulations described herein is provided. For example, a transdermal patch for administration of the formulations described herein is provided. In yet other cases, an intravenous bag for administration of the formulations described herein is provided. In embodiments, the intravenous bag is provided with normal saline or 5% dextrose.

In another aspect, the invention features a method of instructing a patient (e.g., a human patient) in need of an SDAB molecule, e.g., a TNFα Nanobody™ molecule, how to administer a formulation described herein. The method includes: (i) providing the patient with at least one unit dose of a formulation of the SDAB molecule described herein; and (ii) instructing the patient to self-administer the at least one unit dose, e.g., by injection (e.g., subcutaneous, intravascular, intramuscular or intraperitoneal). In one embodiment, the patient has a TNFα associated disorder, e.g., inflammatory or autoimmune disorders as described herein.

In another aspect, the invention features a method of instructing a recipient on the administration of a formulation of TNFα Nanobody™ molecule described herein. The method includes instructing the recipient (e.g., an end user, patient, physician, retail or wholesale pharmacy, distributor, or pharmacy department at a hospital, nursing home clinic or HMO) how the formulation should be administered to a patient.

In another aspect, a method of distributing a formulation of an SDAB molecule, e.g., a TNFα Nanobody™ molecule, described herein is provided. The method includes providing a recipient (e.g., an end user, patient, physician, retail or wholesale pharmacy, distributor, or pharmacy department at a hospital, nursing home clinic or HMO) with a package containing sufficient unit dosages of the SDAB molecule, e.g., a TNFα Nanobody™ molecule, to treat a patient for at least 6, 12, 24, or 36 months.

In another aspect, the invention features a method or process of evaluating the quality of a package or lot of packages (e.g., to determine if it has expired) of a formulation described herein containing a SDAB molecule, e.g., a TNFα Nanobody™ molecule. The method includes evaluating whether the package has expired. The expiration date is at least 6, 12, 24, 36, or 48 months, e.g., greater than 24 or 36 months, from a preselected event, such as manufacturing, assaying, or packaging. In some embodiments, a decision or step is taken as a result of the analysis, e.g., the SDAB molecule in the package is used or discarded, classified, selected, released or withheld, shipped, moved to a new location, released into commerce, sold, or offered for sale, withdrawn from commerce or no longer offered for sale, depending on whether the product has expired.

In another aspect, the invention features a method of storing, distributing, or using a formulation of an SDAB molecule, e.g., a TNF Nanobody™ molecule, described herein. The method includes: storing the formulation for period at a given temperature, e.g., less than 25° C., e.g., below freezing or below 15° C., 10° C., or 4° C. In embodiments, the method further includes providing the formulation to a recipient, e.g., an end-user, e.g., a patient or healthcare provider, for storage under the similar or different conditions (e.g., a higher temperature than the first storage period). The formulation can be a liquid, lyophilized or reconstituted formulation.

In another aspect, the invention features a method of analyzing a product or a process, e.g., a manufacturing process. The method includes providing a formulation of an SDAB molecule, e.g., a TNF Nanobody™ molecule, as described herein, and assessing a parameter of the formulation, such as color (e.g., colorless to slightly yellow, or colorless to yellow), clarity (e.g., clear to slightly opalescent or clear to opalescent), or viscosity (e.g., between approximately 1 to 5 cP when measured at ambient temperature, such as at 20° C.-30° C., e.g., 25° C.), amount of one or more HMW, LMW, acidic and/or basic species, as described herein. The evaluation can include an assessment of one or more parameters. Optionally, a determination of whether the parameter meets a preselected criteria is determined, e.g., whether the preselected criteria is present, or is present in a preselected range, is determined, thereby analyzing the process.

In one embodiment, evaluation of the process includes a measure of the stability of the SDAB molecule formulation. Stability of the antibody formulation can be measured, for example, by aggregate formation, which is assayed, e.g., by size exclusion high pressure liquid chromatography (SE-HPLC), by color, clarity, or viscosity as described herein. A formulation can be determined to be stable, and therefore acceptable for further processing or distribution, if the change in an assay parameter is less than about 10%, 5%, 3%, 2%, 1%, 0.5%, 0.05%, or 0.005% or less, over a pre-set period of time, and optionally at a given temperature.

In one embodiment, the method further includes comparing the value determined with a reference value, to thereby analyze the manufacturing process.

In one embodiment, the method further includes maintaining the manufacturing process based, at least in part, upon the analysis. In one embodiment, the method further includes altering the manufacturing process based upon the analysis.

In another embodiment the method includes evaluating a process, e.g., manufacturing process, of a formulation of an SDAB molecule, e.g., a TNF Nanobody™ molecule, made by a selected process, that includes making a determination about the process based upon a method or analysis described herein. In one embodiment, the method further includes maintaining or altering the manufacturing process based, at least in part, upon the method or analysis. Thus, in another embodiment the party making the evaluation does not practice the method or analysis described herein but merely relies on results which are obtained by a method or analysis described herein.

In another embodiment the method includes comparing two or more preparations in a method of monitoring or controlling batch-to-batch variation or to compare a preparation to a reference standard.

In yet another embodiment, the method can further include making a decision, e.g., to classify, select, accept or discard, release or withhold, process into a drug product, ship, move to a different location, formulate, label, package, release into commerce, sell or offer for sale the preparation, based, at least in part, upon the determination.

In another aspect, the invention features a method of evaluating the quality of a formulation of an SDAB molecule, e.g., a TNF Nanobody™ molecule, as described herein, e.g., in a quality control or release specification analysis. The method includes providing an evaluation of an SDAB molecule formulation for a parameter, such as color (e.g., colorless to slightly yellow, or colorless to yellow), clarity (e.g., clear to slightly opalescent or clear to opalescent), or viscosity (e.g., between approximately 1 to 5 cP when measured at ambient temperature, such as at 20° C. to 30° C., e.g., 25° C.). The evaluation can include an assessment of one or more of the above parameters. The method also includes, optionally, determining whether the solution parameter meets a preselected criteria, e.g., whether the preselected criteria is present, or is present in a preselected range. If the observed solution parameter is within a preselected range of values, or meets the preselected standard criteria, then the preparation is selected, such as for packaging, use, sale, release into commerce, discarding etc.

In another aspect, the invention features a method of complying with a regulatory requirement, e.g., a post approval requirement of a regulatory agency, e.g., the FDA. The method includes providing an evaluation of an antibody formulation for a parameter, as described herein. The post approval requirement can include a measure of one more of the above parameters. The method also includes, optionally, determining whether the observed solution parameter meets a preselected criteria or if the parameter is in a preselected range; optionally, memorializing the value or result of the analysis, or communicating with the agency, e.g., by transmitting the value or result to the regulatory agency.

In another aspect, the invention features a method of making a batch of a formulation of an SDAB molecule, e.g., a TNF Nanobody™ molecule, having a preselected property, e.g., meeting a release specification, label requirement, or compendial requirement, e.g., a property described herein. The method includes providing a test formulation; analyzing the test formulation according to a method described herein; determining if the test formulation satisfies a preselected criteria, e.g., having preselected relationship with a reference value, e.g., one or more reference values disclosed herein, and selecting the test antibody preparation to make a batch of product.

In another aspect, the invention features multiple batches of a formulation of an SDAB molecule, e.g., a TNF Nanobody™ molecule, wherein one or more parameters (e.g., a value or solution parameter determined by a method described herein), for each batch varies less than a preselected range from a pre-selected desired reference value or criteria, e.g., a range or criteria described herein. In some embodiments, one or more parameters for one or more batches of formulation, is determined and a batch or batches selected as a result of the determination. Some embodiments include comparing the results of the determination to a preselected value or criteria, e.g., a reference standard. Other embodiments include adjusting the dose of the batch to be administered, e.g., based on the result of the determination of the value or parameter.

In another aspect, the invention features a method of one or more of: providing a report to a report-receiving entity, evaluating a sample of a formulation of an SDAB molecule, e.g., a TNF Nanobody™ molecule, for compliance with a reference standard, e.g., an FDA requirement, seeking indication from another party that a preparation of the SDAB molecule meets some predefined requirement, or submitting information about a preparation of an SDAB molecule to another party. Exemplary receiving entities or other parties include a government, e.g., the U.S. federal government, e.g., a government agency, e.g., the FDA. The method includes one or more (or all) of the following steps for making and/or testing an aqueous formulation of SDAB molecule in a first country, e.g., the U.S.; sending at least an aliquot of the sample outside the first country, e.g., sending it outside the United States, to a second country; preparing, or receiving, a report which includes data about the structure of the preparation of the SDAB molecule, e.g., data related to a structure and/or chain described herein, e.g., data generated by one or more of the methods described herein; and providing said report to a report recipient entity.

In one embodiment, the report-receiving entity can determine if a predetermined requirement or reference value is met by the data and, optionally, a response from the report-receiving entity is received, e.g., by a manufacturer, distributor or seller of a formulation of an SDAB molecule. In one embodiment, upon receipt of approval from the report recipient entity, the preparation of a formulation of an SDAB molecule is selected, packaged, or placed into commerce.

In another aspect, the invention features a method of evaluating a formulation of an SDAB molecule. The method includes receiving data with regard to the presence or level of an SDAB molecule, e.g., wherein the data was prepared by one or more methods described herein; providing a record which includes said data and optionally includes an identifier for a batch of SDAB molecule; submitting said record to a decision-maker, e.g., a government agency, e.g., the FDA; optionally, receiving a communication from said decision maker; optionally, deciding whether to release or market the batch of SDAB molecule based on the communication from the decision maker. In one embodiment, the method further includes releasing the sample.

All publications, patent applications, patents, and other references mentioned herein are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting.

Other features and advantages of the invention will be apparent from the detailed description, drawings, and from the claims.

DESCRIPTION OF THE DRAWINGS

FIG. 30 depicts the amino acid sequence of ATN-103 polypeptide chain (SEQ ID NO:1).

DETAILED DESCRIPTION

Figure 1:
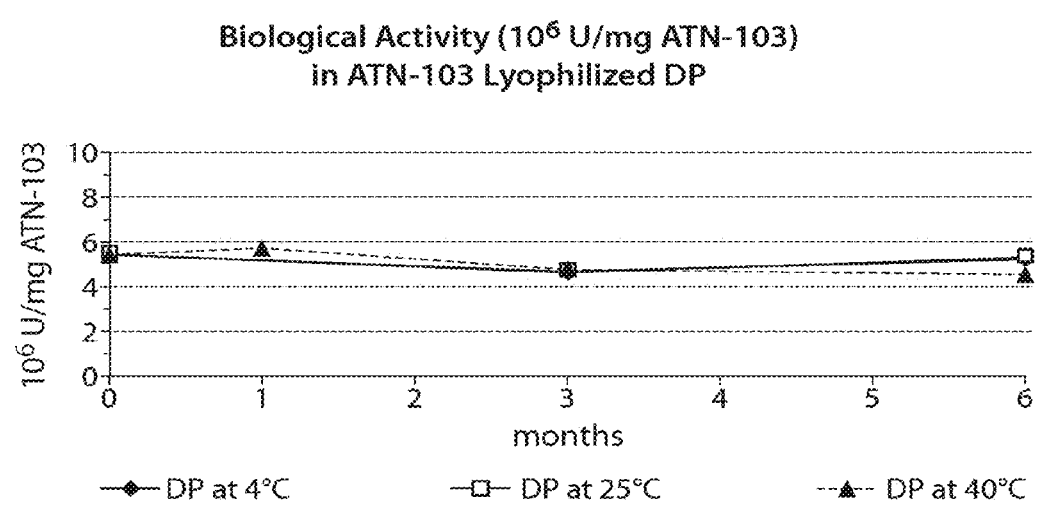
FIG. 1 depicts the results of the biological activity of a lyophilized formulation of $10^6$ U/mg of TNF-binding Nanobody™ (ATN-103) stored as a dried powder (DP) preparation for up to six months. The formulation was stored at the indicated temperatures.

Stable formulations that include an SDAB molecule, e.g., a Nanobody™ molecule (e.g., a TNF-binding Nanobody™ molecule), have been identified that are suitable for storage of high and low concentrations of the SDAB molecule (a "formulation"). The SDAB molecule which is formulated is preferably essentially pure and desirably essentially homogeneous (i.e. free from contaminating proteins etc). "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

The integrity of the SDAB molecule in the formulation is generally maintained following long-term storage as a liquid or as a lyophilized product under various conditions. For example, the integrity of the SDAB molecule is adequately maintained after exposure to a wide range of storage temperatures (e.g., −80° C. to 40° C.), shear stress (e.g., shaking) and interfacial stress (freeze-thaw cycles).

Additionally, for lyophilized material, the integrity of the SDAB molecule is adequately maintained during the process of reconstitution. In addition, SDAB molecule integrity is sufficiently maintained for use as a medicament as demonstrated by relatively low accumulations of LMW species and HMW species, bioactivity in vitro, binding activity in vitro, after long term storage (e.g., up to 12 months) at various temperatures (e.g., −80° C. to 40° C.).

In order that the present invention may be more readily understood, certain terms are first defined. Additional definitions are set forth throughout the detailed description.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

The terms "proteins" and "polypeptides" are used interchangeably herein.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

A "stable" formulation of an SDAB molecule exhibits little or no signs of any one or more of aggregation, fragmentation, deamidation, oxidation, or change in biological activity over an extended period of time, e.g., 6, 12 months, 24 months, 36 months or longer. For example, in one embodiment, less than 10% of the SDAB molecule is aggregated, fragmented, or oxidized. Aggregation, precipitation, and/or denaturation can be assessed by known methods, such as visual examination of color and/or clarity, or by UV light scattering or size exclusion chromatography. The ability of the protein to retain its biological activity can be assessed by detecting and quantifying chemically altered forms of the antibody. Size modification (e.g., clipping), which can be evaluated using size exclusion chromatography, and/or SDS-PAGE, for example. Other types of chemical alteration include charge alteration (e.g., occurring as a result of deamidation), which can be evaluated by ion-exchange chromatography, for example.

An SDAB molecule "retains its biological activity" in a pharmaceutical formulation, if the biological activity of the molecule at a given time is within about 50% or higher of the biological activity exhibited at the time the pharmaceutical formulation was prepared as determined in an antigen binding assay, for example.

A "reconstituted" formulation is one which has been prepared by dissolving a lyophilized protein formulation in a diluent such that the protein is dispersed in the reconstituted formulation. The reconstituted formulation in suitable for administration (e.g. parenteral or peripheral administration) to a patient to be treated with the protein of interest and, in certain embodiments of the invention, may be one which is suitable for subcutaneous administration.

By "isotonic" or "iso-osmotic" is meant that the formulation of interest has similar or essentially the same osmotic pressure as human blood. Isotonic or iso-osmotic formulations will generally have an osmotic pressure from about 250 to 350 mOsm. Isotonicity can be measured using a vapor pressure or ice-freezing type osmometer, for example.

A "tonicity adjusting agent" refers to a compound that renders the formulation substantially isotonic or iso-osmotic with human blood. Exemplary tonicity adjusting agents are: sucrose, sorbitol, glycine, methionine, mannitol, dextrose, inositol, sodium chloride, arginine, or arginine hydrochloride. Typically, tonicity adjusting agents are added in an amount such that the overall formulation exerts an osmotic strength similar to that of human blood. For example, human blood contains approximately 300 mM solutes. Typically, pharmaceutical products target a total molarity of 300 mM. This corresponds to an osmotic pressure of approximately 300 to 310 mOsm, with a typical range of 250 mOsm to 350 mOsm. The amount of tonicity adjusting agent required can be initially estimated via calculation. The contribution to total molarity can be estimated from molecular weight of the excipient molecule, and known properties of the molecule, e.g. does the molecule dissociate into two ionic species, or is the molecule non-ionic (does not dissociate). Additionally, it is necessary to understand the osmotic contribution of the specific protein molecule as a function of protein concentration. This parameter can be determined experimentally.

For example, starting with a formulation (not tonicity corrected) of 10 mM histidine, 5% sucrose, 0.01% polysorbate 80, with an anti-TNF Nanobody™ protein concentration of 100 mg/mL, as a first step, the estimated molarity of the starting formulation can be calculated as follows:

10 mM histidine=10 mM
5% sucrose corresponds to approximately 146 mM

5%=5 g/100 mL=50 g/L→(50 g/L)/(342.3 g/mol)= 0.146 mol/L=146 mM 0.01% polysorbate 80 exerts essentially zero molarity and can be disregarded.
100 mg/mL protein: It has been determined through experimentation that 100 mg/mL anti-TNF Nanobody™ protein exerts an osmotic pressure that corresponds to approximately 48 mM.

Therefore, summing all contributions to molarity in the initial formulation:

10 mM+146 mM+48 mM=204 mM

If the target molarity is 310 mM, then the corresponding amount molarity to make up the remainder of the target is:

310 mM−204 mM=106 mM

Thus, the recommended amount of tonicity adjusting agent is 106 mM of a non-ionic tonicity adjusting agent, or 53 mM of an ionic tonicity adjusting agent that completely dissociates into two ionic species.

After the initial estimate of tonicity adjusting agent is determined, it is recommended to test the formulation experimentally. Thus, in the example provided, 100 mM glycine was added to the initial formulation. (The recommended 106 mM was rounded down to 100 mM for simplicity). The expected osmolarity would be:

10 mM histidine+146 mM sucrose+48 mM protein+ 100 mM glycine=304 mM

The experimental osmotic pressure value of the formulation=305 mOsm.

A "lyoprotectant" is a molecule which, when combined with a protein of interest, significantly prevents or reduces chemical and/or physical instability of the protein upon lyophilization and subsequent storage. Exemplary lyoprotectants include sugars such as sucrose, sorbitol, or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; and combinations thereof. Typically, the lyoprotectant is a non-reducing sugar, such as trehalose or sucrose. The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

A "stabilizer" refers to a molecule which, when combined with a protein of interest (e.g., the SDAB molecule) substantially prevents or reduces chemical and/or physical instability of the protein of interest in lyophilized, reconstituted, liquid or storage form. Exemplary stabilizers include sucrose, sorbitol, glycine, inositol, sodium chloride, methionine, arginine, and arginine hydrochloride.

The "diluent" of interest herein is one which is pharmaceutically acceptable (safe and non-toxic for administration to a human) and is useful for the preparation of a reconstituted formulation. Exemplary diluents include sterile water, bacteriostatic water for injection (BWFI), a pH buffered solution phosphate-buffered saline), sterile saline solution, Ringer's solution or dextrose solution.

A "preservative" is a compound which can be added to the diluent to essentially reduce bacterial action in the reconstituted formulation, thus facilitating the production of a multi-use reconstituted formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "bulking agent" is a compound which adds mass to the lyophilized mixture and contributes to the physical structure of the lyophilized cake (e.g. facilitates the production of an essentially uniform lyophilized cake which maintains an open pore structure). Exemplary bulking agents include mannitol, glycine, polyethylene glycol and xorbitol.

The methods and compositions of the present invention encompass polypeptides and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences containing a common structural domain having at least about 85%, 90%, 91%, 92%, 93%, 94%, 95%, 96%, 97%, 98% or 99% identity to a reference sequence. In other embodiments, the amino acid sequence can contain one or more amino acid insertions, deletions, or substitutions (e.g., conservative substitutions) to arrive at a percentage identity of at least about 85%, 90%, 91%, 92%, 93%, 94%, 95%, 96%, 97%, 98% or 99% identity to a reference sequence In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%, 91%, 92%, 93%, 94%, 95%, 96%, 97%, 98% or 99% identity to a reference sequence.

Also included as polypeptides of the present invention are fragments, derivatives, analogs, or variants of the foregoing polypeptides, and any combination thereof. The terms "fragment," "variant," "derivative" and "analog" when referring to proteins of the present invention include any polypeptides which retain at least some of the functional properties of the corresponding native antibody or polypeptide. Fragments polypeptides of the present invention include proteolytic fragments, as well as deletion fragments, in addition to specific antibody fragments discussed elsewhere herein. Variants of the polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of the fragments of the present invention are polypeptides which have been altered so as to exhibit additional features not found on the native polypeptide. Examples include fusion proteins. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those polypeptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (SEQ ID NO:1) molecules of the invention. BLAST protein searches can be performed with the XBLAST program, score=50, wordlength=3 to obtain amino acid sequences homologous to a protein (SEQ ID NO:1) protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Various aspects of the invention are described in further detail below.

Single Domain Antigen Binding (SDAB) Molecules

Single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, fish, shark, goat, rabbit, and bovine. This term also includes naturally occurring single domain antibody molecules from species other than Camelidae and sharks.

In one aspect of the invention, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

According to another aspect of the invention, an SDAB molecule is a naturally occurring single domain antigen binding molecule known as heavy chain devoid of light chains. Such single domain molecules are disclosed in WO 9404678 and Hamers-Casterman, C. et al. (1993) *Nature* 363:446-448, for example. For clarity reasons, this variable domain derived from a heavy chain molecule naturally devoid of light chain is known herein as a VHH or Nanobody™ to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

The SDAB molecules can be recombinant, CDR-grafted, humanized, camelized, de-immunized and/or in vitro generated (e.g., selected by phage display), as described in more detail below.

The term "antigen-binding" is intended to include the part of a polypeptide, e.g., a single domain molecule described herein, that comprises determinants that form an interface that binds to a target antigen, or an epitope thereof. With respect to proteins (or protein mimetics), the antigen-binding site typically includes one or more loops (of at least four amino acids or amino acid mimics) that form an interface that binds to the target antigen. Typically, the antigen-binding site of the polypeptide, e.g., the single domain antibody molecule, includes at least one or two CDRs, or more typically at least three, four, five or six CDRs.

The term "immunoglobulin variable domain" is frequently understood in the art as being identical or substantially identical to a VL or a VH domain of human or animal origin. It shall be recognized that immunoglobulin variable domain may have evolved in certain species, e.g., sharks and llama, to differ in amino acid sequence from human or mammalian VL or VH. However, these domains are primarily involved in antigen binding. The term "immunoglobulin variable domain" typically includes at least one or two CDRs, or more typically at least three CDRs.

A "constant immunoglobulin domain" or "constant region" is intended to include an immunoglobulin domain that is identical to or substantially similar to a CL, CH1, CH2, CH3, or CH4, domain of human or animal origin. See e.g. Charles A Hasemann and J. Donald Capra, *Immunoglobulins: Structure and Function*, in William E. Paul, ed., *Fundamental Immunology*, Second Edition, 209, 210-218 (1989). The term "Fc region" refers to the Fc portion of the constant immunoglobulin domain that includes immunoglobulin domains CH2 and CH3 or immunoglobulin domains substantially similar to these.

In certain embodiments, the SDAB molecule is a monovalent, or a multispecific molecule (e.g., a bivalent, trivalent, or tetravalent molecule). In other embodiments, the SDAB molecule is a monospecific, bispecific, trispecific or tetraspecific molecule. Whether a molecule is "monospecific" or "multispecific," e.g., "bispecific," refers to the number of different epitopes with which a binding polypeptide reacts. Multispecific molecules may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an SDAB molecule. Each binding domain specifically binds one epitope. When an SDAB molecule comprises more than one binding domain, each binding domain may specifically bind the same epitope, for an antibody with two binding domains, termed "bivalent monospecific," or to different epitopes, for an SDAB molecule with two binding domains, termed "bivalent bispecific." An SDAB molecule may also be bispecific and bivalent for each specificity (termed "bispecific tetravalent molecules"). Bispecific bivalent molecules, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incorporated by reference herein. Bispecific tetravalent molecules, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., *J. Immunol.* 147:60-69 (1991); U.S. Pat. Nos. 4,474,893; 4,714,681; 4,925,648; 5,573,920; 5,601,819; Kostelny et al., *J. Immunol.* 148: 1547-4553 (1992).

In certain embodiments, the SDAB molecule is a single chain fusion polypeptide comprising one or more single domain molecules (e.g., Nanobodies™), devoid of a complementary variable domain or an immunoglobulin constant, e.g., Fc, region, that binds to one or more target antigens. An exemplary target antigen recognized by the antigen-binding polypeptides includes tumor necrosis factor α (TNF α). In certain embodiments, the antigen-binding single domain molecule binds to a serum protein, e.g., a human serum proteins chosen from one or more of serum albumin (human serum albumin (HSA)) or transferin.

TNFα

Tumor necrosis factor alpha is known in the art to the associated with inflammatory disorders such as rheumatoid arthritis, Crohn's disease, ulcerative colitis and multiple sclerosis. Both TNFa and the receptors (CD120a and CD120b) have been studied in great detail. TNFa in its bioactive form is a trimer. Several strategies to antagonize the action of TNFa using anti-TNFa antibodies have been developed and are currently commercially available, such as Remicade® and Humira®. Antibody molecules against TNFa are known. Numerous examples of TNFa-binding single domain antigen binding molecules (e.g., Nanobodies™) are disclosed in WO 2004/041862, WO 2004/041865, WO 2006/122786, the contents of all of which are incorporated by reference herein in their entirety. Additional examples of single domain antigen binding molecules are disclosed in US 2006/286066, US 2008/0260757, WO 06/003388, US 05/0271663, US 06/0106203, the contents of all of which are incorporated by reference herein in their entirety. In other embodiments, mono-, bi-, tri- and other multi-specific single domain antibodies against TNFa and a serum protein, e.g., HSA, are disclosed in these references.

In specific embodiments, the TNFα-binding Nanobody™ molecule comprises one or more of the Nanobodies™ disclosed in WO 2006/122786. For example, the TNFα-binding Nanobody™ molecule can be a monovalent, bivalent, trivalent TNFα-binding Nanobody™ molecule disclosed in WO 2006/122786. Exemplary TNFα-binding Nanobodies™ include, but are not limited to, TNF1, TNF2, TNF3, humanized forms thereof (e.g., TNF29, TNF30, TNF31, TNF32, TNF33). Additional examples of monovalent TNFα-binding Nanobodies™ are disclosed in Table 8 of WO 2006/122786. Exemplary bivalent TNFα-binding Nanobody™ molecules include, but are not limited to, TNF55 and TNF56, which comprise two TNF30 Nanobodies™ linked via a peptide linker to form a single fusion polypeptide (disclosed in WO 2006/122786). Additional examples of bivalent TNFα-binding Nanobody™ molecules are disclosed in Table 19 of WO 2006/122786 as TNF4, TNF5, TNF6, TNF7, TNF8).

In other embodiments, the HSA-binding Nanobody™ molecule comprises one or more of the Nanobodies™ disclosed in WO 2006/122786. For example, the HSA-binding Nanobody™ molecule can be a monovalent, bivalent, trivalent HSA-binding Nanobody™ molecule disclosed in WO 2006/122786. In other embodiments, the HSA-binding Nanobody™ molecule can be a monospecific or a multispecific molecule having at least one of the binding specificities bind to HSA. Exemplary TNFα-binding Nanobodies™ include, but are not limited to, ALB1, humanized forms thereof (e.g., ALB6, ALB7, ALB8, ALB9, ALB10), disclosed in WO 06/122786.

In other embodiments, two or more of the single domain molecules of the Nanobody™ molecules are fused, with or without a linking group, as a genetic or a polypeptide fusion. The linking group can be any linking group apparent to those of skill in the art. For instance, the linking group can be a biocompatible polymer with a length of 1 to 100 atoms. In one embodiment, the linking group includes or consists of polyglycine, polyserine, polylysine, polyglutamate, polyisoleucine, or polyarginine residues, or a combination thereof. For example, the polyglycine or polyserine linkers can include at least five, seven eight, nine, ten, twelve, fifteen, twenty, thirty, thirty-five and forty glycine and serine residues. Exemplary linkers that can be used include Gly-Ser repeats, for example, $(Gly)_4$-Ser (SEQ ID NO: 8) repeats of at one, two, three, four, five, six, seven or more repeats. In embodiments, the linker has the following sequences: $(Gly)_4$-Ser-$(Gly)_3$-Ser (SEQ ID NO: 9) or $((Gly)_4$-Ser)n (SEQ ID NO: 10), where n is 4, 5, or 6.

Figure 29:
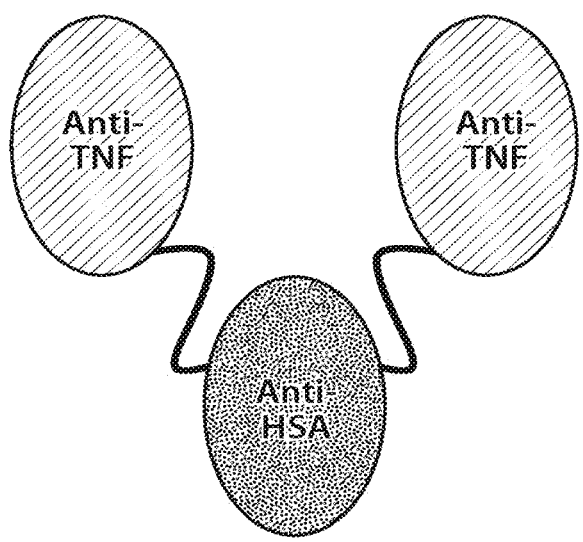
FIG. 29 depicts a schematic diagram of the predicted structure of ATN-103.

In one exemplary embodiment, an antigen-binding polypeptide composed of a single chain polypeptide fusion of two single domain antibody molecules (e.g., two camelid variable regions) that bind to a target antigen, e.g., tumor necrosis factor alpha (TNFa), and one single domain antibody molecule (e.g., a camelid variable region) that binds to a serum protein, e.g., HSA, referred to herein as "ATN-103," was shown to bind to Protein A, or a functional variant thereof. ATN-103 is a humanized, trivalent, bispecific, TNFa-inhibiting fusion protein. The antigen for this protein is tumor necrosis factor-alpha (TNF). FIG. 29 provides a schematic representation of the predicted structure of ATN-103. This fusion protein is derived from camelids and has a high degree of sequence and structural homology to human immunoglobulin VH domains. Its single polypeptide chain is composed of two binding domains to TNFα and one to human serum albumin (HSA), with two nine amino acid G-S linkers connecting the domains. A detailed description of ATN-103 is provided in WO 06/122786.

The complete amino acid sequence of the ATN-103 polypeptide chain predicted from the DNA sequence of the corresponding expression vector is shown in FIG. 30 (residues are numbered starting with the $NH_2$-terminus as Residue Number 1 of SEQ ID NO:1). The last amino acid residue encoded by the DNA sequence is $S^{363}$ and constitutes the COOH-terminus of the protein. The predicted molecular mass for disulfide-bonded ATN-103 (with no posttranslational modifications) is 38434.7 Da. ATN-103 contains no N-linked glycosylation consensus sequence. The molecular mass observed for the predominant isoform by nanoelectrospray ionization quadrupole time-of-flight mass spectrometry corresponds to 38433.9 Da confirming the absence of post-translational modifications.

In FIG. 30, complementarity determining regions (CDR) are underlined. The predicted intramolecular disulfide bonds are illustrated by connections of the cysteine residues involved. The binding domains to TNF are shown in bold and the binding domain to HSA is shown in bold italics. The amino acid linkers connecting these binding domains are in italics. The signal peptide ($^{-19}$MGW . . . VHS$^{-1}$) is also shown for the polypeptide chain.

Preparation of SDAB Molecules

The SDAB molecules may comprised of one or more single domain molecules (e.g., Nanobodies™) that are recombinant, CDR-grafted, humanized, camelized, de-immunized, and/or in vitro generated (e.g., selected by phage display). Techniques for generating antibodies and SDAB molecules, and modifying them recombinantly are known in the art and are described in detail below.

Numerous methods known to those skilled in the art are available for obtaining antibodies. For example, monoclonal antibodies may be produced by generation of hybridomas in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an Nanobody™ that specifically binds with a specified antigen. Any form of the specified antigen my be used as the immunogen, e.g., recombinant antigen, naturally occurring forms, any variants or fragments thereof, as well as antigenic peptide thereof.

One exemplary method of making antibodies and SDAB molecules includes screening protein expression libraries, e.g., phage or ribosome display libraries. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, an SDAB molecule is obtained from the non-human animal, and then modified, e.g., humanized, deimmunized, chimeric, may be produced using recombinant DNA techniques known in the art. A variety of approaches for making chimeric antibodies and SDAB molecules have been described, See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Humanized antibodies and SDAB molecules may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies and SDAB molecule described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody and SDAB molecule to a predetermined antigen.

Humanized antibodies can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing a Nanobody™ against a predetermined target, as described above, as well as from other sources. The recombinant DNA encoding the humanized SDAB molecule, e.g., Nanobody™ molecule, can then be cloned into an appropriate expression vector.

In certain embodiments, a humanized SDAB molecule, e.g., Nanobody™ molecule, is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.,* 80: 7308-7312, 1983; Kozbor et al., *Immunology Today,* 4: 7279, 1983; Olsson et al., *Meth. Enzymol.,* 92: 3-16, 1982), and may be made according to the teachings of PCT Publication WO92/06193 or EP 0239400).

Techniques for humanizing SDAB molecules, e.g., Nanobody™ molecules, are disclosed in WO 06/122786.

An SDAB molecule, e.g., Nanobody™ molecule, may also be modified by specific deletion of human T cell epitopes or "deimmunization" by the methods disclosed in WO 98/52976 and WO 00/34317. Briefly, the heavy and light chain variable domains of, e.g., a Nanobody™ can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

The SDAB molecules, e.g., Nanobody™ molecules, can be produced by living host cells that have been genetically engineered to produce the protein. Methods of genetically engineering cells to produce proteins are well known in the art. See e.g. Ausabel et al., eds. (1990), *Current Protocols in Molecular Biology* (Wiley, New York). Such methods include introducing nucleic acids that encode and allow expression of the protein into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well know by those skilled in the art (e.g., by transformation, viral infection, and/or selection). Optionally, the protein can be secreted by the host cells into the medium.

Modified SDAB Molecules

The formulations of the invention may contain at least one SDAB molecule, e.g., Nanobody™ molecule, having an amino acid sequence that differs at at least one amino acid position in one of the framework regions from the amino acid sequence of a naturally occurring domain, e.g., VH domain.

It shall be understood that the amino acid sequences of the some of the SDAB molecules of the invention, such as the humanized SDAB molecules, can differ at at least one amino acid position in at least one of the framework regions from the amino acid sequences of naturally occurring domain, e.g., a naturally occurring VHI-I domains.

The invention also includes formulations of derivatives of the SDAB molecules. Such derivatives can generally be obtained by modification, and in particular by chemical and/or biological (e.g enzymatical) modification, of the SDAB molecules and/or of one or more of the amino acid residues that form the SDAB molecules disclosed herein.

Examples of such modifications, as well as examples of amino acid residues within the SDAB molecule sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the SDAB molecule, and in particular of one or more functional groups, residues or moieties that confer one or more desired properties or functionalities to the SDAB molecules. Example of such functional groups will be clear to the skilled person.

For example, such modification may comprise the introduction (e.g. by covalent binding or in any other suitable manner) of one or more functional groups that that increase the half-life, the solubility and/or the absorption of the SDAB molecule, that reduce the immunogenicity and/or the toxicity of the SDAB molecule, that eliminate or attenuate any undesirable side effects of the SDAB molecule, and/or that confer other advantageous properties to and/or reduce the undesired properties of the SDAB molecule; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and-148-single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody™ of the invention, or optionally via a suitable linker or spacer, as will again be clear to the skilled person.

One widely used techniques for increasing the half-life and/or the reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in an SDAB molecule, an SDAB molecule may be modified no as to suitably introduce one or more cysteine residues for attachment of PEG, or an amino acid sequence comprising one or more cysteine residues for attachment of PEG may be fused to the N- and/or C-terminus of a Nanobody™ of the invention, all using techniques of protein engineering known per se to the skilled person.

Preferably, for the SDAB molecule, a PEG is used with a molecular weight of more than 5000, such as more than 10,000 and less than 200,000, such as less than 100,000; for example in the range of 20,000-80,000.

With regard to pegylation, its should be noted that generally, the invention also encompasses any SDAB molecule that has been pegylated at one or more amino acid positions, preferably in such a way that said pegylation either (1) increases the half-life in vivo; (2) reduces immunogenicity; (3) provides one or more further beneficial properties known per se for pegylation; (4) does not essentially affect the affinity of the SDAB molecule (e.g. does not reduce said affinity by more than 90%, preferably not by more than 50%, and by no more than 10%, as determined by a suitable assay, such as those described in the Examples below); and/or (4) does not affect any of the other desired properties of the SDAB molecule. Suitable PEG-groups and methods for attaching them, either specifically or non-specifically, will be clear to the skilled person.

Another, usually less preferred modification comprises N-linked or O-linked glycosylation, usually as part of co-translational and/or post-translational modification, depending on the host cell used for expressing the SDAB molecule.

Formulations

A formulation of an SDAB molecule, e.g., Nanobody™ molecule, includes an SDAB molecule, a compound that can serve as a cryoprotectant, and a buffer. The pH of the formulation is generally pH 5.5-7.0. In some embodiments, a formulation is stored as a liquid. In other embodiments, a formulation is prepared as a liquid and then is dried, e.g., by lyophilization or spray-drying, prior to storage. A dried formulation can be used as a dry compound, e.g., as an aerosol or powder, or reconstituted to its original or another concentration, e.g., using water, a buffer, or other appropriate liquid.

The SDAB molecule purification process is designed to permit transfer of the an SDAB molecule into a formulation suitable for long-term storage as a frozen liquid and subsequently for freeze-drying (e.g., using a histidine/sucrose formulation). The formulation is lyophilized with the protein at a specific concentration. The lyophilized formulation can then be reconstituted as needed with a suitable diluent (e.g., water) to resolubilize the original formulation components to a desired concentration, generally the same or higher concentration compared to the concentration prior to lyophilization.

The lyophilized formulation may be reconstituted to produce a formulation that has a concentration that differs from the original concentration (i.e., before lyophilization), depending upon the amount of water or diluent added to the lyophilate relative to the volume of liquid that was originally freeze-dried. Suitable formulations can be identified by assaying one or more parameters of antibody integrity. The assayed parameters are generally the percentage of HMW species or the percentage of LMW species.

The percentage of HMW species or LMW species is determined either as a percentage of the total protein content in a formulation or as a change in the percentage increase over time (i.e., during storage). The total percentage of HMW species in an acceptable formulation is not greater than 10% HMW species after storage as a lyophilate or liquid at −20° C. to 40° C. (e.g., at −20° C. to 25° C., at −20° C. to 15° C., at 2° C. to 8° C., at about 2° C., or at about 25° C.) for at least one year or not greater than about 10% LMW species after storage as a lyophilate or liquid at −20° C. to 40° C. for at least one year. By "about" is meant ±20% of a cited numerical value. Thus, "about 20° C." means 16° C. to 24° C.

Typically, the stability profile is less than 10% HMW/LMW at 2°-8° C. for a refrigerated product, and 25° C. for a room-temperature product. HMW species or LMW species are assayed in a formulation stored as a lyophilate after the lyophilate is reconstituted. 40° C. is an accelerated condition that is generally used for testing stability and determining stability for short-term exposures to non-storage conditions, e.g., as may occur during transfer of a product during shipping.

When the assayed parameter is the percentage change in HMW species or LMW species, the percent of total protein in one or both species after storage is compared to the percent total protein in one or both species prior to storage (e.g., upon preparation of the formulation). The difference in the percentages is determined. In general, the change in the percentage of protein in HMW species or LMW species in liquid formulations is not greater than 10%, e.g., not greater than about 8%, not greater than about 7%, not greater than about 6%, not greater than about 5%, not greater than about 4%, or not greater than about 3% after storage at 2° C.-8° C. or 25° C. for about eighteen to twenty-four months. By "about" is meant ±20% of a cited numerical value, typically, within 10%, and more typically, within 5% of a given value or range of values. Thus, about 10% means 8% to 12%. Formulations stored as lyophilized product generally have less than about 5%, less than about 4%, less than about 3%, less than about 2%, or less than about 1% of HMW species or less than about 5%, less than about 4%, less than about 3%, or less than about 2%, or less than about 1% of LMW species after reconstitution, or in liquid formulation, following storage at −30° C.-8° C., (e.g., 4° C., or −20° C.) for about six, nine, ten, twelve, fifteen, eighteen to twenty-four months.

Formulations of SDAB molecules (e.g., TNF-binding Nanobody™ molecules) can be stored as a frozen liquid formulation or a lyophilate for, e.g., at least six, nine, ten, twelve months, or at least two years, at least three years, at least four years, or at least five years. In one example, a TNF-binding Nanobody™ molecule formulation contains 10 mM histidine, 5% sucrose, 0.01% Polysorbate 80, 50 mg/mL TNF-binding Nanobody™ molecules, and has a pH of 6.0. In another example, the TNF-binding Nanobody™ molecule formulation contains 20 mM histidine, 7.5% sucrose, 0.01% Polysorbate 80, 50 mg/mL TNF-binding Nanobody™ molecules, and has a pH of 6.0. In another example, the formulation contains 20 mM histidine, 10% sucrose, 0.02% Polysorbate 80, 100 mg/mL TNF-binding Nanobody™ molecule, and has a pH of 6.0. In another example, the formulation contains 10 mM histidine, 5% sucrose, 50 mg/mL TNF-binding Nanobody™ molecule, and has a pH of 6.0. In yet another example, the formulation contains 20 mM histidine, 10% sucrose, 100 mg/mL TNF-binding Nanobody™, and has a pH of 6.0. In another example, the formulation contains 10 mM histidine, 5% sucrose, 0.01% Polysorbate 80, approximately 80 mg/mL TNF-binding Nanobody™ molecule, and has a pH of 6.0. In yet another example, the formulation contains 10 mM histidine, 5% sucrose, 0.01% Polysorbate 80, 100 mM Arginine (base), 88 to 100 mg/mL TNF-binding Nanobody™ molecule, and has a pH of 5.8. In another example, the formulation contains 10 mM histidine, 5% sucrose, 0.01% Polysorbate 80, 55 mM NaCl, 88 to 100 mg/mL TNF-binding Nanobody™ molecule, and has a pH of 6.1. In yet another example, the formulation contains 10 mM histidine, 5% sucrose, 0.01% Polysorbate 80, 55 mM Arginine HCl, 88 to 100 mg/mL TNF-binding Nanobody™ molecule, and has a pH of 6.1. In another example, the formulation contains 10 mM histidine, 5% sucrose, 0.01% Polysorbate 80, 100 mM Glycine, 88 to 100 mg/mL TNF-binding Nanobody™ molecule, and has a pH of 6.0. In yet another example, the formulation contains 10 mM histidine, 5% sucrose, 0.01% Polysorbate 80, 100 mM Methionine, 88 to 100 mg/mL TNF-binding Nanobody™ molecule, and has a pH of 6.0. In another example, the formulation contains 10 mM histidine, 8% sucrose, 0.01% Polysorbate 80, 88 to 100 mg/mL TNF-binding Nanobody™ molecule, and has a pH of 6.0. In yet another example, the formulation contains 10 mM histidine, 5% sucrose, 0.01% Polysorbate 80, 88 to 100 mg/mL TNF-binding Nanobody™ molecule, and has a pH of 6.0. In another example, the formulation contains 20 mM Histidine, 5% Sucrose, 118 mg/mL TNF-binding Nanobody™ molecule, and has a of pH 6.0. In yet another example, the formulation contains 20 mM Tris, 5% Sucrose, 117 mg/mL TNF-binding Nanobody™ molecule, has a pH of 7.2. In another example, the formulation contains 10 mM histidine, 5% sucrose, 0.01% Polysorbate 80, approximately 80 mg/mL TNF-binding Nanobody™ molecule, and has a pH of 6.0. In yet another example, the formulation contains 10 mM histidine, 5% sucrose, 0.01% Polysorbate 80, approximately 50 mg/mL TNF-binding Nanobody™ molecule, and has a pH of 6.0. In one example, the formulation contains 10 mM histidine, 5% sucrose, 0.01% Tween-80, approximately 1 mg/mL TNF-binding Nanobody™ molecule, and has a pH of 5.5. In another example, the formulation contains 10 mM histidine, 5% sucrose, 0.01% Tween-80, 150 mM arginine HCl, approximately 1 mg/mL TNF-binding Nanobody™ molecule, and has a pH of 5.5. In yet another example, the formulation contains 10 mM histidine, 5% sucrose, 0.01% Tween-80, 75 mM sodium chloride, approximately 1 mg/mL TNF-binding Nanobody™ molecule, and has a pH of 5.5. In one example, the formulation contains 10 mM histidine, 5% sucrose, 0.01% Tween-80, approximately 1 mg/mL TNF-binding Nanobody™ molecule, and has a pH of 6.0. In another example, the formulation contains 10 mM histidine, 5% sucrose, 0.01% Tween-80, 150 mM arginine HCl, approximately 1 mg/mL TNF-binding Nanobody™, and has a pH of 6.0. In yet another example, the formulation contains 10 mM histidine, 5% sucrose, 0.01% Tween-80, 75 mM sodium chloride, approximately 1 mg/mL TNF-binding Nanobody™ molecule, and has a pH of 6.0. In one example, the formulation contains 10 mM histidine, 5% sucrose, 0.01% Tween-80, approximately 1 mg/mL TNF-binding Nanobody™ molecule, and has a pH of 6.5. In another example, the formulation contains 10 mM histidine, 5% sucrose, 0.01% Tween-80, 150 mM arginine HCl, approximately 1 mg/mL TNF-binding Nanobody™ molecule, and has a pH of 6.5. In yet another example, the formulation contains 10 mM histidine, 5% sucrose, 0.01% Tween-80, 75 mM sodium chloride, approximately 1 mg/mL TNF-binding Nanobody™ molecule, and has a pH of 6.5. In one example, the formulation contains 10 mM histidine, 5% sucrose, 0.01% Tween-80, approximately 1 mg/mL TNF-binding Nanobody™ molecule, and has a pH of 7.0. In another example, the formulation contains 10 mM histidine, 5% sucrose, 0.01% Tween-80, 150 mM arginine HCl, approximately 1 mg/mL TNF-binding Nanobody™ molecule, and has a pH of 7.0. In yet another example, the formulation contains 10 mM histidine, 5% sucrose, 0.01% Tween-80, 75 mM sodium chloride, approximately 1 mg/mL TNF-binding Nanobody™ molecule, and has a pH of 7.0. In yet another example, the TNF-binding Nanobody™ molecule Nanobody™ contains 20 mM histidine, 7.5% sucrose, 0.01% Polysorbate 80, 250 mg/mL TNF-binding Nanobody™ molecules, and has a pH of 6.0.

Additional details related to components of formulations and methods of assaying the integrity of the SDAB molecule, e.g., the TNF-binding Nanobody™ molecule, in a formulation are provided infra.

SDAB molecule concentrations in formulations are generally between about 0.1 mg/mL and about 350 mg/mL, e.g., 0.5 mg/mL to about 350 mg/mL, about 0.5 mg/mL to about 300 mg/mL, about 0.5 mg/mL to about 250 mg/mL, about 0.5 mg/mL to about 150 mg/mL, about 1 mg/ml to about 130 mg/mL, about 10 mg/ml to about 130 mg/mL, about 50 mg/ml to about 120 mg/mL, about 80 mg/ml to about 120 mg/mL, about 88 mg/ml to about 100 mg/mL or about 10 mg/ml, about 25 mg/ml, about 50 mg/ml, about 80 mg/ml, about 100 mg/mL, about 130 mg/ml, about 150 mg/ml, about 200 mg/ml, about 250 mg/ml or about 300 mg/ml. In the context of ranges, "about" means −20% of the lower-cited numerical value of the range and +20% of the upper-cited numerical value of the range. In the context of ranges, e.g., about 10 mg/mL to about 100 mg/mL, this means, between 8 mg/mL to 120 mg/mL. In some cases, SDAB molecule concentrations in formulations can be, for example, between 0.1 mg/mL and 200 mg/mL, e.g., 0.5 mg/mL and 100 mg/mL, 0.5 mg/mL and 1.0 mg/mL, 0.5 mg/mL and 45 mg/mL, 1 mg/mL and 10 mg/mL, 10 mg/mL and 40 mg/mL, 10 mg/mL and 50 mg/mL, 50 mg/mL and 100 mg/mL, 100 mg/mL and 200 mg/mL. Such SDAB molecule formulations can be used as therapeutic agents. Accordingly, the concentration of SDAB molecule in a formulation is sufficient to provide such dosages in a volume of the formulation that is tolerated by a subject being treated and is appropriate for the method of administration. In one non-limiting example, to supply a high dosage subcutaneously, in which the volume limitation is small (e.g., about 1 ml to 1.2 ml per injection), the concentration of SDAB molecule is generally at least 100 mg/mL or greater, e.g., 100 mg/mL to 500 mg/mL, 100 mg/mL to 250 mg/mL, or 100 mg/mL to 150 mg/mL. Such high concentrations can be achieved, for example, by reconstituting a lyophilized formulation in an appropriate volume of diluent (e.g., sterile water for injection, buffered saline). In some cases, the reconstituted formulation has a concentration of between about 100 mg/mL and 300 mg/mL (e.g., 100 mg/mL, 125 mg/mL, 150 mg/mL, 175 mg/mL, 200 mg/mL, 250 mg/mL, 275 mg/mL, 300 mg/mL). High concentrations, for example up to 250 mg/mL, can be used for long term storage, e.g., frozen storage of large preparations of the SDAB molecule.

For delivery via inhalation, the formulation is generally somewhat concentrated (e.g., between about 100 mg/mL and 500 mg/mL) so as to provide a sufficient dose in a limited volume of aerosol for inspiration. In some cases, low concentrations (e.g., between about 0.05 mg/mL and 1 mg/mL) are used. Methods are known in the art to adapt the dosage delivered to the method of delivery, e.g., a jet nebulizer or a metered aerosol.

Buffers and Cryoprotectants

The pH of a formulation as described herein is generally between about pH 5.0 to about 7.0, for example, about pH 5.5 to about 6.5, about pH 5.5 to about 6.0, about pH 6.0 to about 6.5, pH 5.5, pH 6.0, or pH 6.5. In general, a buffer that can maintain a solution at pH 5.5 to 6.5 is used to prepare a formulation, e.g., a buffer having a pKA of about 6.0. Suitable buffers include, without limitation, histidine buffer, TRIS, 2-(N-morpholino)ethanesulfonic acid (MES), cacodylate, phosphate, acetate, succinate, and citrate. The concentration of the buffer is between about 4 mM and about 60 mM, e.g., about 5 mM to about 25 mM, for example, histidine is generally used at a concentration of up to 60 mM. In some cases, histidine buffer is used at a concentration of about 5 mM, about 10 mM or about 20 mM. In other cases, acetate or succinate buffer is used at a concentration of about 5 mM or about 10 mM.

Cryoprotectants are known in the art and include, e.g., sucrose, trehalose, and glycerol. A cryoprotectant exhibiting low toxicity in biological systems is generally used. The cryoprotectant is included in the formulation at a concentration of about 0.5% to 15%, about 0.5% to 2%, about 2% to 5%, about 5% to 10%, about 10% to 15%, and about 5% (weight/volume).

Histidine buffer, which can be used as a buffer in an TNF-binding Nanobody™ formulation, may have cryoprotectant properties. In some embodiments of the invention, a histidine buffer is used in conjunction with a cryoprotectant such as a sugar, e.g., sucrose. A formulation of the invention can specifically exclude the use of histidine in any substantial amount, e.g., neither the buffer nor the cryoprotectant component of the formulation is a histidine.

The viscosity of a formulation is generally one that is compatible with the route of administration of the formulation. In some embodiments, the viscosity of the formulation is between 1 cP and 4 cP, e.g., about 2 cP to 3.5 cP. In other embodiments, the viscosity of the formulation is between about 5 cP and about 40 cP. In specific embodiments, the viscosity of the formulation is about 1 cP, 2 cP, 2.4 cP to 2.8 cP, 3 cP, 3.1 cP to 3.2 cP, 4 cP, 5 cP, 10 cP, 15 cP, 20 cP, 25 cP, 30 cP, 35 cP, or 40 cP.

Surfactants

In certain embodiments, a surfactant is included in the formulation. Examples of surfactants include, without limitation, nonionic surfactants such as polysorbates (e.g., polysorbate-20, polysorbate-40, polysorbate-60, polysorbate-65, polysorbate-80, or polysorbate-85); Triton™; sodium dodecyl sulfate (SDS); sodium laurel sulfate; sodium octyl glycoside; lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine (e.g. lauroamidopropyl), myristamidopropyl-, palmidopropyl-, or isostearamidopropyl-dimethylamine; sodium methyl cocoyl-, or disodium methyl ofeyl-taurate; and the Monaquat™ series (Mona Industries, Inc., Paterson, N.J.), polyethyl glycol, polypropyl glycol, and copolymers of ethylene and propylene e.g., poloxamers (e.g., poloxamer 188).

The amount of surfactant added is such that it reduces aggregation of the reconstituted protein to an acceptable level as assayed using, e.g., SEC-HPLC of HMW species or LMW species, and minimizes the formation of particulates after reconstitution of a lyophilate of an TNF-binding Nanobody™ formulation. The addition of surfactant has also been shown to reduce the reconstitution time of a lyophilized formulation of TNF-binding antibodies, and aid in de-gassing the solution. For example, the surfactant can be present in the formulation (liquid or prior to lyophilization) in an amount from about 0.001% to 0.6%, e.g., from about 0.005% to 0.05%, about 0.005% to 0.2%, and about 0.01% to 0.2%.

Additions to Formulations

Formulations are stored as sterile solutions or sterile lyophilates. Prevention of the action of microorganisms in formulations can also be achieved by including at least one antibacterial and/or antifungal agent in a formulation, for example, parabens, chlorobutanol, phenol, ascorbic acid, thimerosal, and the like. In some cases, a lyophilate is reconstituted with bacteriostatic water (e.g., water containing 0.9% benzyl alcohol). Considerations for the inclusion of a preservative in a formulation are known in the art as are methods of identifying preservatives that are compatible with a specific formulation and method of delivery (e.g., see Gupta, et al. (2003), *AAPS Pharm. Sci.* 5:article 8, p. 1-9).

In some cases, the formulation is isotonic. In general, any component known in the art that contributes to the solution osmolarity/tonicity can be added to a formulation (e.g., salts, sugars, polyalcohols, or a combination thereof). Isotonicity is generally achieved using either a component of a basic formulation (such as sucrose) in an isotonic concentration or by adding an additional component such as, a sugar, a polyalcohol such as manitol sorbitol, or a salt such as sodium chloride.

In some cases, a salt is used in an TNF-binding Nanobody™ formulation, e.g., to achieve isotonicity or to increase the integrity of the TNF-binding Nanobody™ of the formulation. Salts suitable for use are discussed, supra. The salt concentration can be from 0 mM to about 300 mM.

In certain cases, the formulation is prepared with Tween (e.g., Tween® 20, Tween® 80) to decrease interfacial degradation. The Tween concentration can be from about 0.001% to about 0.05%. In one example, Tween 80 is used at a concentration of 0.01% in the formulation.

In certain other cases, the formulation is prepared with arginine. The arginine concentration in the formulation can be from about 0.01% to about 5%. In one example, arginine is used at a concentration of 2% in the formulation. In some cases both Tween and arginine are added to the TNF-binding formulations described herein.

In yet other cases, the formulation may be prepared with at least one of sorbitol, glycine, methionine, or sodium chloride. If sorbitol is included in the formulation, it can be added to a concentration of between about 1% and about 10%. In one example, sorbitol is found in the formulation at a concentration of 5%. If glycine is included in the formulation, it can be added to a concentration of between about 0.1% to about 2%. In one example, glycine is found in the formulation at a concentration of 1%. If methionine is included in the formulation, it can be added to a concentration of between about 5 mM and about 150 mM. In one example, methionine is added to the formulation at a concentration of 100 mM. In another example, methionine is added to the formulation at a concentration of about 10 mM, about 20 mM or about 70 mM. If sodium chloride is included in the formulation, it can be added to a concentration of between about 5 mM and about 100 mM. In one example, sodium chloride is added to the formulation at a concentration of 55 mM.

Storage and Preparation Methods
  Freezing

In some cases, formulations containing antibodies are frozen for storage. Accordingly, it is desirable that the formulation be relatively stable under such conditions, including, under freeze-thaw cycles. One method of determining the suitability of a formulation is to subject a sample formulation to at least two, e.g., three, four, five, eight, ten, or more cycles of freezing (at, for example −20° C. or −80° C.) and thawing (for example by fast thaw in a 37° C. water bath or slow thaw at 2°-8° C.), determining the amount of LMW species and/or HMW species that accumulate after the freeze-thaw cycles and comparing it to the amount of LMW species or HMW species present in the sample prior to the freeze-thaw procedure. An increase in the LMW or HMW species indicates decreased stability.

Lyophilization

Formulations can be stored after lyophilization. Therefore, testing a formulation for the stability of the protein component of the formulation after lyophilization is useful for determining the suitability of a formulation. The method is similar to that described, supra, for freezing, except that the sample formulation is lyophilized instead of frozen, reconstituted to its original volume, and tested for the presence of LMW species and/or HMW species. The lyophilized sample formulation is compared to a corresponding sample formulation that was not lyophilized. An increase in LMW or HMW species in the lyophilized sample compared to the corresponding sample indicates decreased stability in the lyophilized sample.

In general, a lyophilization protocol includes loading a sample into a lyophilizer, a pre-cooling period, freezing, vacuum initiation, ramping to the primary drying temperature, primary drying, ramping to the secondary drying temperature, secondary drying, and stoppering the sample. Additional parameters that can be selected for a lyophilization protocol include vacuum (e.g., in microns) and condenser temperature. Suitable ramp rates for temperature are between about 0.1° C./min. to 2° C./min., for example 0.1° C./min. to 1.0° C./min., 0.1° C./min. to 0.5° C./min., 0.2° C./min. to 0.5° C./min., 0.1° C./min., 0.2° C./min., 0.3° C./min., 0.4° C./min., 0.5° C./min., 0.6° C./min., 0.7° C./min., 0.8° C./min., 0.9° C./min., and 1.0° C./min. Suitable shelf temperatures during freezing for a lyophilization cycle are generally from about −55° C. to −5° C., −25° C. to −5° C., −20° C. to −5° C., −15° C. to −5° C., −10° C. to −5° C., −10° C., −11° C., −12° C., −13° C., −14° C., −15° C., −16° C., −17° C., −18° C., −19° C., −20° C., −21° C., −22° C., −23° C., −24° C., or −25° C. Shelf temperatures can be different for primary drying and secondary drying, for example, primary drying can be performed at a lower temperature than secondary drying. In a non-limiting example, primary drying can be executed at 0° C. and secondary drying at 25° C.

In some cases, an annealing protocol is used during freezing and prior to vacuum initiation. In such cases, the annealing time must be selected and the temperature is generally above the glass transition temperature of the composition. In general, the annealing time is about 2 to 15 hours, about 3 to 12 hours, about 2 to 10 hours, about 3 to 5 hours, about 3 to 4 hours, about 2 hours, about 3 hours, about 5 hours, about 8 hours, about 10 hours, about 12 hours, or about 15 hours. The temperature for annealing is generally from about −35° C. to about −5° C., for example from about −25° C. to about −8° C., about −20° C. to about −10° C., about −25° C., about −20° C., about −15° C., about 0° C., or about −5° C. In some cases, the annealing temperature is generally from −35° C. to 0° C., for example from −25° C. to −8° C., −20° C. to −10° C., −25° C., −20° C., −15° C., 0° C.

The stability of the formulations described herein can be tested using a variety of lyophilization parameters including: the primary drying shelf temperatures from −25° C. to 30° C., and secondary drying durations of 2 hours to 9 hours at 0° to 30° C.

In one non-limiting example, a formulation of 10 mM histidine, 5% sucrose, 0.01% Polysorbate 80, pH 6.0, at a protein concentration of 50 mg/mL TNF-binding Nanobody™ was formulated in bulk and lyophilized. After lyophilization, the product is reconstituted with approximately half the fill volume to deliver protein at 100 mg/mL. The TNF antibody was demonstrated to be robust after lyophilization to extremes in product temperature. The stability profile upon storage at 50° C. for four weeks was identical for material that had been prepared using a variety of freeze-drying cycles (e.g., see FIGS. 16-20), some of which had nearly 10° C. differences in product temperature during primary drying (e.g., FIG. 13). In general, a lyophilization cycle can run from 10 hours to 100 hours, e.g., 20 hours to 80 hours, 30 hours to 60 hours, 40 hours to 60 hours, 45 hours to 50 hours, 50 hours to 65 hours.

Non-limiting examples of the temperature range for storage of an antibody formulation are about −20° C. to about 50° C., e.g., about −15° C. to about 30° C., about −15° C. to about 20° C., about 5° C. to about 25° C., about 5° C. to about 20° C., about 5° C. to about 15° C., about 2° C. to about 12° C., about 2° C. to about 10° C., about 2° C. to about 8° C., about 2° C. to about 6° C., or about 2° C., 3° C., 4° C., 5° C., 6° C., 7° C., 8° C., 10° C., 15° C., 25° C., or 30° C. Notwithstanding the storage temperatures, in certain cases, samples are stable under temperature changes that may transiently occur during storage and transportation conditions that can be anticipated for such compositions.

Spray-Drying

In some cases, a formulation is spray-dried and then stored. Spray-drying is conducted using methods known in the art, and can be modified to use liquid or frozen spray-drying (e.g., using methods such as those from Niro Inc. (Madison, Wis.), Upperton Particle Technologies (Nottingham, England), or Buchi (Brinkman Instruments Inc., Westbury, N.Y.), or U.S. Patent Publ. Nos. 20030072718 and 20030082276).

Determination of SDAB Molecule Integrity

The accumulation of LMW species and HMW species are useful measures of antibody stability. Accumulation of either LMW or HMW in a formulation is indicative of instability of a protein stored as part of the formulation. Size exclusion chromatography with HPLC can be used to determine the presence of LMW and HMW species. Suitable systems for such measurements are known in the art, e.g., HPLC systems (Waters, Milford, Mass.). Other systems known in the art can be used to evaluate the integrity of antibody in a formulation, for example, SDS-PAGE (to monitor HMW and LMW species), bioassays of antibody activity, enzyme-linked immunosorbent assay, ability to bind purified target protein (e.g., TNFα), and cation exchange-HPLC (CEX-HPLC; to detect variants and monitor surface charge). In one example, a bioassay is a cell-based assay in which inhibition of TNFα-dependent activity is examined in the presence of different concentrations of formulated Nanobody™ molecule to demonstrate biological activity.

Articles of Manufacture

The present application also provides an article of manufacture that includes a formulation as described herein and provides instructions for use of the formulation.

Formulations to be used for administration to a subject, e.g., as a pharmaceutical, must be sterile. This is accomplished using methods known in the art, e.g., by filtration through sterile filtration membranes, prior to, or following, formulation of a liquid or lyophilization and reconstitution. Alternatively, when it will not damage structure, components of the formulation can be sterilized by autoclaving and then combined with filter or radiation sterilized components to produce the formulation.

The pharmaceutical formulation can be administered with a transcutaneous delivery device, such as a syringe, including a hypodermic or multichamber syringe. In one embodiment, the device is a prefilled syringe with attached or integral needle. In other embodiments, the device is a prefilled syringe not having a needle attached. The needle can be packaged with the prefilled syringe. In one embodiment, the device is an auto-injection device, e.g., an auto-injector syringe. In another embodiment the injection device is a pen-injector. In yet another embodiment, the syringe is a staked needle syringe, luer lock syringe, or luer slip syringe. Other suitable delivery devices include stents, catheters, microneedles, and implantable controlled release devices. The composition can be administered intravenously with standard IV equipment, including, e.g., IV tubings, with or without in-line filters.

In certain embodiments, a syringe is suitable for use with an autoinjector device. For example, the autoinjector device can include a single vial system, such as a pen-injector device for delivery of a solution. Such devices are commercially available from manufacturers such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, DosePro®, Medi-Ject®, e.g., as made or developed by Becton Dickensen (Franklin Lakes, N.J.), Ypsomed (Burgdorf, Switzerland; Bioject, Portland, Oreg.; National Medical Products, Weston Medical (Peterborough, UK), Medi-Ject Corp (Minneapolis, Minn.), and Zogenix, Inc, Emeryville, Calif. Recognized devices comprising a dual vial system include those pen-injector systems for reconstituting a lyophilized drug in a cartridge for delivery of the reconstituted solution such as the HumatroPen®.

The article of manufacture can include a container suitable for containing the formulation. A suitable container can be, without limitation, a device, bottle, vial, syringe, test tube, nebulizer (e.g., ultrasonic or vibrating mesh nebulizers), i.v. solution bag, or inhaler (e.g., a metered dose inhaler (MDI) or dry powder inhaler (DPI)). The container can be formed of any suitable material such as glass, metal, or a plastic such as polycarbonate, polystyrene, or polypropylene. For example, the container (e.g., syringe or vial) can be formed out of glass, plastic, a cyclic olefin copolymer, or a cyclic olefin polymer. Optionally, the container (e.g., syringe or vial) has a stopper, e.g., a rubber stopper. Specific embodiments of containers for storing the present formulations include: (i) liquid in a glass vial with rubber stopper; (ii) liquid in a glass prefillable syringe with rubber plunger; and (iii) liquid in a prefillable polymeric syringe, for example cyclic olefin copolymer (COC), or cyclic olefin polymer (COP), with rubber plunger.

In general, the container is of a material that does not adsorb significant amounts of protein from the formulation and is not reactive with components of the formulation.

In some embodiments, the container is a clear glass vial with a stopper, e.g., a West 4432/50 1319 siliconized gray stopper or a West 4023 Durafluor stopper. In some embodiments, the container is a syringe. In specific embodiments, the formulation comprises 100 mg/mL of the TNF-binding Nanobody™, 20 mM histidine, 7.5% sucrose, 0.01% polysorbate-80, pH 6.0 in a pre-filled syringe. In another embodiment, the formulation comprises about 10 mg/mL, about 100 mg/mL of the TNF-binding Nanobody™, 20 mM histidine, 7.5% sucrose, 0.01% polysorbate-80, pH 6 in a prefillable cyclic olefin syringe and a West 4432/50 siliconized gray rubber plunger. In other embodiments, the formulations include about 10 mg/mL, about 50 mg/mL, about 100 mg/mL of the TNF-binding Nanobody™, 20 mM histidine, 7.5% sucrose, 0.01% polysorbate-80, pH 6 in a prefinable glass syringe and a West 4432/50 siliconized gray rubber plunger or West 4023/50 Daikyo Flourotec/B2 coated rubber plunger.

The articles of manufacture described herein can further include a packaging material. The packaging material provides, in addition to the information for use or administration, e.g., information required by a regulatory agency regarding conditions under which the product can be used. For example, the packaging material can provide instructions to the patient on how to inject a pre-filled syringe containing the formulations described herein, or how to reconstitute the lyophilized formulation in an aqueous diluent to form a solution within a specified period, e.g., over a period of 2-24 hours or greater. The presently claimed formulations are useful for human pharmaceutical product use.

In certain embodiments, the formulations can be administered as nebulizers. Examples of nebulizers include, in non-limiting examples, jet nebulizers, ultrasonic nebulizers, and vibrating mesh nebulizers. These classes use different methods to create an aerosol from a liquid. In general, any aerosol-generating device that can maintain the integrity of the protein in these formulations is suitable for delivery of formulations as described herein.

In other embodiments, the pharmaceutical compositions can be administered with medical devices. For example, pharmaceutical compositions can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. The therapeutic composition can also be in the form of a biodegradable or nonbiodegradable sustained release formulation for subcutaneous or intramuscular administration. See, e.g., U.S. Pat. Nos. 3,773,919 and 4,767,628 and PCT Application No. WO 94/15587. Continuous administration can also be achieved using an implantable or external pump. The administration can also be conducted intermittently, e.g., single daily injection, or continuously at a low dose, e.g., sustained release formulation. The delivery device can be modified to be optimally suited for administration of the SDAB molecule. For example, a syringe can be siliconized to an extent that is optimal for storage and delivery of the SDAB molecule. Of course, many other such implants, delivery systems, and modules are also known. The invention also features a device for administering a first and second agent. The device can include, e.g., one or more housings for storing pharmaceutical preparations, and can be configured to deliver unit doses of the first and second agent. The first and second agents can be stored in the same or separate compartments. For example, the device can combine the agents prior to administration. It is also possible to use different devices to administer the first and second agent.

Administration and Method of Treatment

The formulations of the invention be administered to a subject (e.g., a human subject) alone or combination with a second agent, e.g., a second therapeutically or pharmacologically active agent, to treat or prevent (e.g., reduce or ameliorate one or more symptoms associated with) a TNFα associated disorder, e.g., inflammatory or autoimmune disorders. The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject.

Non-limiting examples of immune disorders that can be treated include, but are not limited to, autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis); acute inflammatory conditions (e.g., endotoxemia, sepsis and septicaemia, toxic shock syndrome and infectious disease); transplant rejection and allergy. In one embodiment, the TNFα associated disorder is, an arthritic disorder, e.g., a disorder chosen from one or more of rheumatoid arthritis, juvenile rheumatoid arthritis (RA) (e.g., moderate to severe rheumatoid arthritis), osteoarthritis, psoriatic arthritis, or ankylosing spondylitis, polyarticular juvenile idiopathic arthritis (JIA); or psoriasis, ulcerative colitis, Crohn's disease, inflammatory bowel disease, and/or multiple sclerosis.

In certain embodiments, the formulations include a second therapeutic agent. For example, for TNF-Nanobodies™, the second agent may be an anti-TNF antibody or TNF binding fragment thereof, wherein the second TNF antibody has a different epitope specificity than the TNF-binding SDAB molecule of the formulation. Other non-limiting examples of agents that can be co-formulated with TNF-binding SDAB include, for example, a cytokine inhibitor, a growth factor inhibitor, an immunosuppressant, an anti-inflammatory agent, a metabolic inhibitor, an enzyme inhibitor, a cytotoxic agent, and a cytostatic agent. In one embodiment, the additional agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Arava®), tumor necrosis factor inhibitors, including etanercept (Enbrel®), inflixintab (Remicade®) (with or without methotrexate), and adalimumab (Humira®), anti-CD20 antibody (e.g., Rituxan®), soluble interleukin-1 receptor, such as anakinra (Kineret), gold, minocycline (Minocin®), penicillamine, and cytotoxic agents, including azathioprine, cyclophosphamide, and cyclosporine. Such combination therapies may advantageously tower dosages of the administered therapeutic agents, thus avoiding possible toxicities or complications associated with the various monotherapies.

The formulations of the invention can be in the form of a liquid solution (e.g., injectable and infusible solutions). Such compositions can be administered by a parenteral mode (e.g., subcutaneous, intraperitoneal, or intramuscular injection), or by inhalation. The phrases "parenteral administration" and "administered parenterally" as used herein mean modes of administration other than enteral and topical administration, usually by injection, and include, subcutaneous or intramuscular administration, as well as intravenous, intracapsular, intraorbital, intracardiac, intradermal, intraperitoneal, transtracheal, subcuticular, subcapsular, subarachnoid, intraspinal, epidural and intrasternal injection and infusion. In one embodiment, the formulations described herein are administered subcutaneously.

Pharmaceutical formulations are sterile and stable under the conditions of manufacture and storage. A pharmaceutical composition can also be tested to insure it meets regulatory and industry standards for administration.

A pharmaceutical formulation can be formulated as a solution, microemulsion, dispersion, liposome, or other ordered structure suitable to high protein concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In some embodiments, parameters that describe the formulations, e.g., parameters that may appear on the product label, are characterized. Such parameters include, e.g., color (typically colorless to slightly yellow, or colorless to yellow), clarity (typically clear to slightly opalescent, or clear to opalescent), and viscosity (typically between about 1 to 5 cP when measured at ambient temperature, such as at 20° C. to 30° C.). Such parameters can be measured by methods known in the art. For example, clarity can be measured using commercially available opalescence standards (available from, e.g., Hach Company, Loveland, Colo. 80539).

EXAMPLES

The invention is further illustrated by the following examples. The examples are provided for illustrative purposes only. They are not to be constructed as limiting the scope or content of the invention in any way.

Example 1: Stability of High Concentration Lyophilized Formulation of ATN-103 (6 Months Duration)

One method of storing an antibody to be used for, e.g., therapeutic applications, is as a dried powder prepared by lyophilization. Accordingly, the long-term stability of a lyophilized TNF-binding formulation was studied.

Briefly, a formulation containing a humanized TNF-binding Nanobody™ (50 mg/ml), 10 mM histidine, 5% sucrose (weight/volume), 0.01% Potysorbate 80, pH 6.0, was prepared by sterile filtration and was dispensed into a 5 ml depyrogenated glass tubing vial, and then lyophilized. The formulation was stored at 4° C., 25° C., or 40° C. for one month, three months, and six months, then reconstituted in sterile water (USP) to bring the reconstituted formulation such that the formulation was 100 mg/ml TNF-binding Nanobody™, 20 mM histidine, 10% sucrose, 0.02% Polysorbate 80, pH 6.0.

The stability of the high concentration liquid was assessed by biological activity, Human Serum Albumin (HSA) binding, percentage of HMW and percentage of LMW by SE-HPLC, percentage of TNF-binding Nanobody™ and percentage of non-product impurity by SDS-CE, and CEX-HPLC assessment of relative retention time and comparability of elution profile to TNF-binding Nanobody™ reference standard.

The lyophilized TNF-binding Nanobody™ formulations were assayed for biological activity using an assay disclosed in WO 2006/122786. FIG. 1 illustrates the data from such a set of bioassays. The data were expressed as units per milligram. Samples were about $5\text{-}5.5\times10^6$ U/mg prior to storage and were about $4.5\text{-}5.5\times10^6$ U/mg after incubation. Overall, there was no substantial change in the amount of bioactivity after six months of storage in any of the samples. Thus, the formulation is, as determined by biological activity, suitable for storage of the lyophilized formulation for at least six months.

Figure 2:
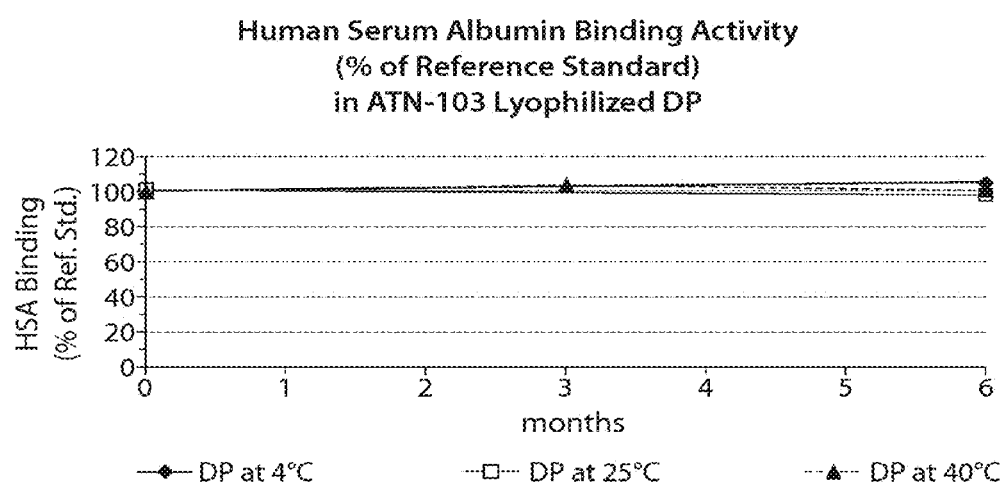
FIG. 2 depicts the results of Human Serum Albumin (HSA) binding activity of a lyophilized formulation of TNF-binding Nanobody™ (ATN-103). The results are shown as percentage (%) of TNF-binding Nanobody™ reference standard.

The lyophilized TNF-binding Nanobody™ formulations were also assayed for Human Serum Albumin (HSA) binding activity. FIG. 2 illustrates the data from such a set of binding assays. The initial binding activity of the formulation was about 100% of the reference sample and did not change substantially for any of the samples over the six-month period of testing. Thus, the formulation is, as determined by HSA binding activity, suitable for storage of the lyophilized formulation for at least six months.

Figure 3:
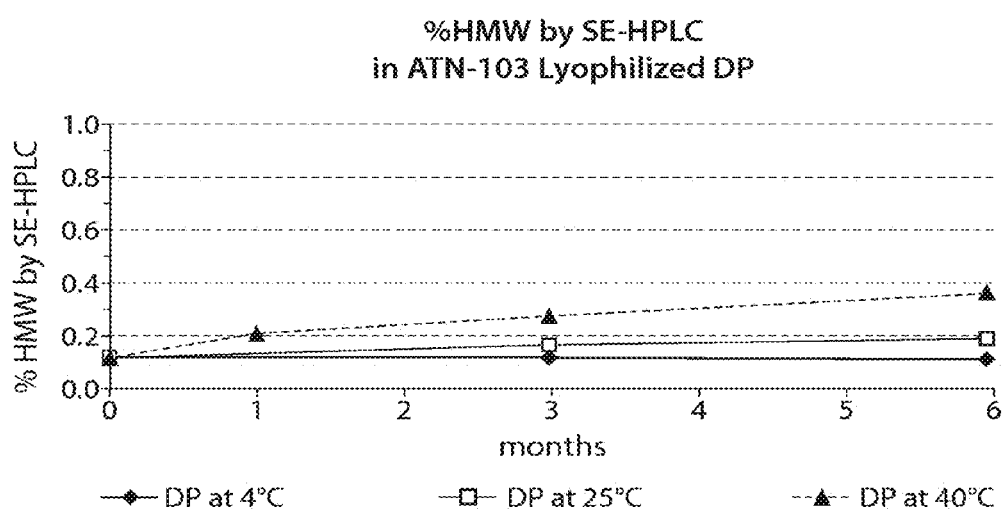
FIG. 3 depicts the results for size exclusion-HPLC (SE-HPLC) in terms of % of high molecular weight (HMW) species for lyophilized formulation.

The percentage of HMW species was assayed using SE-HPLC. The percentage of HMW species in the formulation before lyophilization and reconstitution was about 0.1% of the total protein in the formulation and was also between about 0.1%-0.2% in all samples stored at 4° C. and 25° C. (FIG. 3). After six months of storage at 40° C., the formulations were about 0.35% HMW species (FIG. 3). Thus, there was no substantial increase in the level of HMW species in samples stored at 4° C. and 25° C. for six months.

The percentage of LMW species was assayed using SE-HPLC. The percentage of LMW species in the formulation was below limit of detection (i.e. 0.0%) at temperatures of 4° C., 25° C. and 40° C. for up to six months.

Figure 4:
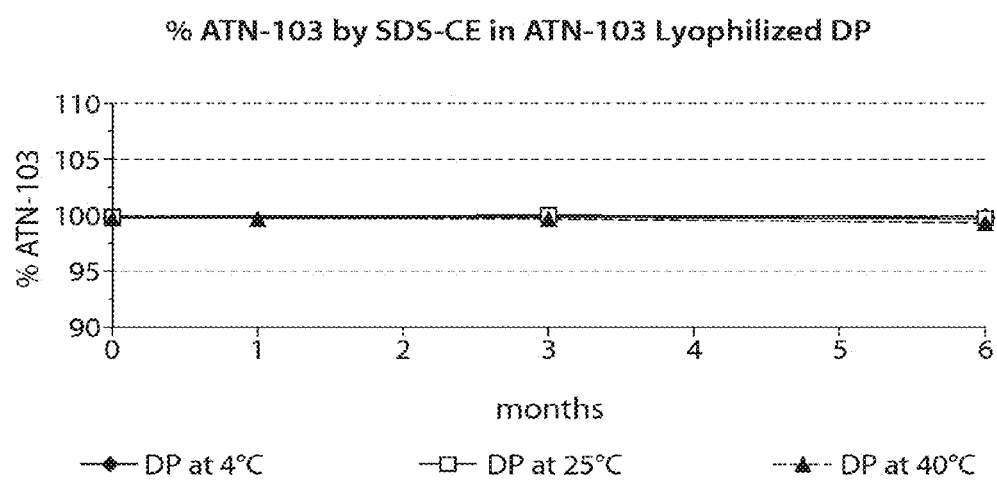
FIG. 4 depicts the results for SDS-capillary electrophoresis (SDS-CE) in terms of % TNF-binding Nanobody™ for lyophilized formulation.

The percentage of TNF-binding Nanobody™ was assayed using SDS-CE. The initial percentage of TNF-binding Nanobody™ in the formulation was about 100% and did not change substantially for any of the samples over the six-month period of testing (FIG. 4).

The percentage of non-product impurity was assayed using SDS-CE. Negligible non-product impurity was observed by SDS-CE for formulation at temperatures of 4° C., 25° C. and 40° C. for up to six months.

The lyophilized TNF-binding Nanobody™ formulations were also tested for identity using CEX-HPLC. The elution profile for the formulation was comparable to reference standard at temperatures of 4° C., 25° C. and 40° C. for up to six months. The relative retention time of designated peak was unchanged at 1.00 standard at temperatures of 4° C., 25° C. and 40° C. for up to six months.

The effect of addition of Polysorbate-80 on reconstitution properties for lyophilized TNF-binding Nanobody™ formulation was tested as well. The addition of polysorbate 80 to the lyophilized product improves the quality of the product by improving the appearance and dissolution of the lyophilized powder as can be seen in the table below.

TABLE 1

| | With Polysorbate-80 | Without Polysorbate-80 |
|---|---|---|
| Recon Time | 2 min, 39 sec | 3 min, 16 sec |
| Clear Time | Immediate | <5 min |
| Foaming | Little foam | Slightly more foam |
| Bubble dissapation | immediate | <3 min |

The data described herein show limited changes in degradation products as a function of storage time at various temperatures.

Example 2: Robustness of the TNF-Binding Nanobody™ Formulation to Lyophilization In addition to formulation lyophilized by applying the target lyophilization cycle (Example 1), two additional lots of drug product were prepared by applying two additional "robustness" lyophilization cycles, to the same formulation. The two "robustness" lyophilization cycles mimic significant process deviations that could occur in a manufacturing setting. The same drug product formulation was used in the robustness study as in the target (control) lyophilization cycle study: 10 mM Histidine, 5% Sucrose, 0.01% Polysorbate 80, 50 mg/mL TNF-binding Nanobody™, at pH 6.0. Upon reconstitution (using reconstitution diluent volume approximately half that of the filled product prior to lyophilization) the ATN-103 formulation is as follows: 20 mM Histidine, 10% Sucrose, 0.02% Polysorbate 80, 100 mg/mL TNF-binding Nanobody™, at pH 6.0.

Figure 5:
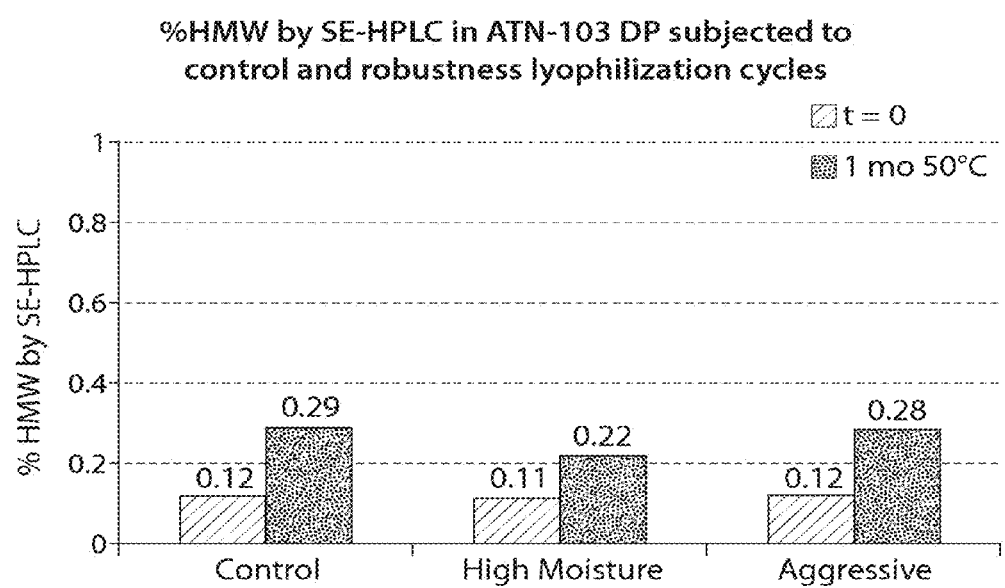
FIG. 5 depicts SE-HPLC results for % HMW species for formulation subjected to control and robustness lyophilization cycles.

The two robustness lyophilization cycles that mimic significant process deviations are termed "high moisture" and "aggressive". FIG. 5 demonstrates the formulation subjected to the robustness lyophilization cycles shows comparable stability to that of the target (control) cycle. The lyophilization robustness formulation vials were placed on accelerated stability side by side with the control lyophilization cycle, and analyzed by SE-HPLC.

These data demonstrate that the ATN-103 lyophilized formulation is robust to significant process deviations without product impact.

The percentage of LMW species for formulation subject to control and robustness lyophilization cycles was assayed using SE-HPLC. The percentage of LMW species by SE-HPLC for lyophilized TNF-binding Nanobody™ was below limit of detection (i.e. 0.0%) at $t_0$ and 50° C. for up to one month for all three cycles.

Lyophilization Practices

In all runs, an aluminum foil shield in front of the door and a shelf height of 63 mm was used to minimize radiation within the lyophilizer. In all runs, one tray was entirely filled to maintain a consistent load on the lyophilizer. Stoppers were autoclaved and dried for all protein vials. All vials for protein samples were rinsed with de-ionized water and depyrogenated. Vials and stoppers that were used to fill the remainder of the tray were untreated.

Vials seeded with the TNF-binding Nanobody™ formulation were prepared aseptically in a biosafety cabinet at a target of 160 mg/vial. Vials for stability studies were filled with 3.2 ml of fresh formulation prior to each run (material that had not been previously lyophilized). During lyophilization, additional vials were filled with suitable buffers that were compatible with the target lyophilization cycle to maintain a consistent load on the lyophilizer. Lyophilization was monitored through the use of thermocouples within the protein array.

Modulated Differential Scanning Calorimetry (mDSC)

All samples for mDSC were run in modulated mode with an amplitude of 0.5° C. and a period of 100 seconds. For post-lyophilization powders, samples were heated at 2° C./min. to 150° C. All powder samples were prepared using a nitrogen-purged glove box. For liquid samples, all temperature ramps were performed at 0.5° C./min. and temperatures were matched to those utilized in the lyophilization cycles. The final heating ramp was performed at 2° C./min. to magnify the glass transition. Liquid samples were prepared on the laboratory bench.

Moisture Analysis

Karl Fischer titration was used to assay moisture in lyophilized samples. Lyophilized samples were reconstituted with 3 ml methanol.

Duplicate or triplicate injections of 500 μL were performed. A 1% water standard was injected post use as a suitability check.

Fourier Transform Infrared Spectroscopy (FTIR)

FTIR measured secondary structure of the antibody in the dry powder state. A pellet containing approximately 1 mg of formulated, dried protein dispersed within 300 mg KBr was pressed and scanned 200 times. After data collection, analysis involved spectral subtraction of sucrose placebo, baseline correction, smoothing, second derivative, and area normalization.

Stability

The stability of lyophilized antibody in formulations was assessed as a function of storage time and temperature. Samples of lyophilized TNF-binding Nanobody™ were assayed post-lyophilization, after four weeks of storage at 2° C.-8° C. and after two weeks and four weeks of storage at 50° C. Refrigerated samples were stored in a walk-in refrigerated cold room. High temperature samples were stored in a Lab Line Imperial incubator set at 50° C. At the appropriate time points samples were removed from storage and allowed to warm up or cool down to room temperature before assaying.

Reconstitution and Visual Appearance

Vials of lyophilized formulations from both post-lyophilization analysis and storage stability analysis were visually inspected before, during, and after being reconstituted with 1.3 ml of sterile water for injection. Vials were inspected in a light box against both a black and a white background for cake color, integrity, moisture, particulates, and defects before reconstituting. After visually inspecting the lyophilized cake, the cap and crimp seal were removed from the vial using a de-crimper. The stopper was removed and the sterile water for injection was slowly dispensed into the vial using an appropriate pipette. The diluent was dispensed using a swirling motion to ensure full wetting of the cake. Once the diluent was completely dispensed, timing of reconstitution was initiated with a standard laboratory timer and the vial was restoppered. Reconstitution was complete when the final piece of solid dissolved. Rolling the vial between one's hands facilitated reconstitution. As the lyophilized cake was in the process of reconstituting, observations about the state of the dissolving solution such as clarity, bubbling, and foaming were recorded. Once reconstitution was complete, the reconstitution time was recorded and the vials were left on the bench for several minutes so that the resulting solution could settle and the majority of bubbles formed during reconstitution could dissipate. The reconstituted solution was then inspected in a light box against both a black and a white background for color, clarity, and particulates.

High Performance Size Exclusion Chromatography (SEC-HPLC)

Two microliters of neat samples of TNF-binding Nanobody™ formulation were injected onto a G3000swxl column with a guard column (TosoHaas Part Nos. 08541 and 08543). The mobile phase was phosphate buffered saline (PBS) with 250 mM sodium chloride added. The flow rate was 0.75 ml/min. and the nm time was 30 minutes. The ultraviolet absorbance was monitored at a wavelength of 280 nm. The chromatogram was integrated to separate the main TNF-binding Nanobody™ peak from high and low molecular weight species using Waters Empower™ software.

Ultraviolet-Visible Absorbance Spectroscopy for Concentration Determination ($A_{280}$)

Samples of the formulation having antibody at a concentration of 100 mg/ml were diluted to approximately 0.5 mg/mL and 0.25 mg/mL by adding 10 µl of sample to 1990 µl and 3990 µl of 10 mM histidine, 5% sucrose, pH 6.0, respectively. Two hundred microliters of the resulting solutions were placed in individual wells in a 96-well microplate along with a buffer blank. The plate was read in a Spectramax® Plus plate reader for ultraviolet absorbance at wavelengths of 280 nm and 320 nm. Subtracting the 320 nm absorbance from the 280 nm absorbance and dividing by the extinction coefficient (1.405 mL/mg-cm) multiplied by the path length (1 cm) determined protein concentrations of the solution in each well. The appropriate dilution factor was applied, and an average protein concentration was determined.

Ultraviolet-Visible Absorbance Spectroscopy for Light Scatter ($A_{420}$)

Two hundred microliters of each TNF-binding Nanobody™ sample to be analyzed was aliquoted into individual wells on a 96-well microplate. A buffer blank served as a control. The plate was read in a Spectramax Plus plate reader for visible absorbance at a wavelength of 420 nm.

Cycle Development Strategy

A series of sequential steps (described below) were used to develop a lyophilization cycle.

Critical Product Temperature Identification

The critical product temperature for an TNF-binding Nanobody™ was identified by modulated Differential Scanning Calorimetry (mDSC). This method is used to identify the glass transition temperature of the frozen product (mDSC). A lyophilization cycle that maintains the product below this temperature during primary drying should yield an intact cake structure. The lowest temperature suitable temperature was assumed to be −25° C., and so this temperature is generally included in procedures designed to test conditions and formulations when developing a formulation and methods for lyophilization of an antibody as described herein.

Lyophilization Cycle Execution

Based on the results from the studies described, supra, three different lyophilization cycles were performed to examine three parameters of interest in developing a suitable lyophilization procedure for preparing a lyophilized formulation suitable for storage or other procedures. The first parameter examined was control cycle, which repeats cycles from previous stability studies. All prior developmental stability cycles utilized this cycle, so it served as a starting point for this analysis.

The second parameter tested was the impact of not performing the secondary drying step, in order to generate lyophilized cakes with high residual moisture content. This lyophilization cycle serves as an evaluation of the sensitivity of an TNF-binding Nanobody™ formulation to high residual moisture content, and can be used in evaluation of manufacturing deviations during early clinical lots prior to the execution of formal lyophilization robustness studies.

The third parameter tested was an aggressive cycle. Increasing the primary drying temperature significantly above the control cycle set point can significantly increase the TNF-binding Nanobody™ formulation product temperature during primary drying. This lyophilization cycle serves as an evaluation of the sensitivity of an TNF-binding Nanobody™ formulation to product temperature during lyophilization, and can be used in evaluation of manufacturing deviations during early clinical lots prior to the execution of formal lyophilization robustness studies.

Assessment of Lyophilization Cycles

The assessment of the selected lyophilization cycles TNF-binding Nanobody™ formulations was split into two aspects: immediate comparison based on tests performed post-lyophilization, and potential longer-term impact caused after incubation under accelerated conditions.

Critical Product Temperature Identification

The TNF-binding Nanobody™ formulation product contained nearly 50% protein. As such, the protein was anticipated to dominate the physical properties of the frozen and lyophilized states. Prior to lyophilization, sub-ambient modulated Differential Scanning Calorimetry (mDSC) searched for the glass transition temperature of the freeze-concentrated amorphous phase of the formulation. Based on data from the aggressive lyophilization development cycle, a product temperature of −12° C. was selected as the critical temperature to remain below during lyophilization.

Example 3: Stability of High Concentration Liquid Formulation of TNF-Binding Nanobody™ (6 Months Duration)

In some cases, it is desirable to store an TNF-binding Nanobody™ formulation in a liquid format. Accordingly, the long-term stability of a liquid TNF-binding formulation containing a relatively high concentration of TNF-binding Nanobody™ was studied. Briefly, a formulation containing a humanized TNF-binding Nanobody™ (approximately 80 mg/mL), 10 mM histidine, 5% sucrose, 0.01% Polysorbate 80, pH 6.0 was prepared for storage by sterile filtering the formulation in depyrogenated stainless steel vessels. The formulation was stored at −20° C. or 4° C., for about three months and six months. The stability of the high concentration liquid was assessed by biological activity, Human Serum Albumin (HSA) binding, percentage of HMW and percentage of LMW by SE-HPLC, percentage of ATN-103 and percentage of non-product impurity by SDS-CE, and CEX-HPLC assessment of relative retention time and comparability of elution profile to TNF-binding Nanobody™ reference standard.

Figure 6:
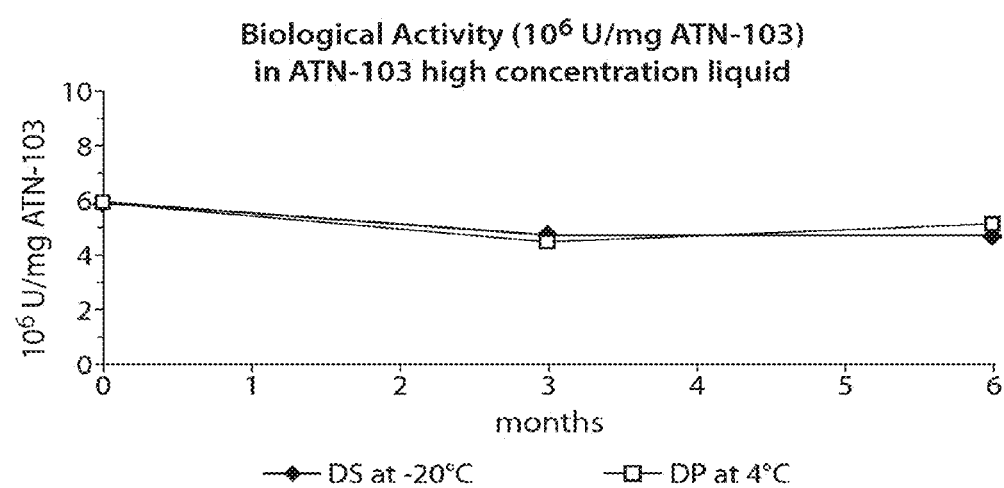
FIG. 6 depicts the results of the biological activity of $10^6$ U/mg TNF-binding Nanobody™ after storage for up to six months at a high concentration liquid formulation.

A biological activity assay was used as stability parameter for the high concentration liquid TNF-binding Nanobody™ formulation. The assay was conducted as described, supra, in Example 1. Samples were stored at −20° C. and 4° C. for about three months and six months. The data were expressed as units per milligram (FIG. 6). Samples were about $6 \times 10^6$ U/mg prior to storage and were about $4.5\text{-}5 \times 10^6$ U/mg after incubation. This reflects essentially no change in the bioactivity of the samples during storage. The variability in the values reflects the variability inherent in the assay. Because there is no decrease in the amount of biological activity in the samples, these data provide further support for the suitability of the formulation for storage of TNF-binding.

Figure 7:
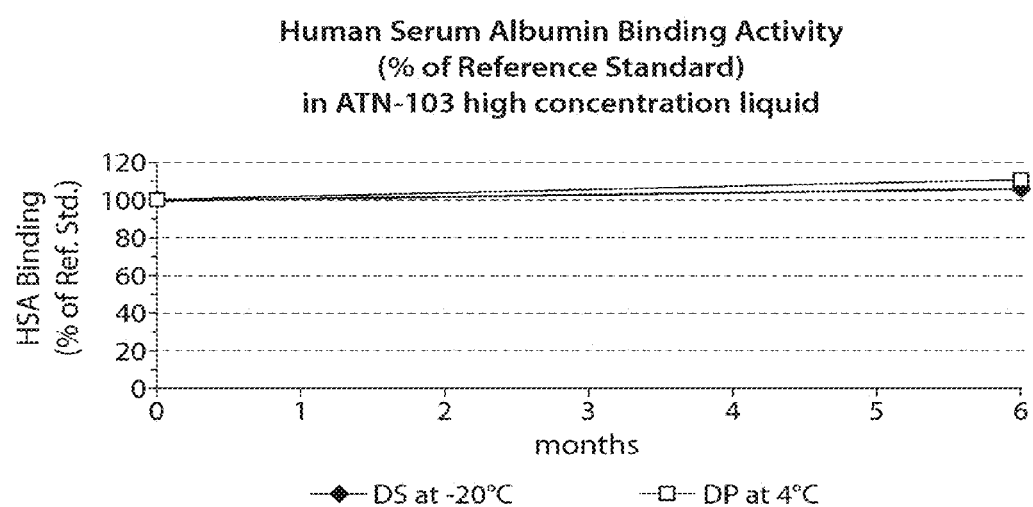
FIG. 7 depicts results of Human Serum Albumin (HSA) binding activity (percentage of TNF-binding Nanobody™ Reference Standard) of high concentration liquid formulation stored for up to six months at the temperatures indicated.

Yet another stability parameter was examined using the high concentration liquid TNF-binding Nanobody™ formulation: that of binding activity. In these experiments, the percentage of binding activity of the formulation was determined compared to a control after storage at −20° and 4° C. for six months. The assay specifically monitors the binding affinity of the TNF-binding to Human Serum Albumin (HSA). The initial binding activity of the formulation was about 100% of the reference sample and did not change substantially for any of the samples over the six-month period of testing (FIG. 7). Measured binding activity was up to about 110% of the reference, which, given the error generally observed in this assay, reflects essentially no change in the binding activity of the samples over time, and there were no temperature-related trends in binding results.

Figure 8:
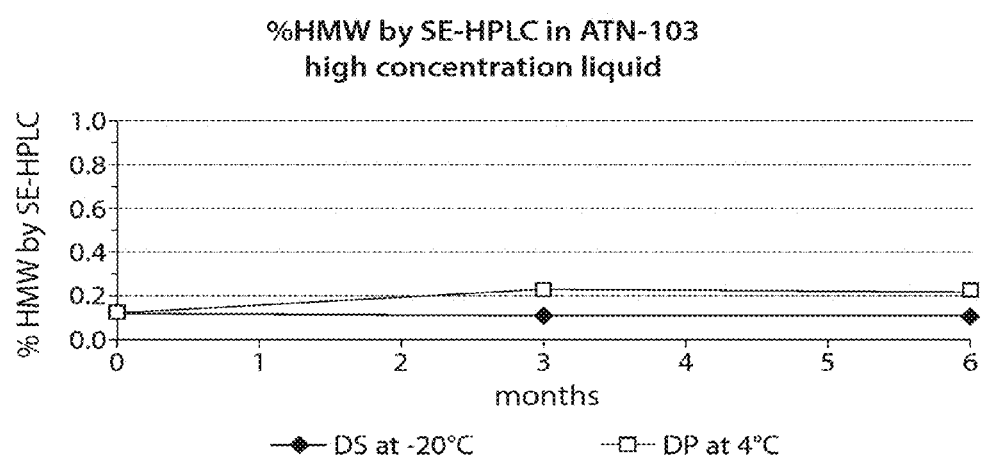
FIG. 8 depicts SE-HPLC results for % HMW species of high concentration liquid formulation after storage for up to six months at the temperatures indicated.

The percentage of HMW species was assayed using SEC-HPLC. The percentage of high molecular weight species in the high concentration liquid formulation before storage was between 0.1%-0.15% of the total protein in the formulation and was about 0.1% in samples stored at −20° C., and about 0.2% in samples stored at 4° C. up to six months storage (FIG. 8). Thus, there was no substantial increase in the level of HMW species in samples stored at −20° C. and 4° C. for at least six months.

Figure 9:
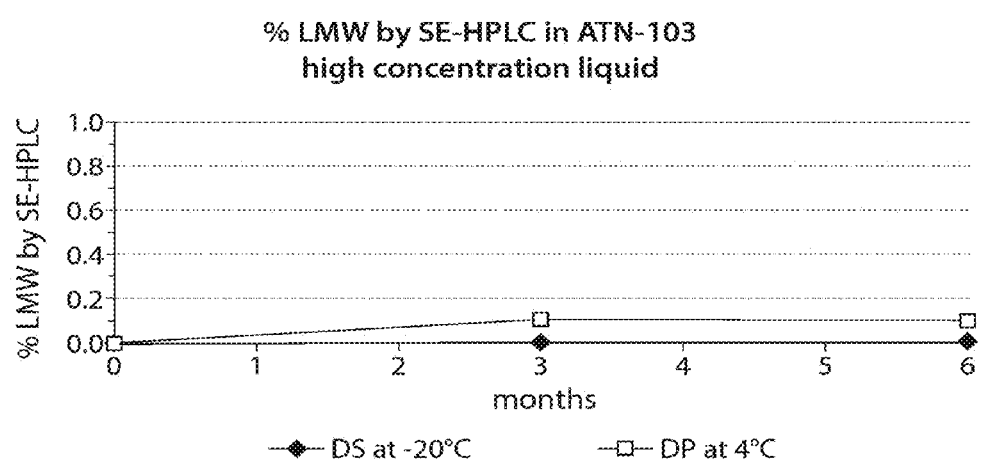
FIG. 9 depicts SE-HPLC results for % LMW species of high concentration liquid formulation after storage for up to six months at the temperatures indicated.

The percentage of LMW species in the high concentration liquid TNF-binding Nanobody™ formulation was also assayed in the TNF-binding Nanobody™ liquid formulation. The percentage of LMW species in the formulation was below limit of detection (i.e. 0.0%) at temperature of −20° C., and was about 0.1% in samples stored at 4° C. for up to six months (FIG. 9). Thus, there was no substantial increase in the level of LMW species in samples stored at −20° C. and 4° C. for at least six months.

The percentage of LMW species was assayed using SE-HPLC. The percentage of LMW species in the high concentration liquid formulation was below limit of detection (i.e. 0.0%) at temperatures of 4° C., 25° C. and 40° C. for up to six months.

Figure 10:
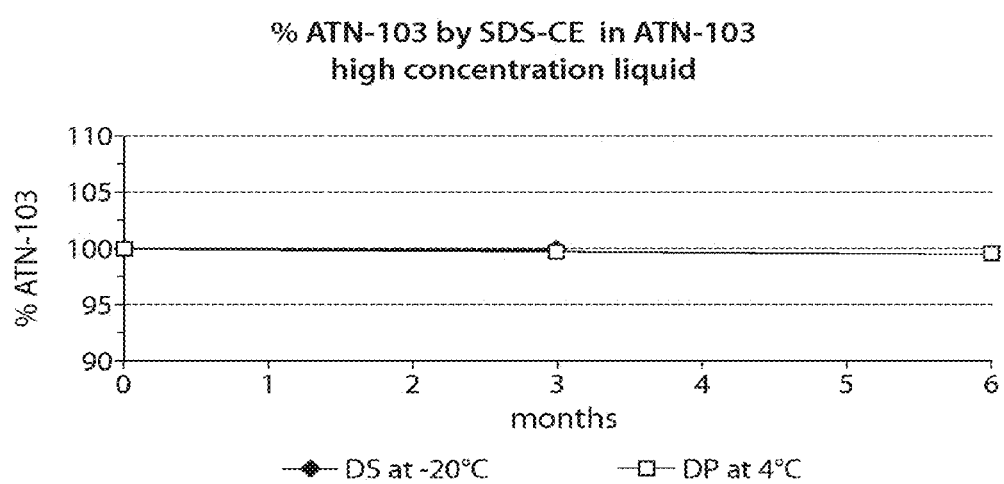
FIG. 10 depicts SDS-CE results for % ATN-103 of high concentration liquid formulation after storage for up to six months at the temperatures indicated.

The percentage of TNF-binding Nanobody™ was assayed using SDS-CE. The initial percentage of TNF-binding Nanobody™ in the high concentration liquid formulation was about 100% and did not change substantially for any of the samples over the six-month period of testing (FIG. 10).

The percentage of non-product impurity was assayed using SDS-CE. Negligible non-product impurity was observed by SDS-CE for liquid high concentration TNF-binding Nanobody™ formulation at temperatures of −20° C. and 4° C. for up to six months.

The high concentration liquid formulations were also tested for identity using CEX-HPLC. CEX-HPLC is employed as a test of identity. The elution profile for TNF-binding of high concentration liquid formulation was comparable to reference standard at temperatures of −20° C. and 4° C. for up to six months. The relative retention time of designated peak was unchanged at 1.00 standard at temperatures of −20° C. and 4° C. for up to six months.

The data described herein show limited changes in degradation products as a function of storage time at various temperatures.

Example 4: Stability of High Concentration Liquid Formulation of TNF-Binding Nanobody™ in a Liquid Prefilled Syringe (12 Months Duration)

The stability of an TNF-binding Nanobody™ high concentration liquid filled into a prefilled syringe in the following formulation: 10 mM Histidine, 5% Sucrose, 0.01% Polysorbate 80, approximately 80 mg/mL TNF-binding Nanobody™, at pH 6.0 was assessed by percentage of HMW and percentage of LMW by SE-HPLC and percentage of acidic and basic species by CEX-HPLC, and assessment of relative retention time and comparability of elution profile to TNF-binding Nanobody™ reference standard. The formulation was stored at 4° C. for twelve months, at 25° C. for three months, and at 40° C. for two months.

Figure 11:
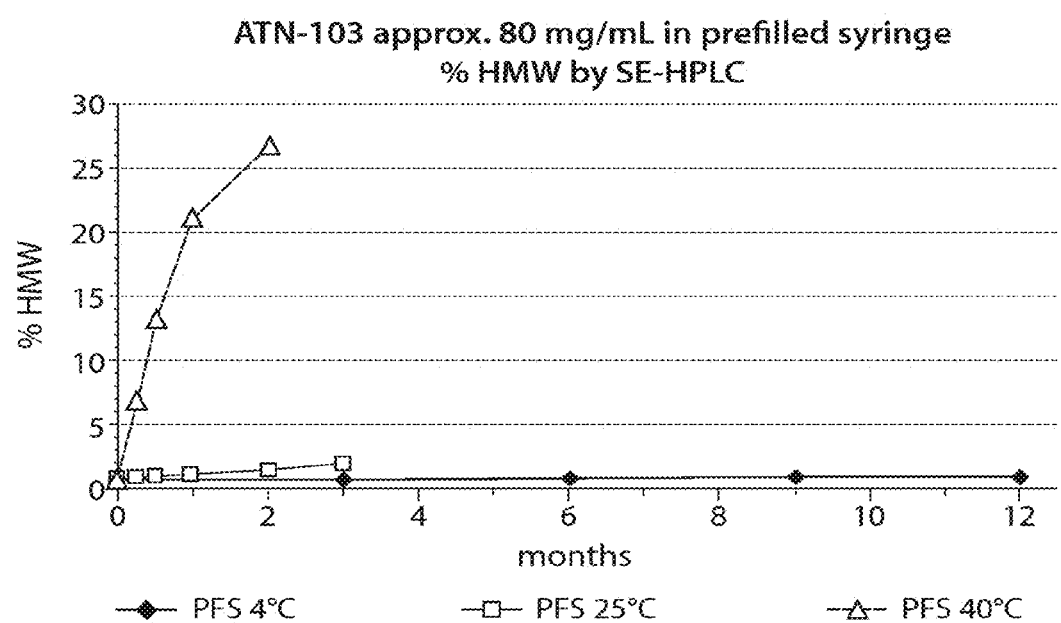
FIG. 11 depicts SE-HPLC results for % HMW species of high concentration liquid formulation in a prefilled syringe.

At the initial time point, there were about 0.7% HMW species. After twelve months at, 4° C. there was a minimal increase to about 0.8% HMW species. After three months at 25° C., the HMW species increased to about 1.8%. After two months at 40° C., the HMW species increased over time to about 27% (FIG. 11).

Figure 12:
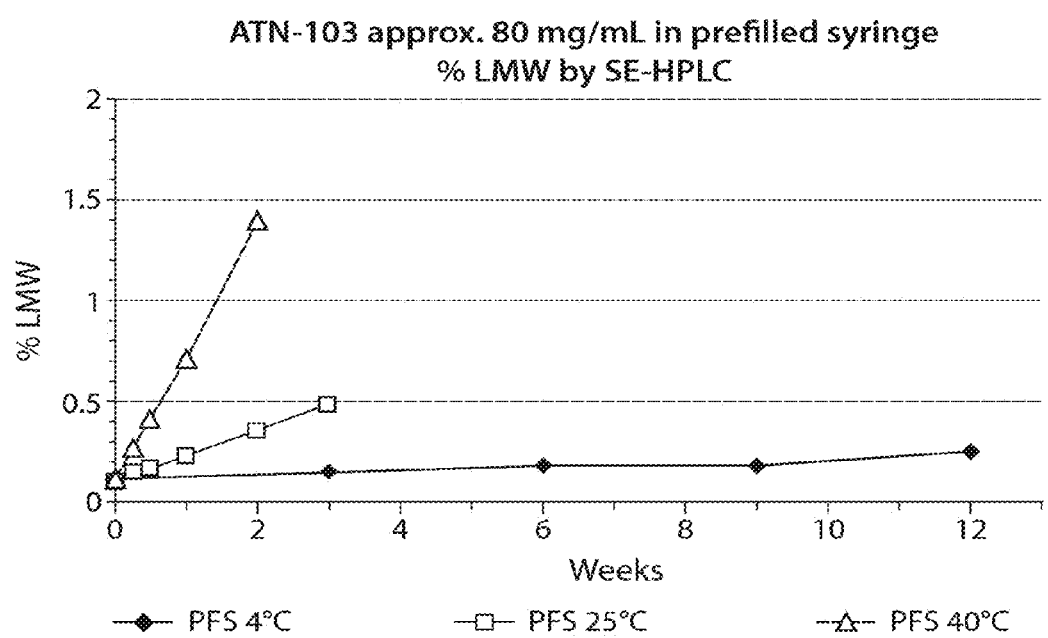
FIG. 12 depicts SE-HPLC results for % LMW species of high concentration liquid formulation in a prefilled syringe.

At the initial time point, there were about 0.1% LMW species. After twelve months at 4° C. there was a minimal increase to 0.25% LMW species. After three months at 25° C., there was a small increase to about 0.5% LMW. After two months at 40° C., the degradation increased over time to about 1.4% LMW species (FIG. 12).

Figure 13:
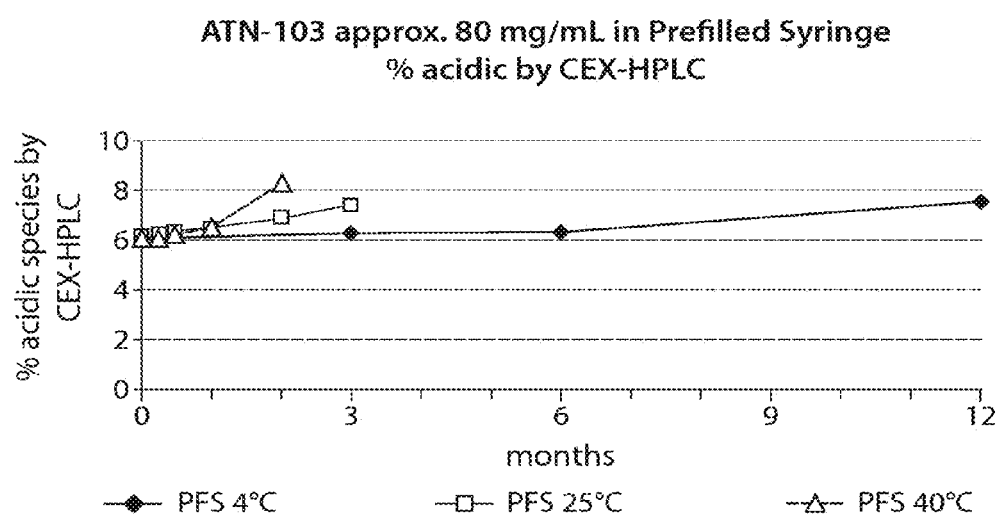
FIG. 13 depicts results for % acidic species by CEX-HPLC of high concentration liquid formulation in a prefilled syringe.

At the initial time point, there were about 6% acidic species. After twelve months at 4° C. there were about 7.5% acidic species. After three months at 25° C., there were about 7.3% acidic species, with the acidic species increasing over time. After two months at 40° C., the acidic species increased over time to about 8.3% (FIG. 13).

Figure 14:
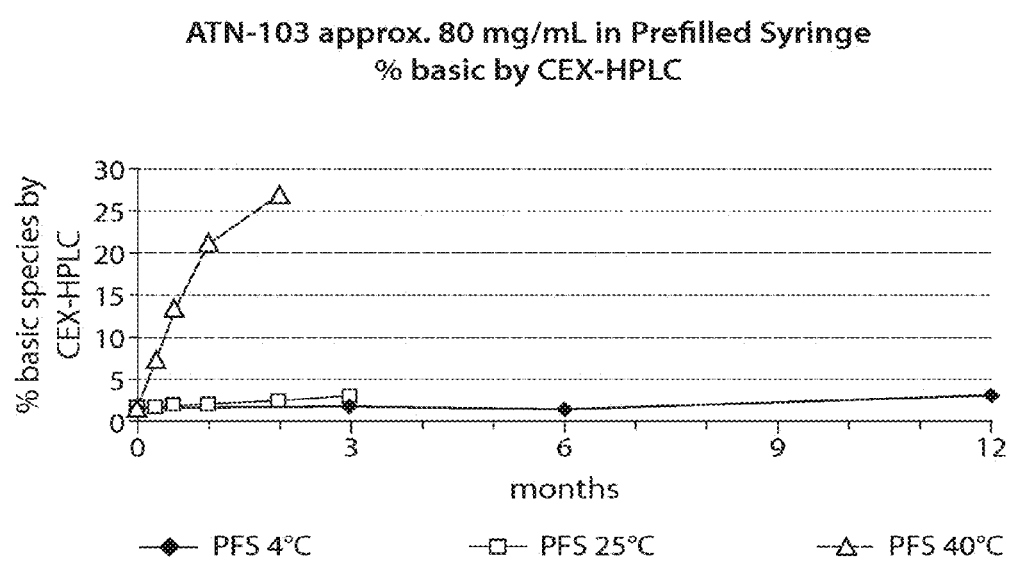
FIG. 14 depicts results for % basic species by CEX-HPLC of high concentration liquid formulation in a prefilled syringe.

At the initial time point, there were about 1.7% basic species. After twelve months at 4° C., there were about 2.9% basic species. After three months at 25° C., there were about 2.9% basic species, with the basic species increasing over time. After two months at 40° C., the basic species increased over time to about 27% (FIG. 14).

The relative retention times and elution profiles of all samples were comparable to TNF-binding Nanobody™ reference standard.

The data show limited changes in degradation products as a function of storage time at 4° C. and 25° C., indicating the formulation is suitable as a liquid in a prefilled syringe. Some noticeable changes in degradation products were observed at 40° C., which is a stress condition for a liquid.

Example 5: Stability of ATN-103 High Concentration Liquids—Other Formulations (Identification of Other Stabilizing and Destabilizing Excipients)

In order to screen for possible excipients for an TNF-binding Nanobody™ liquid formulation, the stability of other high concentration TNF-binding Nanobody™ liquid formulations were examined. Supplemental work was performed using various excipients to provide further stability and to make the formulation isotonic (suitable for injection in human subjects). TNF-binding Nanobody™ concentration is ranged from 88 mg/mL to 100 mg/mL.

The formulations examined were:
1. 10 mM histidine, 5% sucrose, 0.01% polysorbate-80, 100 mM Arginine (base), pH 5.8
2. 10 mM histidine, 5% sucrose, 0.01% polysorbate-80, 55 mM NaCl, pH 6.1
3. 10 mM histidine, 5% sucrose, 0.01% polysorbate-80, 55 mM Arginine HCl, pH 6.1
4. 10 mM histidine, 5% sucrose, 0.01% polysorbate-80, 100 mM Glycine, pH 6.0
5. 10 mM histidine, 5% sucrose, 0.01% polysorbate-80, 100 mM Methionine, pH 6.0
6. 10 mM histidine, 8% sucrose, 0.01% polysorbate-80, pH 6.0

CTL: 10 mM histidine, 5% sucrose, 0.01% polysorbate-80, pH 6.0

The initial solution properties were analyzed for pH, osmolality, concentration, turbidity, and viscosity. All formulations resulted in isotonic solutions and showed acceptable clarity via A455 measurement and low viscosity (2.4 cP to 3.1 cP), showing prefilled syringe and auto-injector feasibility.

TABLE 2

Initial Solution Properties

| Formulation | mOsm | pH | mg/mL | Turbidity | Viscosity (cP) |
| --- | --- | --- | --- | --- | --- |
| 1 | 356 | 5.82 | 98 | <III | 3.1 |
| 2 | 312 | 6.13 | 88 | <III | 2.6 |
| 3 | 303 | 6.12 | 89 | <III | 2.6 |
| 4 | 305 | 6.05 | 88 | <III | 2.4 |
| 5 | 309 | 5.97 | 99 | <III | 2.8 |
| 6 | 306 | 6.03 | 88 | <III | 2.6 |
| CTL/0 | 197 | 6.01 | 100 | <III | 2.8 |

Figure 15:
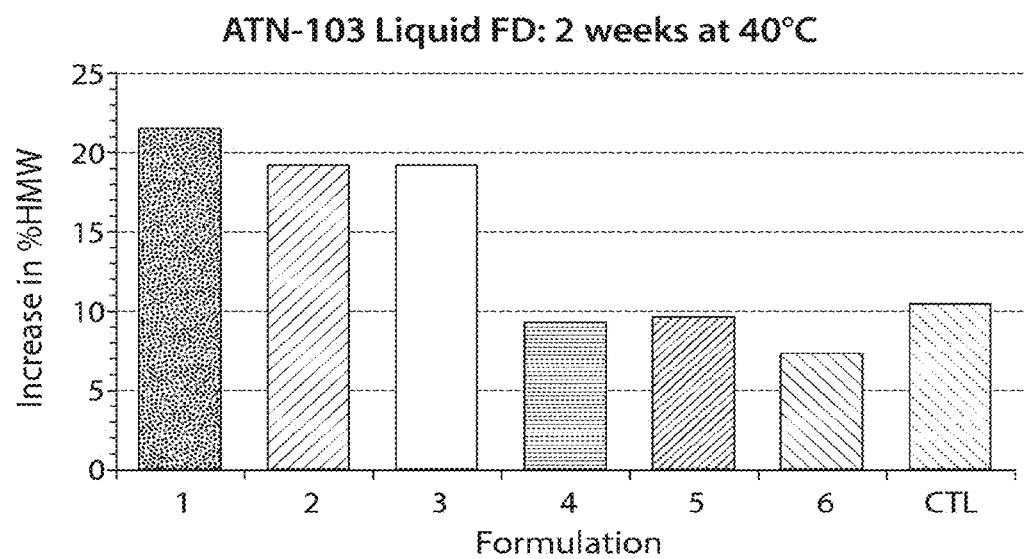
FIG. 15 depicts SE-HPLC results for % HMW species of high concentration liquid formulations—Other Formulations (identification of other stabilizing and destabilizing excipients).
Figure 16:
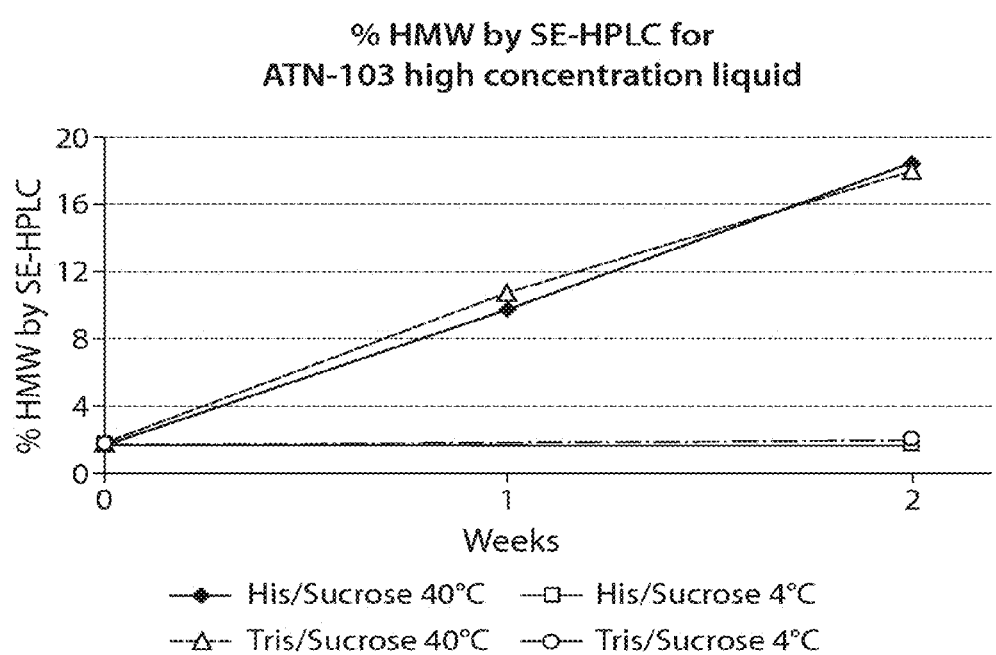
FIG. 16 depicts SE-HPLC results for % HMW species for TNF-binding Nanobody™ high concentration liquid.
Figure 17:
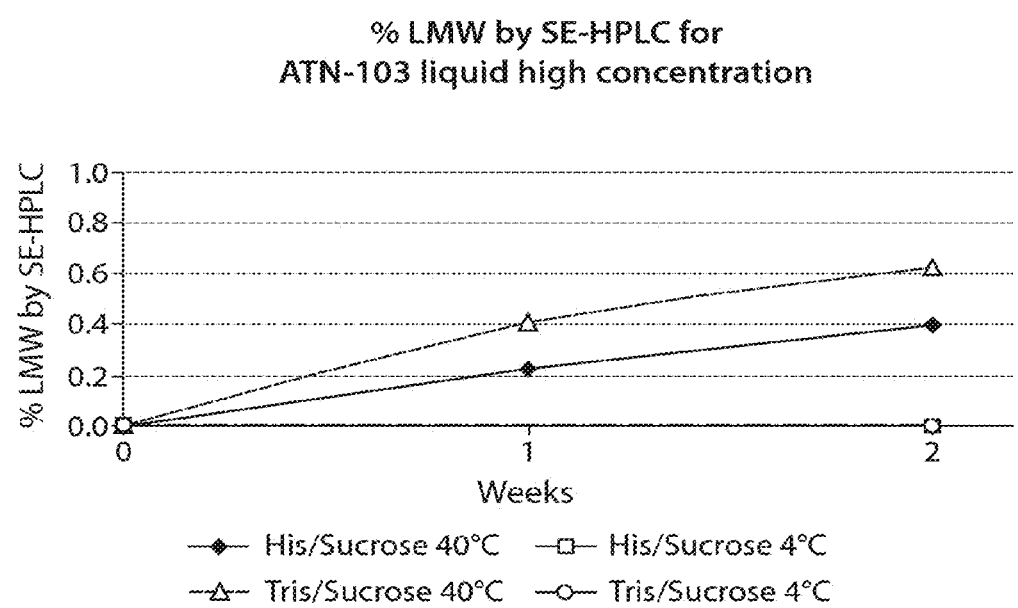
FIG. 17 depicts SE-HPLC results for % LMW species for TNF-binding Nanobody™ high concentration liquid.
Figure 18:
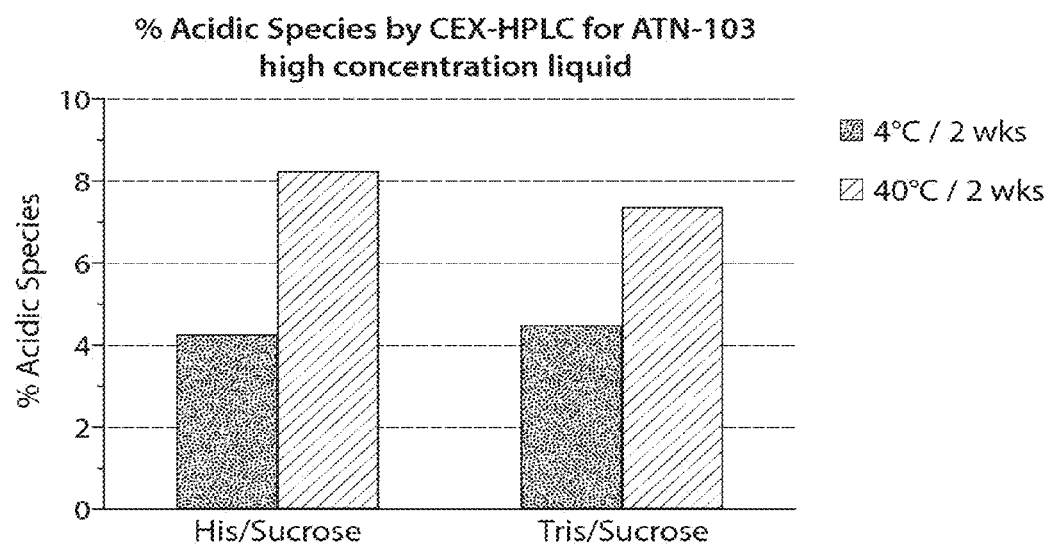
FIG. 18 depicts CEX-HPLC results for % Acidic species for TNF-binding Nanobody™ high concentration liquid.
Figure 19:
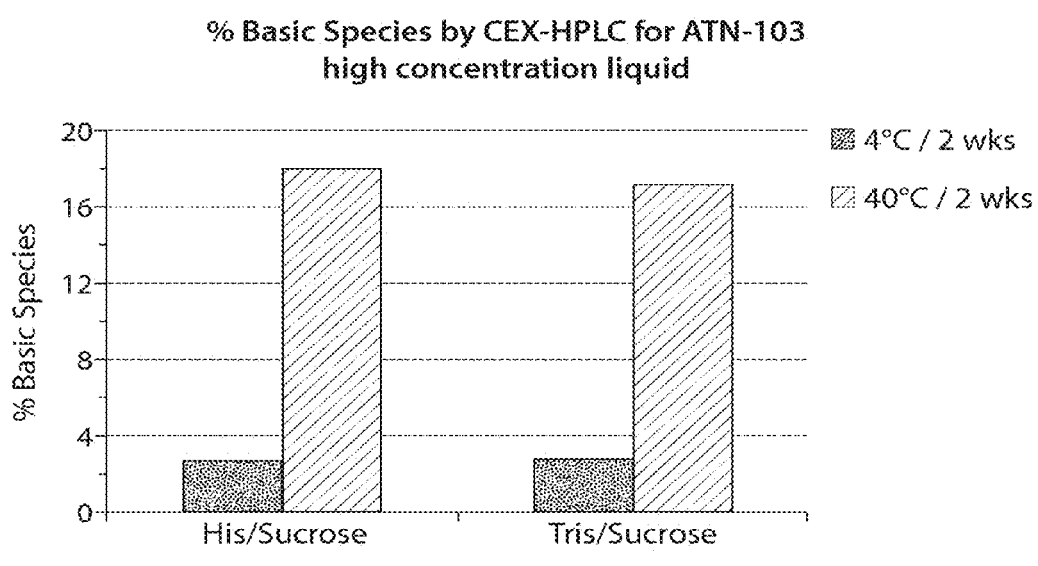
FIG. 19 depicts CEX-HPLC results for % Basic species for TNF-binding Nanobody™ high concentration liquid.
Figure 20:
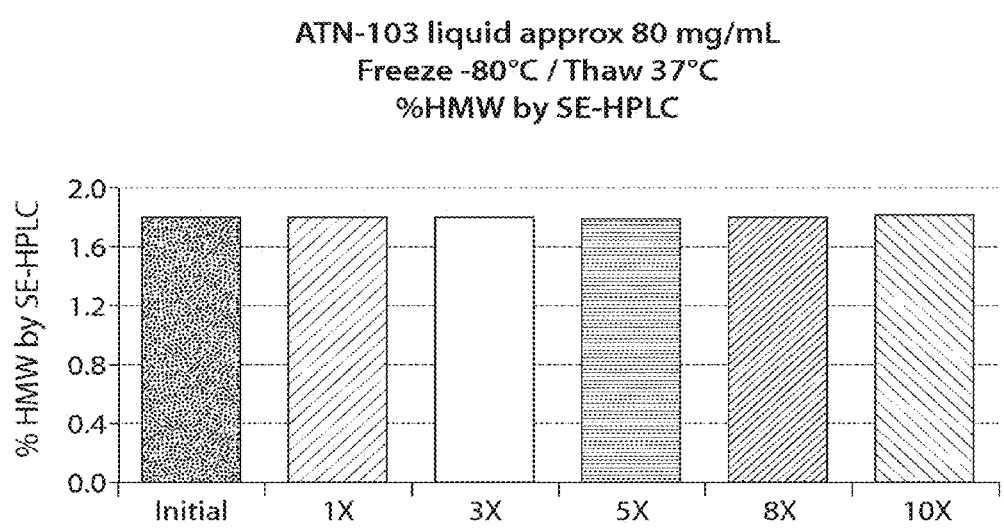
FIG. 20 depicts SE-HPLC results for % HMW species for TNF-binding Nanobody™ high concentration liquid after 10× freeze-thaw cycles.
Figure 21:
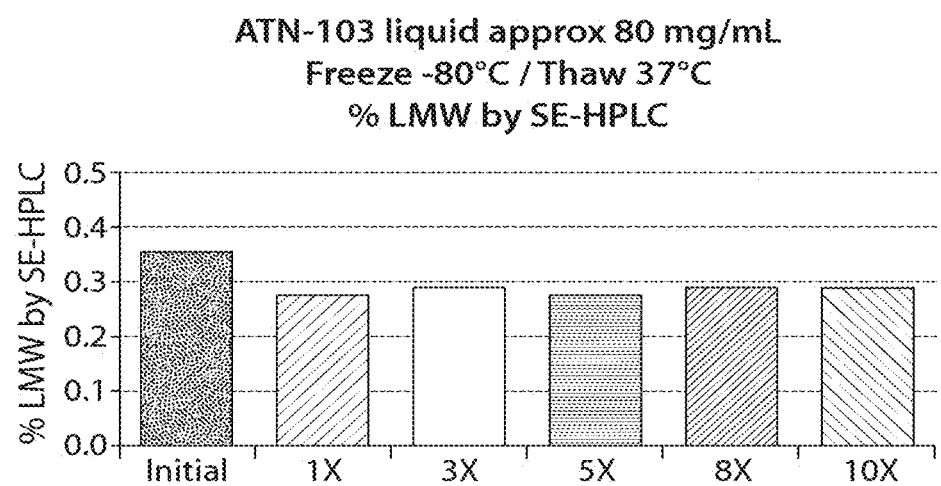
FIG. 21 depicts SE-HPLC results for % LMW species for TNF-binding Nanobody™ high concentration liquid after 10× freeze-thaw cycles.
Figure 22:
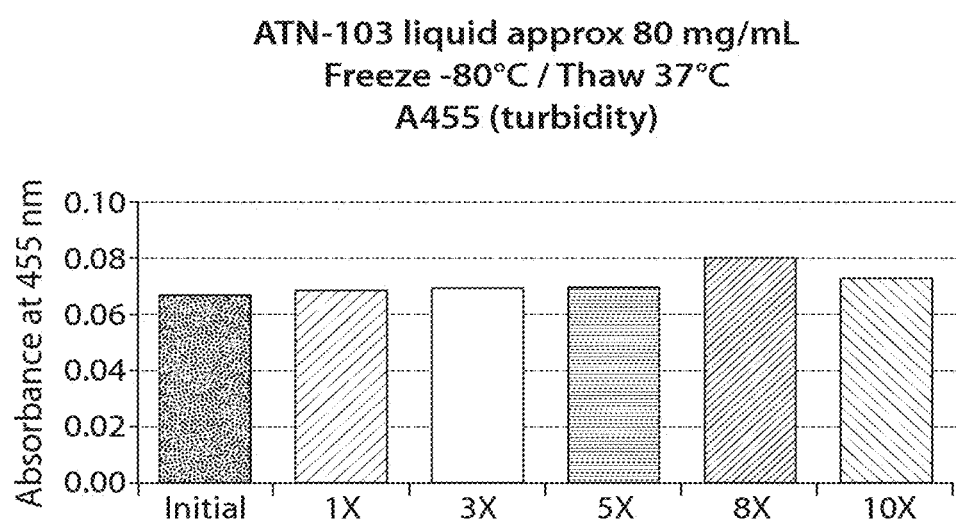
FIG. 22 depicts Turbidity (Absorbance at 455 nm) results for TNF-binding Nanobody™ high concentration liquid after 10× freeze-thaw cycles.
Figure 23:
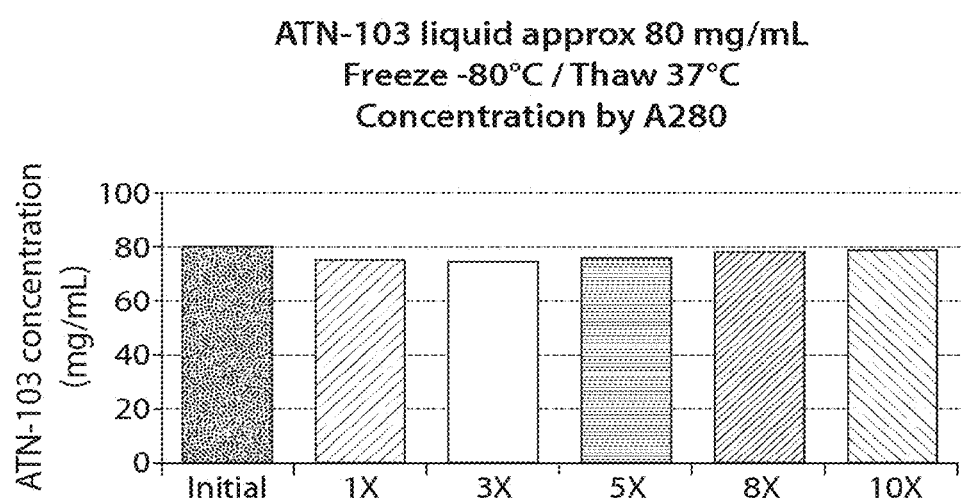
FIG. 23 depicts Concentration (by UV absorbance at 280 nm) results for TNF-binding Nanobody™ high concentration liquid after 10× freeze-thaw cycles.

The stability of the high concentration liquid was assessed by percentage of HMW and percentage of LMW by SE-HPLC. These materials were placed on stability at 5° C., 25° C. and 40° C. for 3 months. Data from 40° C. 2 weeks is shown in FIG. 15.

Some noticeable changes in degradation products were observed at 40° C., which is a stress condition for a liquid. Brief accelerated stability (2 weeks at 40° C.) shows that formulations 4, 5 and 6 offer comparable or improved stability compared to the control (10 mM histidine, 5% sucrose, 0.01% polysorbate-80, pH 6.0). Formulations 1, 2 and 3 appear to have a negative impact on stability.

The data show that glycine, methionine, and increased sucrose are stabilizing to high concentration TNF-binding Nanobody™ liquid formulations. The data show that arginine base, arginine hydrochloride and sodium chloride may be de-stabilizing to high concentration TNF-binding Nanobody™ liquid formulations under some conditions.

Example 6: Stability of TNF-Binding Nanobody™ of High Concentration Liquid Formulation, Short-Term (2 Weeks Duration), Histidine and Tris Buffers Stability of TNF-binding Nanobody™ as a liquid is exemplified in the following FIGS. 16-19. Two formulations were examined: ATN-103 at 118 mg/mL in 20 mM Histidine, 5% Sucrose, pH 6.0; and ATN-103 at 117 mg/mL in 20 mM Tris, 5% Sucrose, pH 7.2. The stability of the formulations was assessed by percentage of HMW and percentage of LMW by SE-HPLC, and percentage of acidic and percentage of basic species by CEX-HPLC. The data show limited changes in degradation products as a function of storage time at 4° C. Some noticeable changes in degradation products were observed at 40° C., which is a stress condition for a liquid. The data show that the stability of TNF-binding Nanobody™ in histidine and tris buffers is essentially similar under these formulation conditions, with histidine performing slightly more favorably (slightly less LMW). Pre-formulation activities would later determine that the elevated pH (7 or greater) results in a greater degree of LMW formation, explaining the advantage observed below.

Example 7: Stability of High Concentration Liquid Formulation of TNF-Binding Nanobody™: Assessment of Interfacial Stresses (Freeze/Thaw)

FIGS. 20-23 demonstrate the stability of liquid TNF-binding Nanobody™ formulation at approximately 80 mg/mL in 10 mM Histidine, 5% Sucrose, 0.01% Polysorbate 80, pH 6.0. Assessment was based on Size exclusion-HPLC, turbidity, and concentration assessment following multiple freeze-thaw cycling from −80° C. and 37° C.

The data show limited change in stability as a function of multiple freeze-thaw cycling from −80° C. and 37° C.

Figure 24:
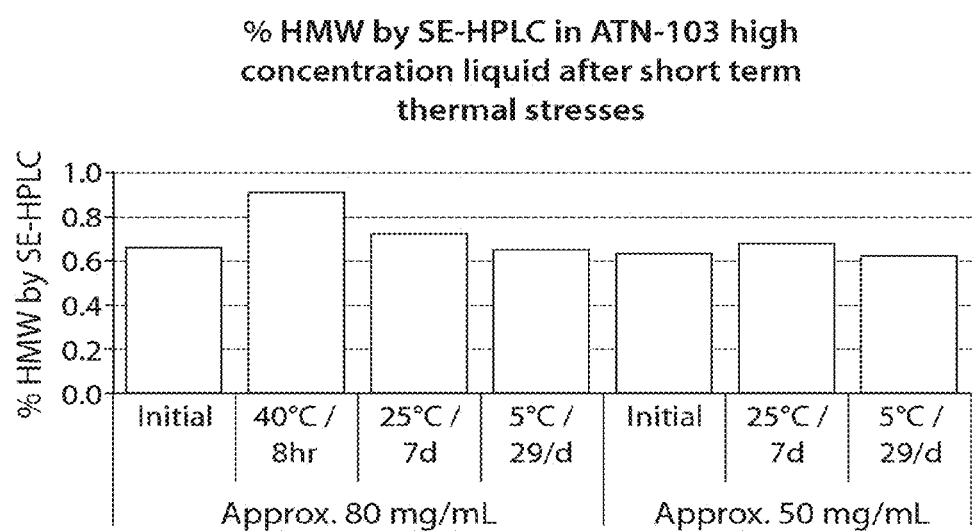
FIG. 24 depicts High Concentration Liquid Formulation of TNF-binding Nanobody™: % HMW by SE-HPLC after of short term thermal stresses potentially encountered in manufacturing processes.

Example 8: Stability of High Concentration Liquid Formulation of TNF-Binding Nanobody™: Assessment of Short-Term Thermal Stresses Potentially Encountered in Manufacturing Processes FIG. 24 demonstrates that liquid TNF-binding Nanobody™ is robust to short-term thermal stresses that might potentially be encountered during drug substance and drug product manufacturing processes. The high concentration liquid was studied in 10 mM Histidine, 5% Sucrose, 0.01% Polysorbate 80, pH 6.0, at approximately 80 mg/mL and 50 mg/mL. Assessment was based on percentage of HMW and percentage of LMW by Size exclusion-HPLC, after exposure for 8 hours at 40° C., 7 days at 25° C., and 29 days at 5° C. The data show limited changes in aggregates as a function of storage time at 5° C. and 25° C. Some changes in aggregates were observed at 40° C., which is a stress condition for a liquid.

The percentage of LMW species by SE-HPLC for TNF-binding Nanobody™ high concentration liquid was below limit of detection (i.e. 0.0%) at the temperatures and durations indicated.

Figure 25:
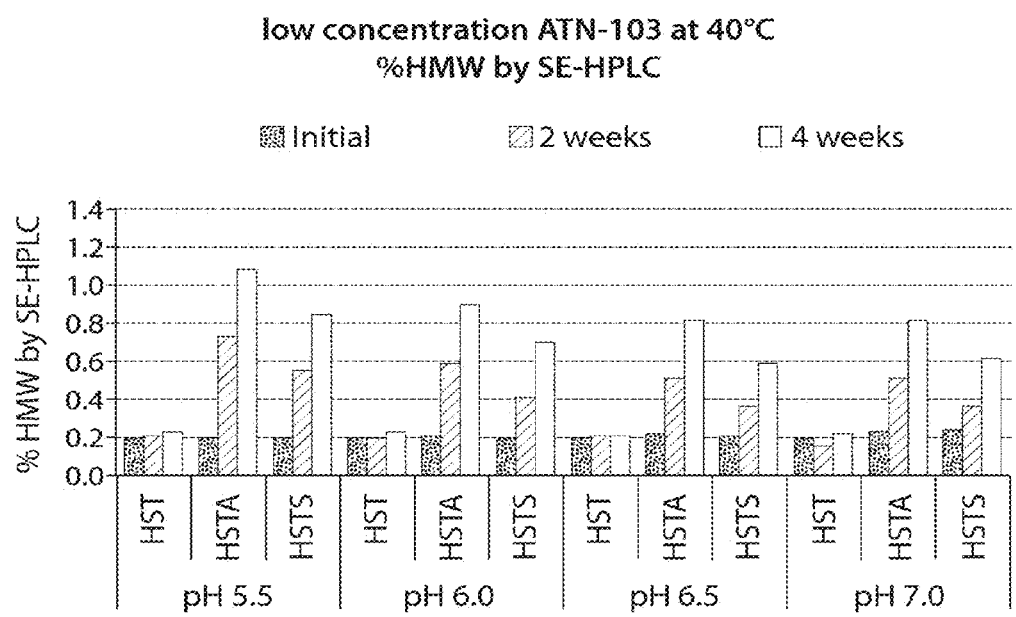
FIG. 25 depicts SE-HPLC results for % HMW species of low concentration liquid formulation as a function of pH and formulation (40° C.).
Figure 26:
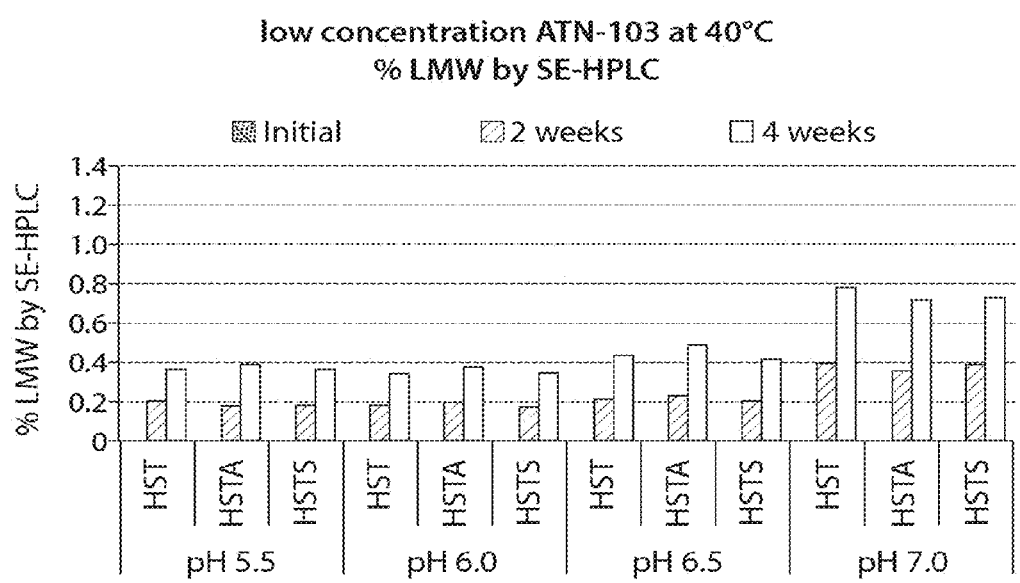
FIG. 26 depicts SE-HPLC results for % LMW species of low concentration liquid formulation as a function of pH and formulation (40° C.).

Example 9: Stability of Low Concentration Liquid Formulation of ATN-103: Assessment of Optimal pH and Formulation FIGS. 25-28 demonstrate the stability of a liquid TNF-binding Nanobody™ formulations at low concentration (approximately 1 mg/mL) buffered at pH 5.5, 6.0, 6.5, and 7.0. The stability of low concentration liquid TNF-binding Nanobody™ was examined as a function of formulation and pH, in response to stress such as exposure to 40° C. temperature (FIGS. 25 and 26), shaking (FIG. 28), and freeze/thaw. Four pH were evaluated for each of the three following formulations: 10 mM histidine, 5% sucrose, 0.01% Tween-80; 10 mM histidine, 5% sucrose, 0.01% Tween-80, 150 mM arginine HCl; and 10 mM histidine, 5% sucrose, 0.01% Tween-80, 75 mM sodium chloride. In this data set, Tween-80 is used as a synonym for Polysorbate-80. Study samples were evaluated using SE-HPLC and UV (for both concentration and turbidity—measured by A455).

Figure Codes:
HST: 10 mM histidine, 5% sucrose, 0.01% Tween-80
HSTA: 10 mM histidine, 5% sucrose, 0.01% Tween-80, 150 mM arginine HCl
HSTS: 10 mM histidine, 5% sucrose, 0.01% Tween-80, 75 mM sodium chloride Results show that pH range of 5.5-7.0 is suitable for the formulation. The data show that under some conditions, pH 7.0 may show some detrimental effects (increased low molecular weight species). The data show that there is no significant benefit in adding arginine HCl or sodium chloride to the drug substance formulation, and in some cases may be destabilizing.

Figure 27:
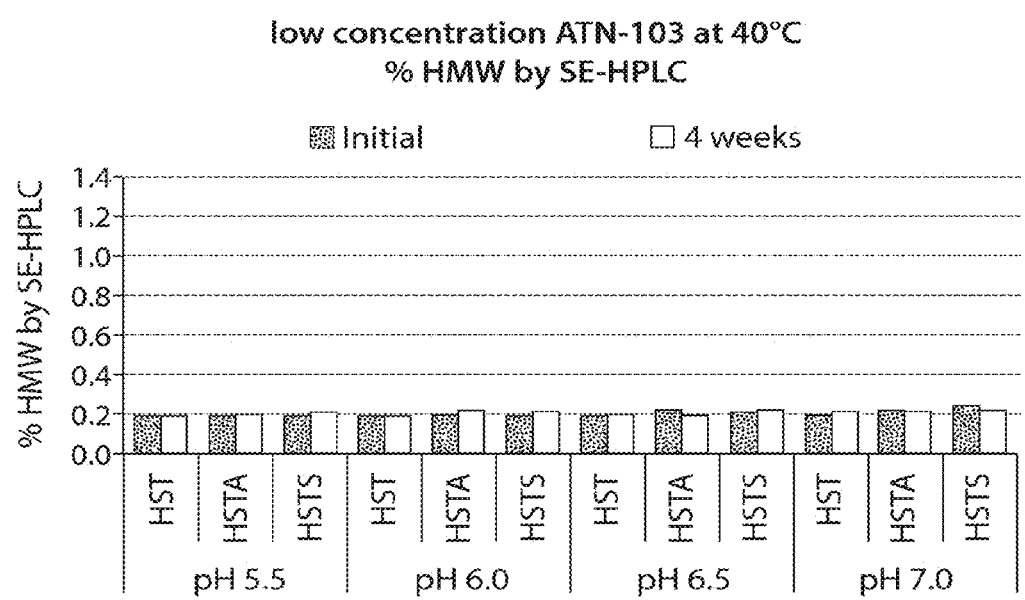
FIG. 27 depicts SE-HPLC results for % HMW species of low concentration liquid formulation as a function of pH and formulation (4° C.).

FIG. 27 shows the percentage of HMW species by SE-HPLC for TNF-binding Nanobody™ after storage at 4° C., where essentially no change was observed after 4 weeks. The percentage of LMW species by SE-HPLC for TNF-binding Nanobody™ low concentration was below limit of detection (i.e. 0.0%) at 4° C. for all solution conditions tested. No significant changes were observed in HMW or LMW species by SE-HPLC, or UV A280, or A455, as a result of multiple freeze-thaw cycles.

Figure 28:
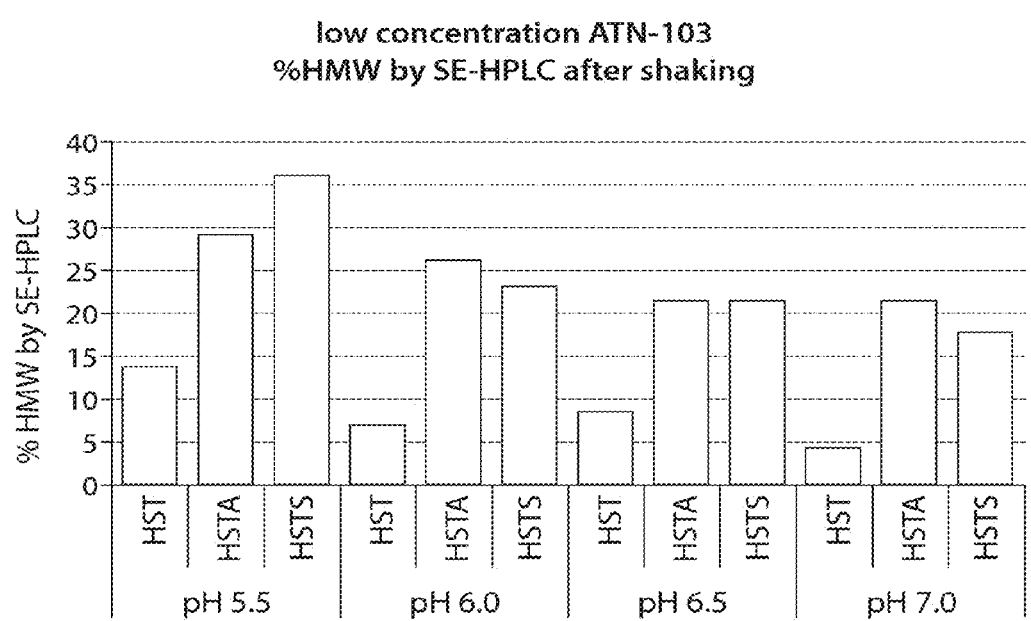
FIG. 28 depicts SE-HPLC results for % HMW species of low concentration liquid formulation as a function of pH and formulation after shaking.

Example 10: Low Concentration TNF-Binding Nanobody™ Liquid: Assessment of the Effect of Shaking as a Function of pH and Formulation Data is also presented to show that TNF-binding Nanobody™ is sensitive to shaking at 300 rpm for 4 hours (at 15° C.) over this pH range (FIG. 28). Formulations containing sodium chloride and arginine are especially sensitive to shaking. The histidine, sucrose, tween-80 formulation showed the least high molecular weight degradation within each pH group. The histidine, sucrose, tween-80 formulation at pH 6.0 and 7.0 showed the least HMW degradation.

The UV absorbance of low concentration TNF-binding Nanobody™ after shaking was monitored at 280 nm (to monitor concentration) and 455 nm (to monitor turbidity). No significant changes were observed as a result of shaking.

Low concentration TNF-binding Nanobody™ solutions were examined after multiple freeze-thaw cycles by SE-HPLC and UV analysis at 280 nm (to monitor concentration) and 455 nm (to monitor turbidity). No significant changes were observed SE-HPLC or UV A280 or A455 as a result of multiple freeze-thaw cycles.

Figure 31:
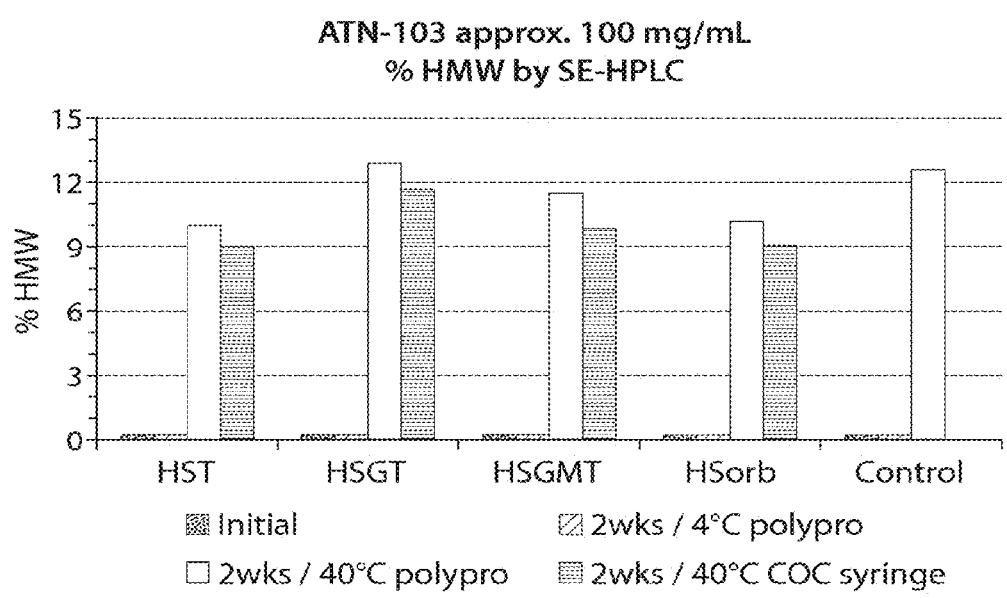
FIG. 31 are bar graphs depicting the % of HMW species detected by SE-HPLC of the indicated formulations containing approximately 100 mg/ml of ATN-103 (HST, HSGT, HSGMT, HSorb and control) stored under the conditions indicated.
Figure 32:
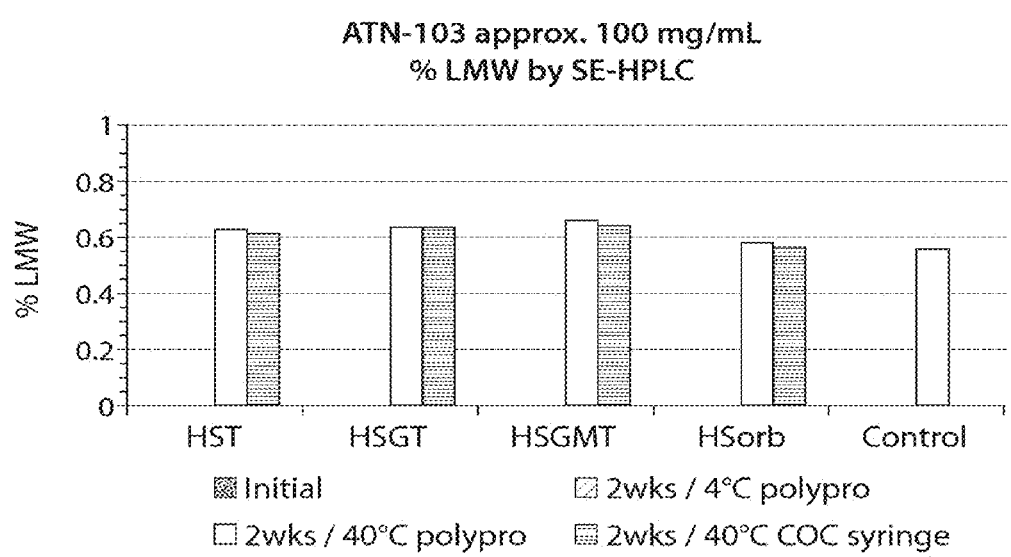
FIG. 32 are bar graphs depicting the % of LMW species detected by SE-HPLC of the indicated formulations containing approximately 100 mg/ml of ATN-103 (HST, HSGT, HSGMT, HSorb and control) stored under the conditions indicated. No LMW species was detected at the initial time point or after two weeks at 4° C.

Example 11: Stability of TNF-Binding Nanobody™ of High Concentration Liquid Formulation, Short-Term (2 Weeks Duration), Examining Tonicity Adjusting Agents The stability of the TNF-binding Nanobody™ as a liquid is exemplified in the following:

Five formulations were examined as shown in FIGS. 31 and 32 referred to herein as HST, HSGT, HSGMT, HSorb and Control. Each of the formulations examined described below.

| FIGS. 31 and 32 | Formulations |
| --- | --- |
| HST | 100 mg/mL TNF-binding Nanobody ™, 20 mM histidine, 8% sucrose, 0.01% polysorbate 80 |
| HSGT | 100 mg/mL TNF-binding Nanobody ™, 20 mM histidine, 5% sucrose, 80 mM glycine, 0.01% polysorbate 80 |
| HSGMT | 100 mg/mL TNF-binding Nanobody ™, 20 mM histidine, 5% sucrose, 80 mM glycine, 10 mM methionine, 0.01% polysorbate 80 |
| HSorb | 100 mg/mL TNF-binding Nanobody ™, 20 mM histidine, 5% sorbitol |
| Control | 100 mg/mL TNF-binding Nanobody ™, 20 mM histidine, 5% sucrose |

The formulations were stored as a liquid for two weeks at 4° C. and 40° C. (stress condition), in polypropylene tubes and in cyclic olefin copolymer prefilled syringe with a rubber plunger.

The stability of the formulations was assessed by percentage of HMW and percentage of LMW by SE-HPLC as depicted in FIGS. 31 and 32. The data show limited changes in degradation products as a function of storage time at 4° C. For the samples shown in FIG. 32, no LMW was detected at the initial time point, or after two weeks at 4° C. LMW was only detected in the 40° C. (stressed) samples. The data show five formulations show comparable changes in degradation products as a function of storage time at the stress condition 40° C. Thus, the data show that all formulations are suitable for liquid dosage form.

Example 12: Stability of TNF-Binding Nanobody™ at Low Concentration and High Concentration Liquid Formulation, Confirming Target Formulation, and Examining Primary Packaging Containers Stability of TNF-binding Nanobody™ as a liquid is exemplified in the following: Three formulations were examined:
  (a) 10 mg/mL TNF-binding Nanobody™, 20 mM histidine, 7.5% sucrose, 0.01% polysorbate 80;
  (b) 50 mg/mL TNF-binding Nanobody™, 20 mM histidine, 7.5% sucrose, 0.01% polysorbate 80;
  (c) 100 mg/mL TNF-binding Nanobody™, 20 mM histidine, 7.5% sucrose, 0.01% polysorbate 80.

The formulation was prepared in the following primary packaging containers:
  (a) prefillable Type I pharmaceutical grade glass syringe from one vendor and a West 4432 siliconized gray rubber plunger
  (b) prefillable glass Type I pharmaceutical grade syringe from a second vendor and a West 4432 siliconized gray rubber plunger
  (c) prefillable cyclic olefin copolymer and a West 4432 siliconized gray rubber plunger The formulations were analyzed at t=0 and were found to be satisfactory. The formulation has been stored at 4° C., 25° C. and 40° C. for three months.

EQUIVALENTS

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A formulation comprising:
   (a) a single domain antigen binding (SDAB) molecule at a concentration from about 0.1 mg/mL to about 350 mg/mL, comprising one or more single domain molecules, wherein at least one of the single domain molecule binds to human serum albumin (HSA) and comprises three CDRs having the amino sequences: SFGMS (SEQ ID NO: 5) (CDR1), SISGSGSDTLYADSVKG (SEQ ID NO: 6) (CDR2) and GGSLSR (SEQ ID NO: 7) (CDR3);
   (b) a lyoprotectant; and
   (c) a histidine buffer at a concentration about 5 to about 50 mM, such that the pH of the formulation is about 5.0 to 7.5.

2. The formulation of claim 1, wherein the at least one single domain molecule that binds to HSA is selected from the group consisting of:
   single domain molecules comprising a variable region having the amino acid sequence from about amino acids 125 to 239 of SEQ ID NO: 1,
   single domain molecules comprising a variable region that differs by up to 10 amino acids from said variable region,
   single domain molecules having at least 85%, 90%, 95% or more amino acid identity relative to the amino acid sequence shown in SEQ ID NO: 1, and
   single domain molecules having up to 20, 15, 10, 5, 4, 3, 2, or 1 amino acid changes relative to the amino acid sequence shown in SEQ ID NO: 1.

3. The formulation of claim 1, wherein the SDAB molecule is chosen from the group consisting of monovalent, multivalent, bivalent, trivalent, tetravalent, monospecific, multispecific, bispecific, trispecific and tetraspecific SDAB molecules.

4. The formulation of claim 1, wherein the at least one single domain molecule that binds to HSA is ALB1, ALB6, ALB7, ALB8, ALB9, or ALB10 disclosed in U.S. Pat. No. 8,703,131.

5. The formulation of claim 1, wherein said lyoprotectant is selected from the group consisting of
sugars, optionally sucrose, sorbitol, and/or trehalose;
amino acids, optionally monosodium glutamate and/or histidine;
methylamines, optionally betaine;
lyotrophic salts, optionally magnesium sulfate;
polyols, optionally trihydric sugar alcohols and/or higher sugar alcohols, including glycerin, erythritol, glycerol, arabitol, xylitol, and/or mannitol;
propylene glycol;
polyethylene glycol;
pluronics; and
combinations thereof.

6. The formulation of claim 1, wherein the SDAB molecule further comprises at least one or two single domain molecules that bind to tumor necrosis factor alpha (TNFα).

7. The formulation of claim 1, wherein the SDAB molecule further comprises one or more single domain molecules that is useful in treating autoimmune disorders, arthritis, rheumatoid arthritis, juvenile rheumatoid arthritis, osteoarthritis, polyarticular juvenile idiopathic arthritis (JIA), psoriatic arthritis, lupus-associated arthritis, ankylosing spondylitis, scleroderma, systemic lupus erythematosis, Sjogren's syndrome, vasculitis, multiple sclerosis, autoimmune thyroiditis, dermatitis, atopic dermatitis, eczematous dermatitis, myasthenia gravis, inflammatory bowel disease (IBD), Crohn's disease, colitis, ulcerative colitis, diabetes mellitus (type I diabetes), inflammatory conditions of the skin, psoriasis, acute inflammatory conditions, endotoxemia, sepsis, septicaemia, toxic shock syndrome, infectious disease, transplant rejection, and allergy.

8. A kit or an article of manufacture, comprising a container containing the formulation of claim 1, and instructions for use.

9. The kit or article of manufacture of claim 8, wherein the formulation is present in a vial or an injectable syringe.

* * * * *